United States Patent [19]
Hoey

[11] Patent Number: 5,612,455
[45] Date of Patent: Mar. 18, 1997

[54] NUCLEAR FACTORS AND BINDING ASSAY

[75] Inventor: Timothy Hoey, Woodside, Calif.

[73] Assignee: Tularik, Inc., So. San Francisco, Calif.

[21] Appl. No.: 396,479

[22] Filed: Mar. 2, 1995

Related U.S. Application Data

[63] Continuation-in-part of Ser. No. 270,653, Jul. 5, 1994, abandoned.

[51] Int. Cl.⁶ .................................................. C07K 14/47
[52] U.S. Cl. ............................................................ 530/350
[58] Field of Search ............................................... 530/350

[56] References Cited

FOREIGN PATENT DOCUMENTS 9415964  7/1994  WIPO.
9502053  1/1995  WIPO.

OTHER PUBLICATIONS

Li et al, PNAS, Sep. 1991, vol. 88: pp. 7739–7743.
Nolan (1994) Cell 77, 1–20.
Northrop et al. (1994) Nature 369, 497–502.
McCaffrey et al. (1993) Science 262, 7509–754.

*Primary Examiner*—Mindy Fleisher
*Assistant Examiner*—Terry A. McKelvey
*Attorney, Agent, or Firm*—Flehr, Hohbach, Test, Albritton & Herbert

[57] ABSTRACT

The invention provides methods and compositions for identifying pharmacological agents useful in the diagnosis or treatment of disease associated with the expression of a gene modulated by a transcription complex containing at least a human nuclear factor of activated T-cells (hNFAT). The materials include a family of hNFAT proteins, active fragments thereof, and nucleic acids encoding them. The methods are particularly suited to high-throughput screening where one or more steps are performed by a computer controlled electromechanical robot comprising an axial rotatable arm.

6 Claims, No Drawings

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
      ( A ) LENGTH: 3478 base pairs
      ( B ) TYPE: nucleic acid
      ( C ) STRANDEDNESS: double
      ( D ) TOPOLOGY: linear ( i i ) MOLECULE TYPE: cDNA ( i x ) FEATURE:
      ( A ) NAME/KEY: CDS
      ( B ) LOCATION: 223..2987

( x i ) SEQUENCE DESCRIPTION: SEQ ID NO:1:

```
GGAGCAGGAA  GCTCGCGCCG  CCGTCGCCGC  CGCCGCTCAG  CTTCCCCGGG  CGCGTCCAGG      60

ACCCGCTGCG  CCAGGCGCGC  CGTCCCCGGA  CCCGGCGTGC  GTCCCTACGA  GGAAAGGGAC     120

CCCGCCGCTC  GAGCCGCCTC  CGCCAGCCCC  ACTGCGAGGG  GTCCAGAGC   CAGCCGCGCC     180

CGCCCTCGCC  CCCGGCCCCG  CAGCCTTCCC  GCCCTGCGCG  CC ATG AAC GCC CCC         234
                                                  Met Asn Ala Pro
                                                   1

GAG CGG CAG CCC CAA CCC GAC GGC GGG GAC GCC CCA GGC CAC GAG CCT            282
Glu Arg Gln Pro Gln Pro Asp Gly Gly Asp Ala Pro Gly His Glu Pro
  5              10                  15                  20

GGG GGC AGC CCC CAA GAC GAG CTT GAC TTC TCC ATC CTC TTC GAC TAT            330
Gly Gly Ser Pro Gln Asp Glu Leu Asp Phe Ser Ile Leu Phe Asp Tyr
                 25                  30                  35

GAG TAT TTG AAT CCG AAC GAA GAA GAG CCG AAT GCA CAT AAG GTC GCC            378
Glu Tyr Leu Asn Pro Asn Glu Glu Glu Pro Asn Ala His Lys Val Ala
             40                  45                  50

AGC CCA CCC TCC GGA CCC GCA TAC CCC GAT GAT GTC CTG GAC TAT GGC            426
Ser Pro Pro Ser Gly Pro Ala Tyr Pro Asp Asp Val Leu Asp Tyr Gly
             55                  60                  65
```

| | | | | | | | | | | | | | | | | |
|---|---|---|---|---|---|---|---|---|---|---|---|---|---|---|---|---|
| CTC | AAG | CCA | TAC | AGC | CCC | CTT | GCT | AGT | CTC | TCT | GGC | GAG | CCC | CCC | GGC | 474 |
| Leu | Lys 70 | Pro | Tyr | Ser | Pro 75 | Leu | Ala | Ser | Leu | Ser 80 | Gly | Glu | Pro | Pro | Gly | |
| CGA | TTC | GGA | GAG | CCG | GAT | AGG | GTA | GGG | CCG | CAG | AAG | TTT | CTG | AGC | GCG | 522 |
| Arg 85 | Phe | Gly | Glu | Pro 90 | Asp | Arg | Val | Gly | Pro 95 | Gln | Lys | Phe | Leu | Ser | Ala 100 | |
| GCC | AAG | CCA | GCA | GGG | GCC | TCG | GGC | CTG | AGC | CCT | CGG | ATC | GAG | ATC | ACT | 570 |
| Ala | Lys | Pro | Ala | Gly 105 | Ala | Ser | Gly | Leu | Ser 110 | Pro | Arg | Ile | Glu | Ile 115 | Thr | |
| CCG | TCC | CAC | GAA | CTG | ATC | CAG | GCA | GTG | GGG | CCC | CTC | CGC | ATG | AGA | GAC | 618 |
| Pro | Ser | His | Glu 120 | Leu | Ile | Gln | Ala | Val 125 | Gly | Pro | Leu | Arg | Met 130 | Arg | Asp | |
| GCG | GGC | CTC | CTG | GTG | GAG | CAG | CCG | CCC | CTG | GCC | GGG | GTG | GCC | GCC | AGC | 666 |
| Ala | Gly | Leu 135 | Leu | Val | Glu | Gln | Pro 140 | Pro | Leu | Ala | Gly | Val 145 | Ala | Ala | Ser | |
| CCG | AGG | TTC | ACC | CTG | CCC | GTG | CCC | GGC | TTC | GAG | GGC | TAC | CGC | GAG | CCG | 714 |
| Pro | Arg 150 | Phe | Thr | Leu | Pro | Val 155 | Pro | Gly | Phe | Glu | Gly 160 | Tyr | Arg | Glu | Pro | |
| CTT | TGC | TTG | AGC | CCC | GCT | AGC | AGC | GGC | TCC | TCT | GCC | AGC | TTC | ATT | TCT | 762 |
| Leu 165 | Cys | Leu | Ser | Pro | Ala 170 | Ser | Ser | Gly | Ser | Ser 175 | Ala | Ser | Phe | Ile | Ser 180 | |
| GAC | ACC | TTC | TCC | CCC | TAC | ACC | TCG | CCC | TGC | GTC | TCG | CCC | AAT | AAC | GGC | 810 |
| Asp | Thr | Phe | Ser | Pro 185 | Tyr | Thr | Ser | Pro | Cys 190 | Val | Ser | Pro | Asn | Asn 195 | Gly | |
| GGG | CCC | GAC | GAC | CTG | TGT | CCG | CAG | TTT | CAA | AAC | ATC | CCT | GCT | CAT | TAT | 858 |
| Gly | Pro | Asp | Asp 200 | Leu | Cys | Pro | Gln | Phe 205 | Gln | Asn | Ile | Pro | Ala 210 | His | Tyr | |
| TCC | CCC | AGA | ACC | TCG | CCA | ATA | ATG | TCA | CCT | CGA | ACC | AGC | CTC | GCC | GAG | 906 |
| Ser | Pro | Arg 215 | Thr | Ser | Pro | Ile | Met 220 | Ser | Pro | Arg | Thr | Ser 225 | Leu | Ala | Glu | |
| GAC | AGC | TGC | CTG | GGC | CGC | CAC | TCG | CCC | GTG | CCC | CGT | CCG | GCC | TCC | CGC | 954 |
| Asp | Ser | Cys 230 | Leu | Gly | Arg | His | Ser 235 | Pro | Val | Pro | Arg | Pro 240 | Ala | Ser | Arg | |
| TCC | TCA | TCG | CCT | GGT | GCC | AAG | CGG | AGG | CAT | TCG | TGC | GCC | GAG | GCC | TTG | 1002 |
| Ser | Ser | Ser 245 | Pro | Gly | Ala | Lys | Arg 250 | Arg | His | Ser | Cys | Ala 255 | Glu | Ala | Leu 260 | |
| GTT | GCC | CTG | CCG | CCC | GGA | GCC | TCA | CCC | CAG | CGC | TCC | CGG | AGC | CCC | TCG | 1050 |
| Val | Ala | Leu | Pro | Pro 265 | Gly | Ala | Ser | Pro | Gln 270 | Arg | Ser | Arg | Ser | Pro 275 | Ser | |
| CCG | CAG | CCC | TCA | TCT | CAC | GTG | GCA | CCC | CAG | GAC | CAC | GGC | TCC | CCG | GCT | 1098 |
| Pro | Gln | Pro | Ser 280 | Ser | His | Val | Ala | Pro 285 | Gln | Asp | His | Gly | Ser 290 | Pro | Ala | |
| GGG | TAC | CCC | CCT | GTG | GCT | GGC | TCT | GCC | GTG | ATC | ATG | GAT | GCC | CTG | AAC | 1146 |
| Gly | Tyr | Pro | Pro 295 | Val | Ala | Gly | Ser | Ala 300 | Val | Ile | Met | Asp | Ala 305 | Leu | Asn | |
| AGC | CTC | GCC | ACG | GAC | TCG | CCT | TGT | GGG | ATC | CCC | CCC | AAG | ATG | TGG | AAG | 1194 |
| Ser | Leu | Ala 310 | Thr | Asp | Ser | Pro | Cys 315 | Gly | Ile | Pro | Pro | Lys 320 | Met | Trp | Lys | |
| ACC | AGC | CCT | GAC | CCC | TCG | CCG | GTG | TCT | GCC | GCC | CCA | TCC | AAG | GCC | GGC | 1242 |
| Thr | Ser 325 | Pro | Asp | Pro | Ser 330 | Pro | Val | Ser | Ala | Ala 335 | Pro | Ser | Lys | Ala | Gly 340 | |
| CTG | CCT | CGC | CAC | ATC | TAC | CCG | GCC | GTG | GAG | TTC | CTG | GGG | CCC | TGC | GAG | 1290 |
| Leu | Pro | Arg | His | Ile 345 | Tyr | Pro | Ala | Val | Glu 350 | Phe | Leu | Gly | Pro | Cys 355 | Glu | |
| CAG | GGC | GAG | AGG | AGA | AAC | TCG | GCT | CCA | GAA | TCC | ATC | CTG | CTG | GTT | CCG | 1338 |
| Gln | Gly | Glu | Arg 360 | Arg | Asn | Ser | Ala | Pro 365 | Glu | Ser | Ile | Leu | Leu 370 | Val | Pro | |
| CCC | ACT | TGG | CCC | AAG | CCG | CTG | GTG | CCT | GCC | ATT | CCC | ATC | TGC | AGC | ATC | 1386 |
| Pro | Thr | Trp 375 | Pro | Lys | Pro | Leu | Val 380 | Pro | Ala | Ile | Pro | Ile 385 | Cys | Ser | Ile | |

| | | | | | | | | | | | | | | | | |
|---|---|---|---|---|---|---|---|---|---|---|---|---|---|---|---|---|
| CCA | GTG | ACT | GCA | TCC | CTC | CCT | CCA | CTT | GAG | TGG | CCG | CTG | TCC | AGT | CAG | 1434 |
| Pro | Val | Thr | Ala | Ser | Leu | Pro | Pro | Leu | Glu | Trp | Pro | Leu | Ser | Ser | Gln | |
| | 390 | | | | 395 | | | | | 400 | | | | | | |
| TCA | GGC | TCT | TAC | GAG | CTG | CGG | ATC | GAG | GTG | CAG | CCC | AAG | CCA | CAT | CAC | 1482 |
| Ser | Gly | Ser | Tyr | Glu | Leu | Arg | Ile | Glu | Val | Gln | Pro | Lys | Pro | His | His | |
| 405 | | | | 410 | | | | | 415 | | | | | | 420 | |
| CGG | GCC | CAC | TAT | GAG | ACA | GAA | GGC | AGC | CGA | GGG | GCT | GTC | AAA | GCT | CCA | 1530 |
| Arg | Ala | His | Tyr | Glu | Thr | Glu | Gly | Ser | Arg | Gly | Ala | Val | Lys | Ala | Pro | |
| | | | | 425 | | | | | 430 | | | | | 435 | | |
| ACT | GGA | GGC | CAC | CCT | GTG | GTT | CAG | CTC | CAT | GGC | TAC | ATG | GAA | AAC | AAG | 1578 |
| Thr | Gly | Gly | His | Pro | Val | Val | Gln | Leu | His | Gly | Tyr | Met | Glu | Asn | Lys | |
| | | | 440 | | | | | 445 | | | | | 450 | | | |
| CCT | CTG | GGA | CTT | CAG | ATC | TTC | ATT | GGG | ACA | GCT | GAT | GAG | CGG | ATC | CTT | 1626 |
| Pro | Leu | Gly | Leu | Gln | Ile | Phe | Ile | Gly | Thr | Ala | Asp | Glu | Arg | Ile | Leu | |
| | | 455 | | | | | 460 | | | | | 465 | | | | |
| AAG | CCG | CAC | GCC | TTC | TAC | CAG | GTG | CAC | CGA | ATC | ACG | GGG | AAA | ACT | GTC | 1674 |
| Lys | Pro | His | Ala | Phe | Tyr | Gln | Val | His | Arg | Ile | Thr | Gly | Lys | Thr | Val | |
| | 470 | | | | | 475 | | | | | 480 | | | | | |
| ACC | ACC | ACC | AGC | TAT | GAG | AAG | ATA | GTG | GGC | AAC | ACC | AAA | GTC | CTG | GAG | 1722 |
| Thr | Thr | Thr | Ser | Tyr | Glu | Lys | Ile | Val | Gly | Asn | Thr | Lys | Val | Leu | Glu | |
| 485 | | | | | 490 | | | | | 495 | | | | | 500 | |
| ATA | CCC | TTG | GAG | CCC | AAA | AAC | AAC | ATG | AGG | GCA | ACC | ATC | GAC | TGT | GCG | 1770 |
| Ile | Pro | Leu | Glu | Pro | Lys | Asn | Asn | Met | Arg | Ala | Thr | Ile | Asp | Cys | Ala | |
| | | | | 505 | | | | | 510 | | | | | 515 | | |
| GGG | ATC | TTG | AAG | CTT | AGA | AAC | GCC | GAC | ATT | GAG | CTG | CGG | AAA | GGC | GAG | 1818 |
| Gly | Ile | Leu | Lys | Leu | Arg | Asn | Ala | Asp | Ile | Glu | Leu | Arg | Lys | Gly | Glu | |
| | | | 520 | | | | | 525 | | | | | 530 | | | |
| ACG | GAC | ATT | GGA | AGA | AAG | AAC | ACG | CGG | GTG | AGA | CTG | GTT | TTC | CGA | GTT | 1866 |
| Thr | Asp | Ile | Gly | Arg | Lys | Asn | Thr | Arg | Val | Arg | Leu | Val | Phe | Arg | Val | |
| | | 535 | | | | | 540 | | | | | 545 | | | | |
| CAC | ATC | CCA | GAG | TCC | AGT | GGC | AGA | ATC | GTC | TCT | TTA | CAG | ACT | GCA | TCT | 1914 |
| His | Ile | Pro | Glu | Ser | Ser | Gly | Arg | Ile | Val | Ser | Leu | Gln | Thr | Ala | Ser | |
| | 550 | | | | | 555 | | | | | 560 | | | | | |
| AAC | CCC | ATC | GAG | TGC | TCC | CAG | CGA | TCT | GCT | CAC | GAG | CTG | CCC | ATG | GTT | 1962 |
| Asn | Pro | Ile | Glu | Cys | Ser | Gln | Arg | Ser | Ala | His | Glu | Leu | Pro | Met | Val | |
| 565 | | | | | 570 | | | | | 575 | | | | | 580 | |
| GAA | AGA | CAA | GAC | ACA | GAC | AGC | TGC | CTG | GTC | TAT | GGC | GGC | CAG | CAA | ATG | 2010 |
| Glu | Arg | Gln | Asp | Thr | Asp | Ser | Cys | Leu | Val | Tyr | Gly | Gly | Gln | Gln | Met | |
| | | | | 585 | | | | | 590 | | | | | 595 | | |
| ATC | CTC | ACG | GGG | CAG | AAC | TTT | ACA | TCC | GAG | TCC | AAA | GTT | GTG | TTT | ACT | 2058 |
| Ile | Leu | Thr | Gly | Gln | Asn | Phe | Thr | Ser | Glu | Ser | Lys | Val | Val | Phe | Thr | |
| | | | 600 | | | | | 605 | | | | | 610 | | | |
| GAG | AAG | ACC | ACA | GAT | GGA | CAG | CAA | ATT | TGG | GAG | ATG | GAA | GCC | ACG | GTG | 2106 |
| Glu | Lys | Thr | Thr | Asp | Gly | Gln | Gln | Ile | Trp | Glu | Met | Glu | Ala | Thr | Val | |
| | | 615 | | | | | 620 | | | | | 625 | | | | |
| GAT | AAG | GAC | AAG | AGC | CAG | CCC | AAC | ATG | CTT | TTT | GTT | GAG | ATC | CCT | GAA | 2154 |
| Asp | Lys | Asp | Lys | Ser | Gln | Pro | Asn | Met | Leu | Phe | Val | Glu | Ile | Pro | Glu | |
| | 630 | | | | | 635 | | | | | 640 | | | | | |
| TAT | CGG | AAC | AAG | CAT | ATC | CGC | ACA | CCT | GTA | AAA | GTG | AAC | TTC | TAC | GTC | 2202 |
| Tyr | Arg | Asn | Lys | His | Ile | Arg | Thr | Pro | Val | Lys | Val | Asn | Phe | Tyr | Val | |
| 645 | | | | | 650 | | | | | 655 | | | | | 660 | |
| ATC | AAT | GGG | AAG | AGA | AAA | CGA | AGT | CAG | CCT | CAG | CAC | TTT | ACC | TAC | CAC | 2250 |
| Ile | Asn | Gly | Lys | Arg | Lys | Arg | Ser | Gln | Pro | Gln | His | Phe | Thr | Tyr | His | |
| | | | | 665 | | | | | 670 | | | | | 675 | | |
| CCA | GTC | CCA | GCC | ATC | AAG | ACG | GAG | CCC | ACG | GAT | GAA | TAT | GAC | CCC | ACT | 2298 |
| Pro | Val | Pro | Ala | Ile | Lys | Thr | Glu | Pro | Thr | Asp | Glu | Tyr | Asp | Pro | Thr | |
| | | | 680 | | | | | 685 | | | | | 690 | | | |
| CTG | ATC | TGC | AGC | CCC | ACC | CAT | GGA | GGC | CTG | GGG | AGC | CAG | CCT | TAC | TAC | 2346 |
| Leu | Ile | Cys | Ser | Pro | Thr | His | Gly | Gly | Leu | Gly | Ser | Gln | Pro | Tyr | Tyr | |
| | | 695 | | | | | 700 | | | | | 705 | | | | |

| | | | | | | | | | | | | | | | | |
|---|---|---|---|---|---|---|---|---|---|---|---|---|---|---|---|---|
| CCC | CAG | CAC | CCG | ATG | GTG | GCC | GAG | TCC | CCC | TCC | TGC | CTC | GTG | GCC | ACC | 2394 |
| Pro | Gln | His | Pro | Met | Val | Ala | Glu | Ser | Pro | Ser | Cys | Leu | Val | Ala | Thr | |
| | 710 | | | | 715 | | | | | 720 | | | | | | |
| ATG | GCT | CCC | TGC | CAG | CAG | TTC | CGC | ACG | GGG | CTC | TCA | TCC | CCT | GAC | GCC | 2442 |
| Met | Ala | Pro | Cys | Gln | Gln | Phe | Arg | Thr | Gly | Leu | Ser | Ser | Pro | Asp | Ala | |
| 725 | | | | 730 | | | | | 735 | | | | | 740 | | |
| CGC | TAC | CAG | CAA | CAG | AAC | CCA | GCG | GCC | GTA | CTC | TAC | CAG | CGG | AGC | AAG | 2490 |
| Arg | Tyr | Gln | Gln | Gln | Asn | Pro | Ala | Ala | Val | Leu | Tyr | Gln | Arg | Ser | Lys | |
| | | | | 745 | | | | | 750 | | | | | 755 | | |
| AGC | CTG | AGC | CCC | AGC | CTG | CTG | GGC | TAT | CAG | CAG | CCG | GCC | CTC | ATG | GCC | 2538 |
| Ser | Leu | Ser | Pro | Ser | Leu | Leu | Gly | Tyr | Gln | Gln | Pro | Ala | Leu | Met | Ala | |
| | | | 760 | | | | | 765 | | | | | 770 | | | |
| GCC | CCG | CTG | TCC | CTT | GCG | GAC | GCT | CAC | CGC | TCT | GTG | CTG | GTG | CAC | GCC | 2586 |
| Ala | Pro | Leu | Ser | Leu | Ala | Asp | Ala | His | Arg | Ser | Val | Leu | Val | His | Ala | |
| | | 775 | | | | | 780 | | | | | 785 | | | | |
| GGC | TCC | CAG | GGC | CAG | AGC | TCA | GCC | CTG | CTC | CAC | CCC | TCT | CCG | ACC | AAC | 2634 |
| Gly | Ser | Gln | Gly | Gln | Ser | Ser | Ala | Leu | Leu | His | Pro | Ser | Pro | Thr | Asn | |
| | 790 | | | | | 795 | | | | | 800 | | | | | |
| CAG | CAG | GCC | TCG | CCT | GTG | ATC | CAC | TAC | TCA | CCC | ACC | AAC | CAG | CAG | CTG | 2682 |
| Gln | Gln | Ala | Ser | Pro | Val | Ile | His | Tyr | Ser | Pro | Thr | Asn | Gln | Gln | Leu | |
| 805 | | | | | 810 | | | | | 815 | | | | | 820 | |
| CGC | TGC | GGA | AGC | CAC | CAG | GAG | TTC | CAG | CAC | ATC | ATG | TAC | TGC | GAG | AAT | 2730 |
| Arg | Cys | Gly | Ser | His | Gln | Glu | Phe | Gln | His | Ile | Met | Tyr | Cys | Glu | Asn | |
| | | | | 825 | | | | | 830 | | | | | 835 | | |
| TTC | GCA | CCA | GGC | ACC | ACC | AGA | CCT | GGC | CCG | CCC | CCG | GTC | AGT | CAA | GGT | 2778 |
| Phe | Ala | Pro | Gly | Thr | Thr | Arg | Pro | Gly | Pro | Pro | Pro | Val | Ser | Gln | Gly | |
| | | | 840 | | | | | 845 | | | | | 850 | | | |
| CAG | AGG | CTG | AGC | CCG | GGT | TCC | TAC | CCC | ACA | GTC | ATT | CAG | CAG | CAG | AAT | 2826 |
| Gln | Arg | Leu | Ser | Pro | Gly | Ser | Tyr | Pro | Thr | Val | Ile | Gln | Gln | Gln | Asn | |
| | | 855 | | | | | 860 | | | | | 865 | | | | |
| GCC | ACG | AGC | CAA | AGA | GCC | GCC | AAA | AAC | GGA | CCC | CCG | GTC | AGT | GAC | CAA | 2874 |
| Ala | Thr | Ser | Gln | Arg | Ala | Ala | Lys | Asn | Gly | Pro | Pro | Val | Ser | Asp | Gln | |
| | 870 | | | | | 875 | | | | | 880 | | | | | |
| AAG | GAA | GTA | TTA | CCT | GCG | GGG | GTG | ACC | ATT | AAA | CAG | GAG | CAG | AAC | TTG | 2922 |
| Lys | Glu | Val | Leu | Pro | Ala | Gly | Val | Thr | Ile | Lys | Gln | Glu | Gln | Asn | Leu | |
| 885 | | | | | 890 | | | | | 895 | | | | | 900 | |
| GAC | CAG | ACC | TAC | TTG | GAT | GAT | GAG | CTG | ATA | GAC | ACA | CAC | CTT | AGC | TGG | 2970 |
| Asp | Gln | Thr | Tyr | Leu | Asp | Asp | Glu | Leu | Ile | Asp | Thr | His | Leu | Ser | Trp | |
| | | | | 905 | | | | | 910 | | | | | 915 | | |
| ATA | CAA | AAC | ATA | TTA | TG AAACAGAATG ACTGTGATCT TTGATCCGAG | | | | | | | | | | | 3017 |
| Ile | Gln | Asn | Ile | Leu | | | | | | | | | | | | |
| | | | | 920 | | | | | | | | | | | | |

| | |
|---|---|
| AAATCAAAGT TAAAGTTAAT GAAATTATCA GGAAGGAGTT TTCAGGACCT CCTGCCAGAA | 3077 |
| ATCAGACGTA AAAGAAGCCA TTATAGCAAG ACACCTTCTG TATCTGACCC CTCGGAGCCC | 3137 |
| TCCACAGCCC CTCACCTTCT GTCTCCTTTC ATGTTCATCT CCCAGCCCGG AGTCCACACG | 3197 |
| CGGATCAATG TATGGGCACT AAGCGGACTC TCACTTAAGG AGCTCGCCAC CTCCCTCTAA | 3257 |
| ACACCAGAGA GAACTCTTCT TTTCGGTTTA TGTTTTAAAT CCCAGAGAGC ATCCTGGTTG | 3317 |
| ATCTTAATGG TGTTCCGTCC AAATAGTAAG CACCTGCTGA CCAAAAGCAC ATTCTACATG | 3377 |
| AGACAGGACA CTGGAACTCT CCTGAGAACA GAGTGACTGG AGCTTGGGGG GATGGACGGG | 3437 |
| GGACAGAAGA TGTGGGCACT GTGATTAAAC CCCAGCCCTT G | 3478 |

( 2 ) INFORMATION FOR SEQ ID NO:2:

( i ) SEQUENCE CHARACTERISTICS:
( A ) LENGTH: 921 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met  Asn  Ala  Pro  Glu  Arg  Gln  Pro  Gln  Pro  Asp  Gly  Gly  Asp  Ala  Pro
 1              5                        10                      15
Gly  His  Glu  Pro  Gly  Gly  Ser  Pro  Gln  Asp  Glu  Leu  Asp  Phe  Ser  Ile
              20                        25                      30
Leu  Phe  Asp  Tyr  Glu  Tyr  Leu  Asn  Pro  Asn  Glu  Glu  Glu  Pro  Asn  Ala
         35                        40                       45
His  Lys  Val  Ala  Ser  Pro  Pro  Ser  Gly  Pro  Ala  Tyr  Pro  Asp  Asp  Val
     50                       55                       60
Leu  Asp  Tyr  Gly  Leu  Lys  Pro  Tyr  Ser  Pro  Leu  Ala  Ser  Leu  Ser  Gly
65                       70                       75                      80
Glu  Pro  Pro  Gly  Arg  Phe  Gly  Glu  Pro  Asp  Arg  Val  Gly  Pro  Gln  Lys
                    85                       90                      95
Phe  Leu  Ser  Ala  Ala  Lys  Pro  Ala  Gly  Ala  Ser  Gly  Leu  Ser  Pro  Arg
               100                      105                     110
Ile  Glu  Ile  Thr  Pro  Ser  His  Glu  Leu  Ile  Gln  Ala  Val  Gly  Pro  Leu
               115                      120                     125
Arg  Met  Arg  Asp  Ala  Gly  Leu  Leu  Val  Glu  Gln  Pro  Pro  Leu  Ala  Gly
     130                      135                 140
Val  Ala  Ala  Ser  Pro  Arg  Phe  Thr  Leu  Pro  Val  Pro  Gly  Phe  Glu  Gly
145                      150                     155                     160
Tyr  Arg  Glu  Pro  Leu  Cys  Leu  Ser  Pro  Ala  Ser  Ser  Gly  Ser  Ser  Ala
               165                      170                     175
Ser  Phe  Ile  Ser  Asp  Thr  Phe  Ser  Pro  Tyr  Thr  Ser  Pro  Cys  Val  Ser
               180                      185                     190
Pro  Asn  Asn  Gly  Gly  Pro  Asp  Asp  Leu  Cys  Pro  Gln  Phe  Gln  Asn  Ile
          195                      200                      205
Pro  Ala  His  Tyr  Ser  Pro  Arg  Thr  Ser  Pro  Ile  Met  Ser  Pro  Arg  Thr
     210                      215                     220
Ser  Leu  Ala  Glu  Asp  Ser  Cys  Leu  Gly  Arg  His  Ser  Pro  Val  Pro  Arg
225                      230                     235                     240
Pro  Ala  Ser  Arg  Ser  Ser  Ser  Pro  Gly  Ala  Lys  Arg  Arg  His  Ser  Cys
               245                      250                     255
Ala  Glu  Ala  Leu  Val  Ala  Leu  Pro  Pro  Gly  Ala  Ser  Pro  Gln  Arg  Ser
               260                      265                     270
Arg  Ser  Pro  Ser  Pro  Gln  Pro  Ser  Ser  His  Val  Ala  Pro  Gln  Asp  His
          275                      280                      285
Gly  Ser  Pro  Ala  Gly  Tyr  Pro  Pro  Val  Ala  Gly  Ser  Ala  Val  Ile  Met
     290                      295                     300
Asp  Ala  Leu  Asn  Ser  Leu  Ala  Thr  Asp  Ser  Pro  Cys  Gly  Ile  Pro  Pro
305                      310                     315                     320
Lys  Met  Trp  Lys  Thr  Ser  Pro  Asp  Pro  Ser  Pro  Val  Ser  Ala  Ala  Pro
               325                      330                     335
Ser  Lys  Ala  Gly  Leu  Pro  Arg  His  Ile  Tyr  Pro  Ala  Val  Glu  Phe  Leu
               340                      345                     350
Gly  Pro  Cys  Glu  Gln  Gly  Glu  Arg  Arg  Asn  Ser  Ala  Pro  Glu  Ser  Ile
          355                      360                      365
Leu  Leu  Val  Pro  Pro  Thr  Trp  Pro  Lys  Pro  Leu  Val  Pro  Ala  Ile  Pro
     370                      375                     380
Ile  Cys  Ser  Ile  Pro  Val  Thr  Ala  Ser  Leu  Pro  Pro  Leu  Glu  Trp  Pro
385                      390                     395                     400
Leu  Ser  Ser  Gln  Ser  Gly  Ser  Tyr  Glu  Leu  Arg  Ile  Glu  Val  Gln  Pro
```

|   |   |   |   |   |   |   | 405 |   |   |   | 410 |   |   |   | 415 |   |   |
|---|---|---|---|---|---|---|---|---|---|---|---|---|---|---|---|---|---|

Lys Pro His His Arg Ala His Tyr Glu Thr Glu Gly Ser Arg Gly Ala
              420                   425              430

Val Lys Ala Pro Thr Gly Gly His Pro Val Val Gln Leu His Gly Tyr
        435              440                   445

Met Glu Asn Lys Pro Leu Gly Leu Gln Ile Phe Ile Gly Thr Ala Asp
    450              455                   460

Glu Arg Ile Leu Lys Pro His Ala Phe Tyr Gln Val His Arg Ile Thr
465              470                   475                   480

Gly Lys Thr Val Thr Thr Ser Tyr Glu Lys Ile Val Gly Asn Thr
                  485                   490                   495

Lys Val Leu Glu Ile Pro Leu Glu Pro Lys Asn Asn Met Arg Ala Thr
              500              505                   510

Ile Asp Cys Ala Gly Ile Leu Lys Leu Arg Asn Ala Asp Ile Glu Leu
          515              520                   525

Arg Lys Gly Glu Thr Asp Ile Gly Arg Lys Asn Thr Arg Val Arg Leu
        530              535                   540

Val Phe Arg Val His Ile Pro Glu Ser Ser Gly Arg Ile Val Ser Leu
545              550                   555                   560

Gln Thr Ala Ser Asn Pro Ile Glu Cys Ser Gln Arg Ser Ala His Glu
                565                   570                   575

Leu Pro Met Val Glu Arg Gln Asp Thr Asp Ser Cys Leu Val Tyr Gly
            580                   585                   590

Gly Gln Gln Met Ile Leu Thr Gly Gln Asn Phe Thr Ser Glu Ser Lys
        595                   600                   605

Val Val Phe Thr Glu Lys Thr Thr Asp Gly Gln Gln Ile Trp Glu Met
    610                   615                   620

Glu Ala Thr Val Asp Lys Asp Lys Ser Gln Pro Asn Met Leu Phe Val
625                   630                   635                   640

Glu Ile Pro Glu Tyr Arg Asn Lys His Ile Arg Thr Pro Val Lys Val
              645                   650                   655

Asn Phe Tyr Val Ile Asn Gly Lys Arg Lys Arg Ser Gln Pro Gln His
            660                   665                   670

Phe Thr Tyr His Pro Val Pro Ala Ile Lys Thr Glu Pro Thr Asp Glu
        675                   680                   685

Tyr Asp Pro Thr Leu Ile Cys Ser Pro Thr His Gly Gly Leu Gly Ser
    690                   695                   700

Gln Pro Tyr Tyr Pro Gln His Pro Met Val Ala Glu Ser Pro Ser Cys
705                   710                   715                   720

Leu Val Ala Thr Met Ala Pro Cys Gln Gln Phe Arg Thr Gly Leu Ser
              725                   730                   735

Ser Pro Asp Ala Arg Tyr Gln Gln Gln Asn Pro Ala Ala Val Leu Tyr
        740                   745                   750

Gln Arg Ser Lys Ser Leu Ser Pro Ser Leu Leu Gly Tyr Gln Gln Pro
        755                   760                   765

Ala Leu Met Ala Ala Pro Leu Ser Leu Ala Asp Ala His Arg Ser Val
    770                   775                   780

Leu Val His Ala Gly Ser Gly Gln Ser Ser Ala Leu Leu His Pro
785                   790                   795                   800

Ser Pro Thr Asn Gln Gln Ala Ser Pro Val Ile His Tyr Ser Pro Thr
              805                   810                   815

Asn Gln Gln Leu Arg Cys Gly Ser His Gln Glu Phe Gln His Ile Met
            820                   825                   830

|     |     |     |     |     |     |     |     |     |     |     |     |     |     |     |
| --- | --- | --- | --- | --- | --- | --- | --- | --- | --- | --- | --- | --- | --- | --- |
| Tyr | Cys | Glu | Asn | Phe | Ala | Pro | Gly | Thr | Arg | Pro | Gly | Pro | Pro | Pro |
|     | 835 |     |     |     |     |     | 840 |     |     |     | 845 |     |     |     |
| Val | Ser | Gln | Gly | Gln | Arg | Leu | Ser | Pro | Gly | Ser | Tyr | Pro | Thr | Val | Ile |
|     | 850 |     |     |     |     | 855 |     |     |     |     | 860 |     |     |     |
| Gln | Gln | Gln | Asn | Ala | Thr | Ser | Gln | Arg | Ala | Ala | Lys | Asn | Gly | Pro | Pro |
| 865 |     |     |     |     | 870 |     |     |     |     | 875 |     |     |     |     | 880 |
| Val | Ser | Asp | Gln | Lys | Glu | Val | Leu | Pro | Ala | Gly | Val | Thr | Ile | Lys | Gln |
|     |     |     |     | 885 |     |     |     |     | 890 |     |     |     |     | 895 |     |
| Glu | Gln | Asn | Leu | Asp | Gln | Thr | Tyr | Leu | Asp | Asp | Glu | Leu | Ile | Asp | Thr |
|     |     |     |     | 900 |     |     |     | 905 |     |     |     |     | 910 |     |     |
| His | Leu | Ser | Trp | Ile | Gln | Asn | Ile | Leu |
|     |     | 915 |     |     |     |     | 920 |     |

( 2 ) INFORMATION FOR SEQ ID NO:3:

( i ) SEQUENCE CHARACTERISTICS:
    ( A ) LENGTH: 2743 base pairs
    ( B ) TYPE: nucleic acid
    ( C ) STRANDEDNESS: double
    ( D ) TOPOLOGY: linear ( i i ) MOLECULE TYPE: cDNA ( i x ) FEATURE:
    ( A ) NAME/KEY: CDS
    ( B ) LOCATION: 240..2390

( x i ) SEQUENCE DESCRIPTION: SEQ ID NO:3:

```
GAATTCCGCA GGGCGCGGGC ACCGGGGCGC GGGCAGGGCT CGGAGCCACC GCGCAGGTCC    60

TAGGGCCGCG GCCGGGCCCC GCCACGCGCG CACACGCCCC TCGATGACTT TCCTCCGGGG   120

CGCGCGGCGC TGAGCCCGGG GCGAGGGCTG TCTTCCCGGA GACCCGACCC CGGCAGCGCG   180

GGGCGGCCAC TTCTCCTGTG CCTCCGCCCG CTGCTCCACT CCCCGCCGCC GCCGCGCGG   239
```

| ATG | CCA | AGC | ACC | AGC | TTT | CCA | GTC | CCT | TCC | AAG | TTT | CCA | CTT | GGC | CCT | 287 |
| --- | --- | --- | --- | --- | --- | --- | --- | --- | --- | --- | --- | --- | --- | --- | --- | --- |
| Met | Pro | Ser | Thr | Ser | Phe | Pro | Val | Pro | Ser | Lys | Phe | Pro | Leu | Gly | Pro |     |
|     |     |     | 925 |     |     |     |     | 930 |     |     |     |     | 935 |     |     |     |
| GCG | GCT | GCG | GTC | TTC | GGG | AGA | GGA | GAA | ACT | TTG | GGG | CCC | GCG | CCG | CGC | 335 |
| Ala | Ala | Ala | Val | Phe | Gly | Arg | Gly | Glu | Thr | Leu | Gly | Pro | Ala | Pro | Arg |     |
|     |     | 940 |     |     |     |     | 945 |     |     |     |     | 950 |     |     |     |     |
| GCC | GGC | GGC | ACC | ATG | AAG | TCA | GCG | GAG | GAA | GAA | CAC | TAT | GGC | TAT | GCA | 383 |
| Ala | Gly | Gly | Thr | Met | Lys | Ser | Ala | Glu | Glu | Glu | His | Tyr | Gly | Tyr | Ala |     |
|     | 955 |     |     |     |     | 960 |     |     |     |     | 965 |     |     |     |     |     |
| TCC | TCC | AAC | GTC | AGC | CCC | GCC | CTG | CCG | CTC | CCC | ACG | GCG | CAC | TCC | ACC | 431 |
| Ser | Ser | Asn | Val | Ser | Pro | Ala | Leu | Pro | Leu | Pro | Thr | Ala | His | Ser | Thr |     |
| 970 |     |     |     |     | 975 |     |     |     |     | 980 |     |     |     |     | 985 |     |
| CTG | CCG | GCC | CCG | TGC | CAC | AAC | CTT | CAG | ACC | TCC | ACA | CCG | GGC | ATC | ATC | 479 |
| Leu | Pro | Ala | Pro | Cys | His | Asn | Leu | Gln | Thr | Ser | Thr | Pro | Gly | Ile | Ile |     |
|     |     |     |     | 990 |     |     |     |     | 995 |     |     |     |     | 1000 |    |     |
| CCG | CCG | GCG | GAT | CAC | CCC | TCG | GGG | TAC | GGA | GCA | GCT | TTG | GAC | GGT | GGG | 527 |
| Pro | Pro | Ala | Asp | His | Pro | Ser | Gly | Tyr | Gly | Ala | Ala | Leu | Asp | Gly | Gly |     |
|     |     |     |     | 1005 |    |     |     | 1010 |    |     |     |     | 1015 |    |     |     |
| CCC | GCG | GGC | TAC | TTC | CTC | TCC | TCC | GGC | CAC | ACC | AGG | CCT | GAT | GGG | GCC | 575 |
| Pro | Ala | Gly | Tyr | Phe | Leu | Ser | Ser | Gly | His | Thr | Arg | Pro | Asp | Gly | Ala |     |
|     |     |     | 1020 |    |     |     |     | 1025 |    |     |     |     | 1030 |    |     |     |
| CCT | GCC | CTG | GAG | AGT | CCT | CGC | ATC | GAG | ATA | ACC | TCG | TGC | TTG | GGC | CTG | 623 |
| Pro | Ala | Leu | Glu | Ser | Pro | Arg | Ile | Glu | Ile | Thr | Ser | Cys | Leu | Gly | Leu |     |
|     |     |     | 1035 |    |     |     |     | 1040 |    |     |     |     | 1045 |    |     |     |
| TAC | CAC | AAC | AAT | AAC | CAG | TTT | TTC | CAC | GAT | GTG | GAG | GTG | GAA | GAC | GTC | 671 |
| Tyr | His | Asn | Asn | Asn | Gln | Phe | Phe | His | Asp | Val | Glu | Val | Glu | Asp | Val |     |
| 1050 |    |     |     |     | 1055 |    |     |     |     | 1060 |    |     |     |     | 1065 |    |
| CTC | CCT | AGC | TCC | AAA | CGG | TCC | CCC | TCC | ACG | GCC | ACG | CTG | AGT | CTG | CCC | 719 |

```
Leu Pro Ser Ser Lys Arg Ser Pro Ser Thr Ala Thr Leu Ser Leu Pro
            1070            1075                1080

AGC CTG GAG GCC TAC AGA GAC CCC TCG TGC CTG AGC CCG GCC AGC AGC      767
Ser Leu Glu Ala Tyr Arg Asp Pro Ser Cys Leu Ser Pro Ala Ser Ser
        1085                1090                1095

CTG TCC TCC CGG AGC TGC AAC TCA GAG GCC TCC TCC TAC GAG TCC AAC      815
Leu Ser Ser Arg Ser Cys Asn Ser Glu Ala Ser Ser Tyr Glu Ser Asn
            1100                1105                1110

TAC TCG TAC CCG TAC GCG TCC CCC CAG ACG TCG CCA TGG CAG TCT CCC      863
Tyr Ser Tyr Pro Tyr Ala Ser Pro Gln Thr Ser Pro Trp Gln Ser Pro
        1115                1120                1125

TGC GTG TCT CCC AAG ACC ACG GAC CCC GAG GAG GGC TTT CCC CGC GGG      911
Cys Val Ser Pro Lys Thr Thr Asp Pro Glu Glu Gly Phe Pro Arg Gly
1130                1135                1140                1145

CTG GGG GCC TGC ACA CTG CTG GGT TCC CCG CAG CAC TCC CCC TCC ACC      959
Leu Gly Ala Cys Thr Leu Leu Gly Ser Pro Gln His Ser Pro Ser Thr
            1150                1155                1160

TCG CCC CGC GCC AGC GTC ACT GAG GAG AGC TGG CTG GGT GCC CGC TCC     1007
Ser Pro Arg Ala Ser Val Thr Glu Glu Ser Trp Leu Gly Ala Arg Ser
        1165                1170                1175

TCC AGA CCC GCG TCC CCT TGC AAC AAG AGG AAG TAC AGC CTC AAC GGC     1055
Ser Arg Pro Ala Ser Pro Cys Asn Lys Arg Lys Tyr Ser Leu Asn Gly
            1180                1185                1190

CGG CAG CCG CCC TAC TCA CCC CAC CAC TCG CCC ACG CCG TCC CCG CAC     1103
Arg Gln Pro Pro Tyr Ser Pro His His Ser Pro Thr Pro Ser Pro His
        1195                1200                1205

GGC TCC CCG CGG GTC AGC GTG ACC GAC GAC TCG TGG TTG GGC AAC ACC     1151
Gly Ser Pro Arg Val Ser Val Thr Asp Asp Ser Trp Leu Gly Asn Thr
1210                1215                1220                1225

ACC CAG TAC ACC AGC TCG GCC ATC GTG GCC GCC ATC AAC GCG CTG ACC     1199
Thr Gln Tyr Thr Ser Ser Ala Ile Val Ala Ala Ile Asn Ala Leu Thr
            1230                1235                1240

ACC GAC AGC AGC CTG GAC CTG GGA GAT GGC GTC CCT GTC AAG TCC CGC     1247
Thr Asp Ser Ser Leu Asp Leu Gly Asp Gly Val Pro Val Lys Ser Arg
        1245                1250                1255

AAG ACC ACC CTG GAG CAG CCG CCC TCA GTG GCG CTC AAG GTG GAG CCC     1295
Lys Thr Thr Leu Glu Gln Pro Pro Ser Val Ala Leu Lys Val Glu Pro
            1260                1265                1270

GTC GGG GAG GAC CTG GGC AGC CCG CCG CCC CCG GCC GAC TTC GCG CCC     1343
Val Gly Glu Asp Leu Gly Ser Pro Pro Pro Pro Ala Asp Phe Ala Pro
        1275                1280                1285

GAA GAC TAC TCC TCT TTC CAG CAC ATC AGG AAG GGC GGC TTC TGC GAC     1391
Glu Asp Tyr Ser Ser Phe Gln His Ile Arg Lys Gly Gly Phe Cys Asp
1290                1295                1300                1305

CAG TAC CTG GCG GTG CCG CAG CAC CCC TAC CAG TGG GCG AAG CCC AAG     1439
Gln Tyr Leu Ala Val Pro Gln His Pro Tyr Gln Trp Ala Lys Pro Lys
            1310                1315                1320

CCC CTG TCC CCT ACG TCC TAC ATG AGC CCG ACC CTG CCC GCC CTG GAC     1487
Pro Leu Ser Pro Thr Ser Tyr Met Ser Pro Thr Leu Pro Ala Leu Asp
        1325                1330                1335

TGG CAG CTG CCG TCC CAC TCA GGC CCG TAT GAG CTT CGG ATT GAG GTG     1535
Trp Gln Leu Pro Ser His Ser Gly Pro Tyr Glu Leu Arg Ile Glu Val
            1340                1345                1350

CAG CCC AAG TCC CAC CAC CGA GCC CAC TAC GAG ACG GAG GGC AGC CGG     1583
Gln Pro Lys Ser His His Arg Ala His Tyr Glu Thr Glu Gly Ser Arg
        1355                1360                1365

GGG GCC GTG AAG GCG TCG GCC GGA GGA CAC CCC ATC GTG CAG CTG CAT     1631
Gly Ala Val Lys Ala Ser Ala Gly Gly His Pro Ile Val Gln Leu His
1370                1375                1380                1385

GGC TAC TTG GAG AAT GAG CCG CTG ATG CTG CAG CTT TTC ATT GGG ACG     1679
```

```
Gly Tyr Leu Glu Asn Glu Pro Leu Met Leu Gln Leu Phe Ile Gly Thr
            1390                1395                    1400

GCG GAC GAC CGC CTG CTG CGC CCG CAC GCC TTC TAC CAG GTG CAC CGC    1727
Ala Asp Asp Arg Leu Leu Arg Pro His Ala Phe Tyr Gln Val His Arg
        1405                1410                    1415

ATC ACA GGG AAG ACC GTG TCC ACC ACC AGC CAC GAG GCT ATC CTC TCC    1775
Ile Thr Gly Lys Thr Val Ser Thr Thr Ser His Glu Ala Ile Leu Ser
        1420                1425                1430

AAC ACC AAA GTC CTG GAG ATC CCA CTC CTG CCG GAG AAC AGC ATG CGA    1823
Asn Thr Lys Val Leu Glu Ile Pro Leu Leu Pro Glu Asn Ser Met Arg
        1435                1440                1445

GCC GTC ATT GAC TGT GCC GGA ATC CTG AAA CTC AGA AAC TCC GAC ATT    1871
Ala Val Ile Asp Cys Ala Gly Ile Leu Lys Leu Arg Asn Ser Asp Ile
1450                1455                1460                1465

GAA CTT CGG AAA GGA GAG ACG GAC ATC GGG AGG AAG AAC ACA CGG GTA    1919
Glu Leu Arg Lys Gly Glu Thr Asp Ile Gly Arg Lys Asn Thr Arg Val
        1470                1475                1480

CGG CTG GTG TTC CGC GTT CAC GTC CCG CAA CCC AGC GGC CGC ACG CTG    1967
Arg Leu Val Phe Arg Val His Val Pro Gln Pro Ser Gly Arg Thr Leu
        1485                1490                1495

TCC CTG CAG GTG GCC TCC AAC CCC ATC GAA TGC TCC CAG CGC TCA GCT    2015
Ser Leu Gln Val Ala Ser Asn Pro Ile Glu Cys Ser Gln Arg Ser Ala
        1500                1505                1510

CAG GAG CTG CCT CTG GTG GAG AAG CAG AGC ACG GAC AGC TAT CCG GTC    2063
Gln Glu Leu Pro Leu Val Glu Lys Gln Ser Thr Asp Ser Tyr Pro Val
        1515                1520                1525

GTG GGC GGG AAG AAG ATG GTC CTG TCT GGC CAC AAC TTC CTG CAG GAC    2111
Val Gly Gly Lys Lys Met Val Leu Ser Gly His Asn Phe Leu Gln Asp
1530                1535                1540                1545

TCC AAG GTC ATT TTC GTG GAG AAA GCC CCA GAT GGC CAC CAT GTC TGG    2159
Ser Lys Val Ile Phe Val Glu Lys Ala Pro Asp Gly His His Val Trp
        1550                1555                1560

GAG ATG GAA GCG AAA ACT GAC CGG GAC CTG TGC AAG CCG AAT TCT CTG    2207
Glu Met Glu Ala Lys Thr Asp Arg Asp Leu Cys Lys Pro Asn Ser Leu
        1565                1570                1575

GTG GTT GAG ATC CCG CCA TTT CGG AAT CAG AGG ATA ACC AGC CCC GTT    2255
Val Val Glu Ile Pro Pro Phe Arg Asn Gln Arg Ile Thr Ser Pro Val
        1580                1585                1590

CAC GTC AGT TTC TAC GTC TGC AAC GGG AAG AGA AAG CGA AGC CAG TAC    2303
His Val Ser Phe Tyr Val Cys Asn Gly Lys Arg Lys Arg Ser Gln Tyr
        1595                1600                1605

CAG CGT TTC ACC TAC CTT CCC GCC AAC GGT AAC GCC ATC TTT CTA ACC    2351
Gln Arg Phe Thr Tyr Leu Pro Ala Asn Gly Asn Ala Ile Phe Leu Thr
1610                1615                1620                1625

GTA AGC CGT GAA CAT GAG CGC GTG GGG TGC TTT TTC TAA AGACGCAGAA     2400
Val Ser Arg Glu His Glu Arg Val Gly Cys Phe Phe *
        1630                1635

ACGACGTCGC CGTAAAGCAG CGTGGCGTGT TGCACATTTA ACTGTGTGAT GTCCGTTAG   2460

TGAGACCGAG CCATCGATGC CCTGAAAAGG AAAGGAAAAG GGAAGCTTCG GATGCATTTT  2520

CCTTGATCCC TGTTGGGGGT GGGGGCGGG GGTTGCATAC TCAGATAGTC ACGGTTATTT   2580

TGCTTCTTGC GAATGTATAA CAGCCAAGGG GAAAACATGG CTCTTCTGCT CCAAAAAACT  2640

GAGGGGGTCC TGGTGTGCAT TTGCACCCTA AAGCTGCTTA CGGTGAAAAG GCAAATAGGT  2700

ATAGCTATTT TGCAGGCACC TTTAGGAATA AACTTTGCTT TTA                    2743
```

( 2 ) INFORMATION FOR SEQ ID NO:4:

( i ) SEQUENCE CHARACTERISTICS:
        ( A ) LENGTH: 716 amino acids ( B ) TYPE: amino acid
( D ) TOPOLOGY: linear ( i i ) MOLECULE TYPE: protein ( x i ) SEQUENCE DESCRIPTION: SEQ ID NO:4:

| Met | Pro | Ser | Thr | Ser | Phe | Pro | Val | Pro | Ser | Lys | Phe | Pro | Leu | Gly | Pro |
|---|---|---|---|---|---|---|---|---|---|---|---|---|---|---|---|
| 1 | | | | 5 | | | | | 10 | | | | | 15 | |
| Ala | Ala | Ala | Val | Phe | Gly | Arg | Gly | Glu | Thr | Leu | Gly | Pro | Ala | Pro | Arg |
| | | | 20 | | | | | 25 | | | | | 30 | | |
| Ala | Gly | Gly | Thr | Met | Lys | Ser | Ala | Glu | Glu | Glu | His | Tyr | Gly | Tyr | Ala |
| | | 35 | | | | | 40 | | | | | 45 | | | |
| Ser | Ser | Asn | Val | Ser | Pro | Ala | Leu | Pro | Leu | Pro | Thr | Ala | His | Ser | Thr |
| | 50 | | | | | 55 | | | | | 60 | | | | |
| Leu | Pro | Ala | Pro | Cys | His | Asn | Leu | Gln | Thr | Ser | Thr | Pro | Gly | Ile | Ile |
| 65 | | | | | 70 | | | | | 75 | | | | | 80 |
| Pro | Pro | Ala | Asp | His | Pro | Ser | Gly | Tyr | Gly | Ala | Ala | Leu | Asp | Gly | Gly |
| | | | | 85 | | | | | 90 | | | | | 95 | |
| Pro | Ala | Gly | Tyr | Phe | Leu | Ser | Ser | Gly | His | Thr | Arg | Pro | Asp | Gly | Ala |
| | | | | 100 | | | | | 105 | | | | | 110 | |
| Pro | Ala | Leu | Glu | Ser | Pro | Arg | Ile | Glu | Ile | Thr | Ser | Cys | Leu | Gly | Leu |
| | | | 115 | | | | | 120 | | | | | 125 | | |
| Tyr | His | Asn | Asn | Asn | Gln | Phe | Phe | His | Asp | Val | Glu | Val | Glu | Asp | Val |
| | | 130 | | | | | 135 | | | | | 140 | | | |
| Leu | Pro | Ser | Ser | Lys | Arg | Ser | Pro | Ser | Thr | Ala | Thr | Leu | Ser | Leu | Pro |
| 145 | | | | | 150 | | | | | 155 | | | | | 160 |
| Ser | Leu | Glu | Ala | Tyr | Arg | Asp | Pro | Ser | Cys | Leu | Ser | Pro | Ala | Ser | Ser |
| | | | | 165 | | | | | 170 | | | | | 175 | |
| Leu | Ser | Ser | Arg | Ser | Cys | Asn | Ser | Glu | Ala | Ser | Ser | Tyr | Glu | Ser | Asn |
| | | | 180 | | | | | 185 | | | | | 190 | | |
| Tyr | Ser | Tyr | Pro | Tyr | Ala | Ser | Pro | Gln | Thr | Ser | Pro | Trp | Gln | Ser | Pro |
| | | 195 | | | | | 200 | | | | | 205 | | | |
| Cys | Val | Ser | Pro | Lys | Thr | Thr | Asp | Pro | Glu | Glu | Gly | Phe | Pro | Arg | Gly |
| | 210 | | | | | 215 | | | | | 220 | | | | |
| Leu | Gly | Ala | Cys | Thr | Leu | Leu | Gly | Ser | Pro | Gln | His | Ser | Pro | Ser | Thr |
| 225 | | | | | 230 | | | | | 235 | | | | | 240 |
| Ser | Pro | Arg | Ala | Ser | Val | Thr | Glu | Glu | Ser | Trp | Leu | Gly | Ala | Arg | Ser |
| | | | | 245 | | | | | 250 | | | | | 255 | |
| Ser | Arg | Pro | Ala | Ser | Pro | Cys | Asn | Lys | Arg | Lys | Tyr | Ser | Leu | Asn | Gly |
| | | | 260 | | | | | 265 | | | | | 270 | | |
| Arg | Gln | Pro | Pro | Tyr | Ser | Pro | His | His | Ser | Pro | Thr | Pro | Ser | Pro | His |
| | | 275 | | | | | 280 | | | | | 285 | | | |
| Gly | Ser | Pro | Arg | Val | Ser | Val | Thr | Asp | Asp | Ser | Trp | Leu | Gly | Asn | Thr |
| | 290 | | | | | 295 | | | | | 300 | | | | |
| Thr | Gln | Tyr | Thr | Ser | Ser | Ala | Ile | Val | Ala | Ala | Ile | Asn | Ala | Leu | Thr |
| 305 | | | | | 310 | | | | | 315 | | | | | 320 |
| Thr | Asp | Ser | Ser | Leu | Asp | Leu | Gly | Asp | Gly | Val | Pro | Val | Lys | Ser | Arg |
| | | | | 325 | | | | | 330 | | | | | 335 | |
| Lys | Thr | Thr | Leu | Glu | Gln | Pro | Pro | Ser | Val | Ala | Leu | Lys | Val | Glu | Pro |
| | | | 340 | | | | | 345 | | | | | 350 | | |
| Val | Gly | Glu | Asp | Leu | Gly | Ser | Pro | Pro | Pro | Ala | Asp | Phe | Ala | Pro |
| | | 355 | | | | | 360 | | | | | 365 | | | |
| Glu | Asp | Tyr | Ser | Ser | Phe | Gln | His | Ile | Arg | Lys | Gly | Gly | Phe | Cys | Asp |
| | 370 | | | | | 375 | | | | | 380 | | | | |
| Gln | Tyr | Leu | Ala | Val | Pro | Gln | His | Pro | Tyr | Gln | Trp | Ala | Lys | Pro | Lys |

| | | 385 | | | | 390 | | | | 395 | | | | 400 | |
|---|---|---|---|---|---|---|---|---|---|---|---|---|---|---|---|

Pro  Leu  Ser  Pro  Thr  Ser  Tyr  Met  Ser  Pro  Thr  Leu  Pro  Ala  Leu  Asp
                   405                     410                    415

Trp  Gln  Leu  Pro  Ser  His  Ser  Gly  Pro  Tyr  Glu  Leu  Arg  Ile  Glu  Val
                   420                     425                    430

Gln  Pro  Lys  Ser  His  His  Arg  Ala  His  Tyr  Glu  Thr  Glu  Gly  Ser  Arg
               435                     440                    445

Gly  Ala  Val  Lys  Ala  Ser  Ala  Gly  Gly  His  Pro  Ile  Val  Gln  Leu  His
          450                     455                    460

Gly  Tyr  Leu  Glu  Asn  Glu  Pro  Leu  Met  Leu  Gln  Leu  Phe  Ile  Gly  Thr
465                     470                    475                    480

Ala  Asp  Asp  Arg  Leu  Leu  Arg  Pro  His  Ala  Phe  Tyr  Gln  Val  His  Arg
                    485                    490                    495

Ile  Thr  Gly  Lys  Thr  Val  Ser  Thr  Thr  Ser  His  Glu  Ala  Ile  Leu  Ser
               500                    505                    510

Asn  Thr  Lys  Val  Leu  Glu  Ile  Pro  Leu  Leu  Pro  Glu  Asn  Ser  Met  Arg
          515                    520                    525

Ala  Val  Ile  Asp  Cys  Ala  Gly  Ile  Leu  Lys  Leu  Arg  Asn  Ser  Asp  Ile
     530                    535                    540

Glu  Leu  Arg  Lys  Gly  Glu  Thr  Asp  Ile  Gly  Arg  Lys  Asn  Thr  Arg  Val
545                    550                    555                         560

Arg  Leu  Val  Phe  Arg  Val  His  Val  Pro  Gln  Pro  Ser  Gly  Arg  Thr  Leu
               565                    570                    575

Ser  Leu  Gln  Val  Ala  Ser  Asn  Pro  Ile  Glu  Cys  Ser  Gln  Arg  Ser  Ala
               580                    585                    590

Gln  Glu  Leu  Pro  Leu  Val  Glu  Lys  Gln  Ser  Thr  Asp  Ser  Tyr  Pro  Val
          595                    600                    605

Val  Gly  Gly  Lys  Lys  Met  Val  Leu  Ser  Gly  His  Asn  Phe  Leu  Gln  Asp
     610                    615                    620

Ser  Lys  Val  Ile  Phe  Val  Glu  Lys  Ala  Pro  Asp  Gly  His  His  Val  Trp
625                    630                    635                         640

Glu  Met  Glu  Ala  Lys  Thr  Asp  Arg  Asp  Leu  Cys  Lys  Pro  Asn  Ser  Leu
               645                    650                    655

Val  Val  Glu  Ile  Pro  Pro  Phe  Arg  Asn  Gln  Arg  Ile  Thr  Ser  Pro  Val
               660                    665                    670

His  Val  Ser  Phe  Tyr  Val  Cys  Asn  Gly  Lys  Arg  Lys  Arg  Ser  Gln  Tyr
          675                    680                    685

Gln  Arg  Phe  Thr  Tyr  Leu  Pro  Ala  Asn  Gly  Asn  Ala  Ile  Phe  Leu  Thr
     690                    695                    700

Val  Ser  Arg  Glu  His  Glu  Arg  Val  Gly  Cys  Phe  Phe
705                    710                    715

( 2 ) INFORMATION FOR SEQ ID NO:5:

( i ) SEQUENCE CHARACTERISTICS:
        ( A ) LENGTH: 2881 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 142..2850

( x i ) SEQUENCE DESCRIPTION: SEQ ID NO:5:

GCTTCTGGAG    GGAGGCGGCA    GCGACGGAGG    AGGGGGCTTC    TCAGAGAAAG    GGAGGGAGGG    60

| | | | | | | | | | | |
|---|---|---|---|---|---|---|---|---|---|---|
| AGCCACCCGG | GTGAAGATAC | AGCAGCCTCC | TGAACTCCCC | CCTCCCACCC | AGGCCGGGAC | | | | | 120 |

| | | | | | | | | | | | | |
|---|---|---|---|---|---|---|---|---|---|---|---|---|
| CTGGGGGCTC | CTGCCGGATC | C | ATG | GGG | GCG | GCC | AGC | TGC | GAG | GAT | GAG | GAG | 171 |
| | | | Met | Gly | Ala | Ala | Ser | Cys | Glu | Asp | Glu | Glu |
| | | | | 720 | | | | | 725 | | | |

| CTG | GAA | TTT | AAG | CTG | GTG | TTC | GGG | GAG | GAA | AAG | GAG | GCC | CCC | CCG | CTG | 219 |
|---|---|---|---|---|---|---|---|---|---|---|---|---|---|---|---|---|
| Leu | Glu | Phe | Lys | Leu | Val | Phe | Gly | Glu | Glu | Lys | Glu | Ala | Pro | Pro | Leu |
| | | 730 | | | | | 735 | | | | | 740 | | | |

| GGC | GCG | GGG | GGA | TTG | GGG | GAA | GAA | CTG | GAC | TCA | GAG | GAT | GCC | CCG | CCA | 267 |
|---|---|---|---|---|---|---|---|---|---|---|---|---|---|---|---|---|
| Gly | Ala | Gly | Gly | Leu | Gly | Glu | Glu | Leu | Asp | Ser | Glu | Asp | Ala | Pro | Pro |
| | 745 | | | | | 750 | | | | | 755 | | | | |

| TGC | TGC | CGT | CTG | GCC | TTG | GGA | GAG | CCC | CCT | CCC | TAT | GGC | GCT | GCA | CCT | 315 |
|---|---|---|---|---|---|---|---|---|---|---|---|---|---|---|---|---|
| Cys | Cys | Arg | Leu | Ala | Leu | Gly | Glu | Pro | Pro | Pro | Tyr | Gly | Ala | Ala | Pro |
| 760 | | | | | 765 | | | | | 770 | | | | | 775 |

| ATC | GGT | ATT | CCC | CGA | CCT | CCA | CCC | CCT | CGG | CCT | GGC | ATG | CAT | TCG | CCA | 363 |
|---|---|---|---|---|---|---|---|---|---|---|---|---|---|---|---|---|
| Ile | Gly | Ile | Pro | Arg | Pro | Pro | Pro | Pro | Arg | Pro | Gly | Met | His | Ser | Pro |
| | | | | 780 | | | | | 785 | | | | | 790 | |

| CCG | CCG | CGA | CCA | GCC | CCC | TCA | CCT | GGC | ACC | TGG | GAG | AGC | CAG | CCC | GCC | 411 |
|---|---|---|---|---|---|---|---|---|---|---|---|---|---|---|---|---|
| Pro | Pro | Arg | Pro | Ala | Pro | Ser | Pro | Gly | Thr | Trp | Glu | Ser | Gln | Pro | Ala |
| | | | 795 | | | | | 800 | | | | | 805 | | |

| AGG | TCG | GTG | AGG | CTG | GGA | GGA | CCA | GGA | GGG | GGT | GCT | GGG | GGT | GCT | GGG | 459 |
|---|---|---|---|---|---|---|---|---|---|---|---|---|---|---|---|---|
| Arg | Ser | Val | Arg | Leu | Gly | Gly | Pro | Gly | Gly | Gly | Ala | Gly | Gly | Ala | Gly |
| | | 810 | | | | | 815 | | | | | 820 | | | |

| GGT | GGC | CGT | GTT | CTC | GAG | TGT | CCC | AGC | ATC | CGC | ATC | ACC | TCC | ATC | TCT | 507 |
|---|---|---|---|---|---|---|---|---|---|---|---|---|---|---|---|---|
| Gly | Gly | Arg | Val | Leu | Glu | Cys | Pro | Ser | Ile | Arg | Ile | Thr | Ser | Ile | Ser |
| 825 | | | | | 830 | | | | | 835 | | | | | |

| CCC | ACG | CCG | GAG | CCG | CCA | GCA | GCG | CTG | GAG | GAC | AAC | CCT | GAT | GCC | TGG | 555 |
|---|---|---|---|---|---|---|---|---|---|---|---|---|---|---|---|---|
| Pro | Thr | Pro | Glu | Pro | Pro | Ala | Ala | Leu | Glu | Asp | Asn | Pro | Asp | Ala | Trp |
| 840 | | | | | 845 | | | | | 850 | | | | | 855 |

| GGG | GAC | GGC | TCT | CCT | AGA | GAT | TAC | CCC | CCA | CCA | GAA | GGC | TTT | GGG | GGC | 603 |
|---|---|---|---|---|---|---|---|---|---|---|---|---|---|---|---|---|
| Gly | Asp | Gly | Ser | Pro | Arg | Asp | Tyr | Pro | Pro | Pro | Glu | Gly | Phe | Gly | Gly |
| | | | | 860 | | | | | 865 | | | | | 870 | |

| TAC | AGA | GAA | GCA | GGG | GCC | CAG | GGT | GGG | GGG | GCC | TTC | TTC | AGC | CCA | AGC | 651 |
|---|---|---|---|---|---|---|---|---|---|---|---|---|---|---|---|---|
| Tyr | Arg | Glu | Ala | Gly | Ala | Gln | Gly | Gly | Gly | Ala | Phe | Phe | Ser | Pro | Ser |
| | | | 875 | | | | | 880 | | | | | 885 | | |

| CCT | GGC | AGC | AGC | AGC | CTG | TCC | TCG | TGG | AGC | TTC | TTC | TCC | GAT | GCC | TCT | 699 |
|---|---|---|---|---|---|---|---|---|---|---|---|---|---|---|---|---|
| Pro | Gly | Ser | Ser | Ser | Leu | Ser | Ser | Trp | Ser | Phe | Phe | Ser | Asp | Ala | Ser |
| | | 890 | | | | | 895 | | | | | 900 | | | |

| GAC | GAG | GCA | GCC | CTG | TAT | GCA | GCC | TGC | GAC | GAG | GTG | GAG | TCT | GAG | CTA | 747 |
|---|---|---|---|---|---|---|---|---|---|---|---|---|---|---|---|---|
| Asp | Glu | Ala | Ala | Leu | Tyr | Ala | Ala | Cys | Asp | Glu | Val | Glu | Ser | Glu | Leu |
| | 905 | | | | | 910 | | | | | 915 | | | | |

| AAT | GAG | GCG | GCC | TCC | CGC | TTT | GGC | CTG | GGC | TCC | CCG | CTG | CCC | TCG | CCC | 795 |
|---|---|---|---|---|---|---|---|---|---|---|---|---|---|---|---|---|
| Asn | Glu | Ala | Ala | Ser | Arg | Phe | Gly | Leu | Gly | Ser | Pro | Leu | Pro | Ser | Pro |
| 920 | | | | | 925 | | | | | 930 | | | | | 935 |

| CGG | GCC | TCC | CCT | CGG | CCA | TGG | ACC | CCC | GAA | GAT | CCC | TGG | AGC | CTG | TAT | 843 |
|---|---|---|---|---|---|---|---|---|---|---|---|---|---|---|---|---|
| Arg | Ala | Ser | Pro | Arg | Pro | Trp | Thr | Pro | Glu | Asp | Pro | Trp | Ser | Leu | Tyr |
| | | | | 940 | | | | | 945 | | | | | 950 | |

| GGT | CCA | AGC | CCC | GGA | GGC | CGA | GGG | CCA | GAG | GAT | AGC | TGG | CTA | CTC | CTC | 891 |
|---|---|---|---|---|---|---|---|---|---|---|---|---|---|---|---|---|
| Gly | Pro | Ser | Pro | Gly | Gly | Arg | Gly | Pro | Glu | Asp | Ser | Trp | Leu | Leu | Leu |
| | | | 955 | | | | | 960 | | | | | 965 | | |

| AGT | GCT | CCT | GGG | CCC | ACC | CCA | GCC | TCC | CCG | CGG | CCT | GCC | TCT | CCA | TGT | 939 |
|---|---|---|---|---|---|---|---|---|---|---|---|---|---|---|---|---|
| Ser | Ala | Pro | Gly | Pro | Thr | Pro | Ala | Ser | Pro | Arg | Pro | Ala | Ser | Pro | Cys |
| | | 970 | | | | | 975 | | | | | 980 | | | |

| GGC | AAG | CGG | CGC | TAT | TCC | AGC | TCG | GGA | ACC | CCA | TCT | TCA | GCC | TCC | CCA | 987 |
|---|---|---|---|---|---|---|---|---|---|---|---|---|---|---|---|---|
| Gly | Lys | Arg | Arg | Tyr | Ser | Ser | Ser | Gly | Thr | Pro | Ser | Ser | Ala | Ser | Pro |
| 985 | | | | | 990 | | | | | 995 | | | | | |

| GCT | CTG | TCC | CGC | CGT | GGC | AGC | CTG | GGG | GAA | GAG | GGG | TCT | GAG | CCA | CCT | 1035 |
|---|---|---|---|---|---|---|---|---|---|---|---|---|---|---|---|---|
| Ala | Leu | Ser | Arg | Arg | Gly | Ser | Leu | Gly | Glu | Glu | Gly | Ser | Glu | Pro | Pro |
| 1000 | | | | | 1005 | | | | | 1010 | | | | | 1015 |

| CCA | CCA | CCC | CCA | TTG | CCT | CTG | GCC | CGG | GAC | CCG | GGC | TCC | CCT | GGT | CCC | 1083 |
|---|---|---|---|---|---|---|---|---|---|---|---|---|---|---|---|---|

```
                Pro  Pro  Pro  Pro  Leu  Pro  Leu  Ala  Arg  Asp  Pro  Gly  Ser  Pro  Gly  Pro
                          1020                     1025                          1030

TTT  GAC  TAT  GTG  GGG  GCC  CCA  CCA  GCT  GAG  AGC  ATC  CCT  CAG  AAG  ACA                    1131
Phe  Asp  Tyr  Val  Gly  Ala  Pro  Pro  Ala  Glu  Ser  Ile  Pro  Gln  Lys  Thr
               1035                    1040                    1045

CGG  CGG  ACT  TCC  AGC  GAG  CAG  GCA  GTG  GCT  CTG  CCT  CGG  TCT  GAG  GAG                    1179
Arg  Arg  Thr  Ser  Ser  Glu  Gln  Ala  Val  Ala  Leu  Pro  Arg  Ser  Glu  Glu
          1050                    1055                    1060

CCT  GCC  TCA  TGC  AAT  GGG  AAG  CTG  CCC  TTG  GGA  GCA  GAG  GAG  TCT  GTG                    1227
Pro  Ala  Ser  Cys  Asn  Gly  Lys  Leu  Pro  Leu  Gly  Ala  Glu  Glu  Ser  Val
          1065                    1070                    1075

GCT  CCT  CCA  GGA  GGT  TCC  CGG  AAG  GAG  GTG  GCT  GGC  ATG  GAC  TAC  CTG                    1275
Ala  Pro  Pro  Gly  Gly  Ser  Arg  Lys  Glu  Val  Ala  Gly  Met  Asp  Tyr  Leu
1080                    1085                    1090                    1095

GCA  GTG  CCC  TCC  CCA  CTC  GCT  TGG  TCC  AAG  GCC  CGG  ATT  GGG  GGA  CAC                    1323
Ala  Val  Pro  Ser  Pro  Leu  Ala  Trp  Ser  Lys  Ala  Arg  Ile  Gly  Gly  His
               1100                    1105                    1110

AGC  CCT  ATC  TTC  AGG  ACC  TCT  GCC  CTA  CCC  CCA  CTG  GAC  TGG  CCT  CTG                    1371
Ser  Pro  Ile  Phe  Arg  Thr  Ser  Ala  Leu  Pro  Pro  Leu  Asp  Trp  Pro  Leu
          1115                    1120                    1125

CCC  AGC  CAA  TAT  GAG  CAG  CTG  GAG  CTG  AGG  ATC  GAG  GTA  CAG  CCT  AGA                    1419
Pro  Ser  Gln  Tyr  Glu  Gln  Leu  Glu  Leu  Arg  Ile  Glu  Val  Gln  Pro  Arg
          1130                    1135                    1140

GCC  CAC  CAC  CGG  GCC  CAC  TAT  GAG  ACA  GAA  GGC  AGC  CGT  GGA  GCT  GTC                    1467
Ala  His  His  Arg  Ala  His  Tyr  Glu  Thr  Glu  Gly  Ser  Arg  Gly  Ala  Val
          1145                    1150                    1155

AAA  GCT  GCC  CCT  GGC  GGT  CAC  CCC  GTA  GTC  AAG  CTC  CTA  GGC  TAC  AGT                    1515
Lys  Ala  Ala  Pro  Gly  Gly  His  Pro  Val  Val  Lys  Leu  Leu  Gly  Tyr  Ser
1160                    1165                    1170                    1175

GAG  AAG  CCA  CTG  ACC  CTA  CAG  ATG  TTC  ATC  GGC  ACT  GCA  GAT  GAA  AGG                    1563
Glu  Lys  Pro  Leu  Thr  Leu  Gln  Met  Phe  Ile  Gly  Thr  Ala  Asp  Glu  Arg
               1180                    1185                    1190

AAC  CTG  CGG  CCT  CAT  GCC  TTC  TAT  CAG  GTG  CAC  CGT  ATC  ACA  GGC  AAG                    1611
Asn  Leu  Arg  Pro  His  Ala  Phe  Tyr  Gln  Val  His  Arg  Ile  Thr  Gly  Lys
          1195                    1200                    1205

ATG  GTG  GCC  ACG  GCC  AGC  TAT  GAA  GCC  GTA  GTC  AGT  GGC  ACC  AAG  GTG                    1659
Met  Val  Ala  Thr  Ala  Ser  Tyr  Glu  Ala  Val  Val  Ser  Gly  Thr  Lys  Val
          1210                    1215                    1220

TTG  GAG  ATG  ACT  CTG  CTG  CCT  GAG  AAC  AAC  ATG  GCG  GCC  AAC  ATT  GAC                    1707
Leu  Glu  Met  Thr  Leu  Leu  Pro  Glu  Asn  Asn  Met  Ala  Ala  Asn  Ile  Asp
          1225                    1230                    1235

TGC  GCG  GGA  ATC  CTG  AAG  CTT  CGG  AAT  TCA  GAC  ATT  GAG  CTT  CGG  AAG                    1755
Cys  Ala  Gly  Ile  Leu  Lys  Leu  Arg  Asn  Ser  Asp  Ile  Glu  Leu  Arg  Lys
1240                    1245                    1250                    1255

GGT  GAG  ACG  GAC  ATC  GGG  CGC  AAA  AAC  ACA  CGT  GTA  CGG  CTG  GTG  TTC                    1803
Gly  Glu  Thr  Asp  Ile  Gly  Arg  Lys  Asn  Thr  Arg  Val  Arg  Leu  Val  Phe
               1260                    1265                    1270

CGG  GTA  CAC  GTG  CCC  CAG  GGC  GGC  GGG  AAG  GTC  GTC  TCA  GTA  CAG  GCA                    1851
Arg  Val  His  Val  Pro  Gln  Gly  Gly  Gly  Lys  Val  Val  Ser  Val  Gln  Ala
          1275                    1280                    1285

GCA  TCG  GTG  CCC  ATC  GAG  TGC  TCC  CAG  CGC  TCA  GCC  CAG  GAG  CTG  CCC                    1899
Ala  Ser  Val  Pro  Ile  Glu  Cys  Ser  Gln  Arg  Ser  Ala  Gln  Glu  Leu  Pro
          1290                    1295                    1300

CAG  GTG  GAG  GCC  TAC  AGC  CCC  AGT  GCC  TGC  TCT  GTG  AGA  GGA  GGC  GAG                    1947
Gln  Val  Glu  Ala  Tyr  Ser  Pro  Ser  Ala  Cys  Ser  Val  Arg  Gly  Gly  Glu
          1305                    1310                    1315

GAA  CTG  GTA  CTG  ACC  GGC  TCC  AAC  TTC  CTG  CCA  GAC  TCC  AAG  GTG  GTG                    1995
Glu  Leu  Val  Leu  Thr  Gly  Ser  Asn  Phe  Leu  Pro  Asp  Ser  Lys  Val  Val
1320                    1325                    1330                    1335

TTC  ATT  GAG  AGG  GGT  CCT  GAT  GGG  AAG  CTG  CAA  TGG  GAG  GAG  GAG  GCC                    2043
```

```
Phe Ile Glu Arg Gly Pro Asp Gly Lys Leu Gln Trp Glu Glu Ala
         1340              1345                  1350

ACA GTG AAC CGA CTG CAG AGC AAC GAG GTG ACG CTG ACC CTG ACT GTC      2091
Thr Val Asn Arg Leu Gln Ser Asn Glu Val Thr Leu Thr Leu Thr Val
             1355             1360             1365

CCC GAG TAC AGC AAC AAG AGG GTT TCC CGG CCA GTC CAG GTC TAC TTT      2139
Pro Glu Tyr Ser Asn Lys Arg Val Ser Arg Pro Val Gln Val Tyr Phe
         1370             1375             1380

TAT GTC TCC AAT GGG CGG AGG AAA CGC AGT CCT ACC CAG AGT TTC AGG      2187
Tyr Val Ser Asn Gly Arg Arg Lys Arg Ser Pro Thr Gln Ser Phe Arg
         1385             1390             1395

TTT CTG CCT GTG ATC TGC AAA GAG GAG CCC CTA CCG GAC TCA TCT CTG      2235
Phe Leu Pro Val Ile Cys Lys Glu Glu Pro Leu Pro Asp Ser Ser Leu
1400             1405             1410             1415

CGG GGT TTC CCT TCA GCA TCG GCA ACC CCC TTT GGC ACT GAC ATG GAC      2283
Arg Gly Phe Pro Ser Ala Ser Ala Thr Pro Phe Gly Thr Asp Met Asp
             1420             1425             1430

TTC TCA CCA CCC AGG CCC CCC TAC CCC TCC TAT CCC CAT GAA GAC CCT      2331
Phe Ser Pro Pro Arg Pro Pro Tyr Pro Ser Tyr Pro His Glu Asp Pro
             1435             1440             1445

GCT TGC GAA ACT CCT TAC CTA TCA GAA GGC TTC GGC TAT GGC ATG CCC      2379
Ala Cys Glu Thr Pro Tyr Leu Ser Glu Gly Phe Gly Tyr Gly Met Pro
             1450             1455             1460

CCT CTG TAC CCC CAG ACG GGG CCC CCA CCA TCC TAC AGA CCG GGC CTG      2427
Pro Leu Tyr Pro Gln Thr Gly Pro Pro Pro Ser Tyr Arg Pro Gly Leu
         1465             1470             1475

CGG ATG TTC CCT GAG ACT AGG GGT ACC ACA GGT TGT GCC CAA CCA CCT      2475
Arg Met Phe Pro Glu Thr Arg Gly Thr Thr Gly Cys Ala Gln Pro Pro
1480             1485             1490             1495

GCA GTT TCC TTC CTT CCC CGC CCC TTC CCT AGT GAC CCG TAT GGA GGG      2523
Ala Val Ser Phe Leu Pro Arg Pro Phe Pro Ser Asp Pro Tyr Gly Gly
             1500             1505             1510

CGG GGC TCC TCT TTC CCC CTG GGG CTG CCA TTC TCT CCG CCA GCC CCC      2571
Arg Gly Ser Ser Phe Pro Leu Gly Leu Pro Phe Ser Pro Pro Ala Pro
             1515             1520             1525

TTT CGG CCG CCT CCT CTT CCT GCA TCC CCA CCG CTT GAA GGC CCC TTC      2619
Phe Arg Pro Pro Pro Leu Pro Ala Ser Pro Pro Leu Glu Gly Pro Phe
         1530             1535             1540

CCT TCC CAG AGT GAT GTG CAT CCC CTA CCT GCT GAG GGA TAC AAT AAG      2667
Pro Ser Gln Ser Asp Val His Pro Leu Pro Ala Glu Gly Tyr Asn Lys
         1545             1550             1555

GTA GGG CCA GGC TAT GGC CCT GGG GAG GGG GCT CCG GAG CAG GAG AAA      2715
Val Gly Pro Gly Tyr Gly Pro Gly Glu Gly Ala Pro Glu Gln Glu Lys
1560             1565             1570             1575

TCC AGG GGT GGC TAC AGC AGC GGC TTT CGA GAC AGT GTC CCT ATC CAG      2763
Ser Arg Gly Gly Tyr Ser Ser Gly Phe Arg Asp Ser Val Pro Ile Gln
         1580             1585             1590

GGT ATC ACG CTG GAG GAA GTG AGT GAG ATC ATT GGC CGA GAC CTG AGT      2811
Gly Ile Thr Leu Glu Glu Val Ser Glu Ile Ile Gly Arg Asp Leu Ser
             1595             1600             1605

GGC TTC CCT GCA CCT CCT GGA GAA GAG CCT CCT GCC TGA ACCACGTGAA       2860
Gly Phe Pro Ala Pro Pro Gly Glu Glu Pro Pro Ala  *
1610             1615             1620

CTGTCATCAC CTGGCAACCC C                                              2881
```

( 2 ) INFORMATION FOR SEQ ID NO:6:

( i ) SEQUENCE CHARACTERISTICS:
        ( A ) LENGTH: 902 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Met | Gly | Ala | Ala | Ser | Cys | Glu | Asp | Glu | Glu | Leu | Glu | Phe | Lys | Leu | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Phe | Gly | Glu | Glu | Lys | Glu | Ala | Pro | Pro | Leu | Gly | Ala | Gly | Gly | Leu | Gly |
|     |     |     | 20  |     |     |     |     | 25  |     |     |     |     | 30  |     |     |
| Glu | Glu | Leu | Asp | Ser | Glu | Asp | Ala | Pro | Pro | Cys | Cys | Arg | Leu | Ala | Leu |
|     |     |     | 35  |     |     |     | 40  |     |     |     |     | 45  |     |     |     |
| Gly | Glu | Pro | Pro | Pro | Tyr | Gly | Ala | Ala | Pro | Ile | Gly | Ile | Pro | Arg | Pro |
|     | 50  |     |     |     |     | 55  |     |     |     |     | 60  |     |     |     |     |
| Pro | Pro | Pro | Arg | Pro | Gly | Met | His | Ser | Pro | Pro | Pro | Arg | Pro | Ala | Pro |
| 65  |     |     |     |     | 70  |     |     |     |     | 75  |     |     |     |     | 80  |
| Ser | Pro | Gly | Thr | Trp | Glu | Ser | Gln | Pro | Ala | Arg | Ser | Val | Arg | Leu | Gly |
|     |     |     |     | 85  |     |     |     |     | 90  |     |     |     |     | 95  |     |
| Gly | Pro | Gly | Gly | Gly | Ala | Gly | Gly | Ala | Gly | Gly | Arg | Val | Leu | Glu |     |
|     |     |     | 100 |     |     |     |     | 105 |     |     |     |     | 110 |     |     |
| Cys | Pro | Ser | Ile | Arg | Ile | Thr | Ser | Ile | Ser | Pro | Thr | Pro | Glu | Pro | Pro |
|     |     | 115 |     |     |     |     | 120 |     |     |     |     | 125 |     |     |     |
| Ala | Ala | Leu | Glu | Asp | Asn | Pro | Asp | Ala | Trp | Gly | Asp | Gly | Ser | Pro | Arg |
|     | 130 |     |     |     |     | 135 |     |     |     |     | 140 |     |     |     |     |
| Asp | Tyr | Pro | Pro | Pro | Glu | Gly | Phe | Gly | Gly | Tyr | Arg | Glu | Ala | Gly | Ala |
| 145 |     |     |     |     | 150 |     |     |     |     | 155 |     |     |     |     | 160 |
| Gln | Gly | Gly | Gly | Ala | Phe | Phe | Ser | Pro | Ser | Pro | Gly | Ser | Ser | Ser | Leu |
|     |     |     |     | 165 |     |     |     |     | 170 |     |     |     |     | 175 |     |
| Ser | Ser | Trp | Ser | Phe | Phe | Ser | Asp | Ala | Ser | Asp | Glu | Ala | Ala | Leu | Tyr |
|     |     |     | 180 |     |     |     |     | 185 |     |     |     |     | 190 |     |     |
| Ala | Ala | Cys | Asp | Glu | Val | Glu | Ser | Glu | Leu | Asn | Glu | Ala | Ala | Ser | Arg |
|     |     | 195 |     |     |     |     | 200 |     |     |     |     | 205 |     |     |     |
| Phe | Gly | Leu | Gly | Ser | Pro | Leu | Pro | Ser | Pro | Arg | Ala | Ser | Pro | Arg | Pro |
|     | 210 |     |     |     |     | 215 |     |     |     |     | 220 |     |     |     |     |
| Trp | Thr | Pro | Glu | Asp | Pro | Trp | Ser | Leu | Tyr | Gly | Pro | Ser | Pro | Gly | Gly |
| 225 |     |     |     |     | 230 |     |     |     |     | 235 |     |     |     |     | 240 |
| Arg | Gly | Pro | Glu | Asp | Ser | Trp | Leu | Leu | Leu | Ser | Ala | Pro | Gly | Pro | Thr |
|     |     |     |     | 245 |     |     |     |     | 250 |     |     |     |     | 255 |     |
| Pro | Ala | Ser | Pro | Arg | Pro | Ala | Ser | Pro | Cys | Gly | Lys | Arg | Arg | Tyr | Ser |
|     |     |     | 260 |     |     |     |     | 265 |     |     |     |     | 270 |     |     |
| Ser | Ser | Gly | Thr | Pro | Ser | Ser | Ala | Ser | Pro | Ala | Leu | Ser | Arg | Arg | Gly |
|     |     | 275 |     |     |     |     | 280 |     |     |     |     | 285 |     |     |     |
| Ser | Leu | Gly | Glu | Glu | Gly | Ser | Glu | Pro | Pro | Pro | Pro | Pro | Leu | Pro |     |
|     | 290 |     |     |     |     | 295 |     |     |     |     | 300 |     |     |     |     |
| Leu | Ala | Arg | Asp | Pro | Gly | Ser | Pro | Gly | Pro | Phe | Asp | Tyr | Val | Gly | Ala |
| 305 |     |     |     |     | 310 |     |     |     |     | 315 |     |     |     |     | 320 |
| Pro | Pro | Ala | Glu | Ser | Ile | Pro | Gln | Lys | Thr | Arg | Arg | Thr | Ser | Ser | Glu |
|     |     |     |     | 325 |     |     |     |     | 330 |     |     |     |     | 335 |     |
| Gln | Ala | Val | Ala | Leu | Pro | Arg | Ser | Glu | Glu | Pro | Ala | Ser | Cys | Asn | Gly |
|     |     |     | 340 |     |     |     |     | 345 |     |     |     |     | 350 |     |     |
| Lys | Leu | Pro | Leu | Gly | Ala | Glu | Glu | Ser | Val | Ala | Pro | Pro | Gly | Gly | Ser |
|     |     | 355 |     |     |     |     | 360 |     |     |     |     | 365 |     |     |     |
| Arg | Lys | Glu | Val | Ala | Gly | Met | Asp | Tyr | Leu | Ala | Val | Pro | Ser | Pro | Leu |
|     |     | 370 |     |     |     |     | 375 |     |     |     |     | 380 |     |     |     |
| Ala | Trp | Ser | Lys | Ala | Arg | Ile | Gly | Gly | His | Ser | Pro | Ile | Phe | Arg | Thr |
| 385 |     |     |     |     | 390 |     |     |     |     | 395 |     |     |     |     | 400 |

| | | | | | | | | | | | | | | |
|---|---|---|---|---|---|---|---|---|---|---|---|---|---|---|
| Ser | Ala | Leu | Pro | Pro 405 | Leu | Asp | Trp | Pro 410 | Leu | Pro | Ser | Gln | Tyr 415 | Gln |
| Leu | Glu | Leu | Arg 420 | Ile | Glu | Val | Gln | Pro 425 | Arg | Ala | His | His 430 | Arg | Ala | His |
| Tyr | Glu | Thr 435 | Glu | Gly | Ser | Arg | Gly 440 | Ala | Val | Lys | Ala | Ala 445 | Pro | Gly | Gly |
| His | Pro 450 | Val | Val | Lys | Leu | Leu 455 | Gly | Tyr | Ser | Glu | Lys 460 | Pro | Leu | Thr | Leu |
| Gln 465 | Met | Phe | Ile | Gly | Thr 470 | Ala | Asp | Glu | Arg | Asn 475 | Leu | Arg | Pro | His | Ala 480 |
| Phe | Tyr | Gln | Val | His 485 | Arg | Ile | Thr | Gly | Lys 490 | Met | Val | Ala | Thr | Ala 495 | Ser |
| Tyr | Glu | Ala | Val | Val 500 | Ser | Gly | Thr | Lys 505 | Val | Leu | Glu | Met | Thr 510 | Leu | Leu |
| Pro | Glu | Asn 515 | Asn | Met | Ala | Ala | Asn 520 | Ile | Asp | Cys | Ala | Gly 525 | Ile | Leu | Lys |
| Leu | Arg 530 | Asn | Ser | Asp | Ile | Glu 535 | Leu | Arg | Lys | Gly | Glu 540 | Thr | Asp | Ile | Gly |
| Arg 545 | Lys | Asn | Thr | Arg | Val 550 | Arg | Leu | Val | Phe | Arg 555 | Val | His | Val | Pro | Gln 560 |
| Gly | Gly | Gly | Lys | Val 565 | Val | Ser | Val | Gln | Ala 570 | Ala | Ser | Val | Pro | Ile 575 | Glu |
| Cys | Ser | Gln | Arg 580 | Ser | Ala | Gln | Glu | Leu 585 | Pro | Gln | Val | Glu | Ala 590 | Tyr | Ser |
| Pro | Ser | Ala 595 | Cys | Ser | Val | Arg | Gly 600 | Gly | Glu | Glu | Leu | Val 605 | Leu | Thr | Gly |
| Ser | Asn 610 | Phe | Leu | Pro | Asp | Ser 615 | Lys | Val | Val | Phe | Ile 620 | Glu | Arg | Gly | Pro |
| Asp 625 | Gly | Lys | Leu | Gln | Trp 630 | Glu | Glu | Glu | Ala | Thr 635 | Val | Asn | Arg | Leu | Gln 640 |
| Ser | Asn | Glu | Val | Thr 645 | Leu | Thr | Leu | Val | Pro 650 | Glu | Tyr | Ser | Asn | Lys 655 | |
| Arg | Val | Ser | Arg 660 | Pro | Val | Gln | Val | Tyr 665 | Phe | Tyr | Val | Ser | Asn 670 | Gly | Arg |
| Arg | Lys | Arg 675 | Ser | Pro | Thr | Gln | Ser 680 | Phe | Arg | Phe | Leu | Pro 685 | Val | Ile | Cys |
| Lys | Glu 690 | Glu | Pro | Leu | Pro | Asp 695 | Ser | Ser | Leu | Arg | Gly 700 | Phe | Pro | Ser | Ala |
| Ser 705 | Ala | Thr | Pro | Phe | Gly 710 | Thr | Asp | Met | Asp | Phe 715 | Ser | Pro | Pro | Arg | Pro 720 |
| Pro | Tyr | Pro | Ser | Tyr 725 | Pro | His | Glu | Asp | Pro 730 | Ala | Cys | Glu | Thr | Pro 735 | Tyr |
| Leu | Ser | Glu | Gly 740 | Phe | Gly | Tyr | Gly | Met 745 | Pro | Pro | Leu | Tyr | Pro 750 | Gln | Thr |
| Gly | Pro | Pro 755 | Pro | Ser | Tyr | Arg | Pro 760 | Gly | Leu | Arg | Met | Phe 765 | Pro | Glu | Thr |
| Arg | Gly 770 | Thr | Thr | Gly | Cys | Ala 775 | Gln | Pro | Pro | Ala | Val 780 | Ser | Phe | Leu | Pro |
| Arg 785 | Pro | Phe | Pro | Ser | Asp 790 | Pro | Tyr | Gly | Gly | Arg 795 | Gly | Ser | Ser | Phe | Pro 800 |
| Leu | Gly | Leu | Pro | Phe 805 | Ser | Pro | Pro | Ala | Pro 810 | Phe | Arg | Pro | Pro | Pro 815 | Leu |
| Pro | Ala | Ser | Pro 820 | Pro | Leu | Glu | Gly | Pro 825 | Phe | Pro | Ser | Gln | Ser 830 | Asp | Val |

```
His  Pro  Leu  Pro  Ala  Glu  Gly  Tyr  Asn  Lys  Val  Gly  Pro  Gly  Tyr  Gly
          835                     840                      845

Pro  Gly  Glu  Gly  Ala  Pro  Glu  Gln  Glu  Lys  Ser  Arg  Gly  Gly  Tyr  Ser
          850                     855                      860

Ser  Gly  Phe  Arg  Asp  Ser  Val  Pro  Ile  Gln  Gly  Ile  Thr  Leu  Glu  Glu
865                      870                     875                      880

Val  Ser  Glu  Ile  Ile  Gly  Arg  Asp  Leu  Ser  Gly  Phe  Pro  Ala  Pro  Pro
               885                     890                      895

Gly  Glu  Glu  Pro  Pro  Ala
               900
```

( 2 ) INFORMATION FOR SEQ ID NO:7:

( i ) SEQUENCE CHARACTERISTICS:
        ( A ) LENGTH: 2406 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 211..2337

( x i ) SEQUENCE DESCRIPTION: SEQ ID NO:7:

```
CGGCTGCGGT  TCCTGGTGCT  GCTCGGCGCG  CGGCCAGCTT  TCGGAACGGA  ACGCTCGGCG        60

TCGCGGGCCC  CGCCCGGAAA  GTTTGCCGTG  GAGTCGCGAC  CTCTTGGCCC  GCGCGGCCCG       120

GCATGAAGCG  GCGTTGAGGA  GCTGCTGCCG  CCGCTTGCCG  CTGCCGCCGC  CGCCGCCTGA       180

GGAGGAGCTG  CAGCACCCTG  GGCCACGCCG  ATG  ACT  ACT  GCA  AAC  TGT  GGC  GCC   234
                                    Met  Thr  Thr  Ala  Asn  Cys  Gly  Ala
                                         905                      910

CAC  GAC  GAG  CTC  GAC  TTC  AAA  CTC  GTC  TTT  GGC  GAG  GAC  GGG  GCG  CCG   282
His  Asp  Glu  Leu  Asp  Phe  Lys  Leu  Val  Phe  Gly  Glu  Asp  Gly  Ala  Pro
               915                     920                      925

GCG  CCG  CCG  CCC  CCG  GGC  TCG  CGG  CCT  GCA  GAT  CTT  GAG  CCA  GAT  GAT   330
Ala  Pro  Pro  Pro  Pro  Gly  Ser  Arg  Pro  Ala  Asp  Leu  Glu  Pro  Asp  Asp
          930                     935                      940

TGT  GCA  TCC  ATT  TAC  ATC  TTT  AAT  GTA  GAT  CCA  CCT  CCA  TCT  ACT  TTA   378
Cys  Ala  Ser  Ile  Tyr  Ile  Phe  Asn  Val  Asp  Pro  Pro  Pro  Ser  Thr  Leu
945                      950                     955

ACC  ACA  CCA  CTT  TGC  TTA  CCA  CAT  CAT  GGA  TTA  CCG  TCT  CAC  TCT  TCT   426
Thr  Thr  Pro  Leu  Cys  Leu  Pro  His  His  Gly  Leu  Pro  Ser  His  Ser  Ser
960                      965                     970                      975

GTT  TTG  TCA  CCA  TCG  TTT  CAG  CTC  CAA  AGT  CAC  AAA  AAC  TAT  GAA  GGA   474
Val  Leu  Ser  Pro  Ser  Phe  Gln  Leu  Gln  Ser  His  Lys  Asn  Tyr  Glu  Gly
                    980                     985                      990

ACT  TGT  GAG  ATT  CCT  GAA  TCT  AAA  TAT  AGC  CCA  TTA  GGT  GGT  CCC  AAA   522
Thr  Cys  Glu  Ile  Pro  Glu  Ser  Lys  Tyr  Ser  Pro  Leu  Gly  Gly  Pro  Lys
                    995                     1000                     1005

CCC  TTT  GAG  TGC  CCA  AGT  ATT  CAA  ATT  ACA  TCT  ATC  TCT  CCT  AAC  TGT   570
Pro  Phe  Glu  Cys  Pro  Ser  Ile  Gln  Ile  Thr  Ser  Ile  Ser  Pro  Asn  Cys
               1010                    1015                     1020

CAT  CAA  GAA  TTA  GAT  GCA  CAT  GAA  GAT  GAC  CTA  CAG  ATA  AAT  GAC  CCA   618
His  Gln  Glu  Leu  Asp  Ala  His  Glu  Asp  Asp  Leu  Gln  Ile  Asn  Asp  Pro
     1025                    1030                     1035

GAA  CGG  GAA  TTT  TTG  GAA  AGG  CCT  TCT  AGA  GAT  CAT  CTC  TAT  CTT  CCT   666
Glu  Arg  Glu  Phe  Leu  Glu  Arg  Pro  Ser  Arg  Asp  His  Leu  Tyr  Leu  Pro
1040                     1045                    1050                     1055

CTT  GAG  CCA  TCC  TAC  CGG  GAG  TCT  TCT  CTT  AGT  CCT  AGT  CCT  GCC  AGC   714
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| Leu | Glu | Pro | Ser | Tyr<br>1060 | Arg | Glu | Ser | Ser | Leu<br>1065 | Ser | Pro | Ser | Pro | Ala<br>1070 | Ser |  |
| AGC | ATC | TCT | TCT | AGG | AGT | TGG | TTC | TCT | GAT | GCA | TCT | TCT | TGT | GAA | TCG | 762 |
| Ser | Ile | Ser | Ser<br>1075 | Arg | Ser | Trp | Phe | Ser<br>1080 | Asp | Ala | Ser | Ser<br>1085 | Cys | Glu | Ser |  |
| CTT | TCA | CAT | ATT | TAT | GAT | GAT | GTG | GAC | TCA | GAG | TTG | AAT | GAA | GCT | GCA | 810 |
| Leu | Ser | His<br>1090 | Ile | Tyr | Asp | Asp | Val<br>1095 | Asp | Ser | Glu | Leu | Asn<br>1100 | Glu | Ala | Ala |  |
| GCC | CGA | TTT | ACC | CTT | GGA | TCC | CCT | CTG | ACT | TCT | CCT | GGT | GGC | TCT | CCA | 858 |
| Ala | Arg<br>1105 | Phe | Thr | Leu | Gly | Ser<br>1110 | Pro | Leu | Thr | Ser | Pro<br>1115 | Gly | Gly | Ser | Pro |  |
| GGG | GGC | TGC | CCT | GGA | GAA | GAA | ACT | TGG | CAT | CAA | CAG | TAT | GGA | CTT | GGA | 906 |
| Gly<br>1120 | Gly | Cys | Pro | Gly<br>1125 | Glu | Glu | Thr | Trp | His<br>1130 | Gln | Gln | Tyr | Gly | Leu<br>1135 | Gly |  |
| CAC | TCA | TTA | TCA | CCC | AGG | CAA | TCT | CCT | TGC | CAC | TCT | CCT | AGA | TCC | AGT | 954 |
| His | Ser | Leu | Ser | Pro<br>1140 | Arg | Gln | Ser | Pro<br>1145 | Cys | His | Ser | Pro | Arg<br>1150 | Ser | Ser |  |
| GTC | ACT | GAT | GAG | AAT | TGG | CTG | AGC | CCC | AGG | CCA | GCC | TCA | GGA | CCC | TCA | 1002 |
| Val | Thr | Asp | Glu | Asn<br>1155 | Trp | Leu | Ser | Pro | Arg<br>1160 | Pro | Ala | Ser | Gly | Pro<br>1165 | Ser |  |
| TCA | AGG | CCC | ACA | TCC | CCC | TGT | GGG | AAA | CGG | AGG | CAC | TCC | AGT | GCT | GAA | 1050 |
| Ser | Arg | Pro | Thr<br>1170 | Ser | Pro | Cys | Gly | Lys<br>1175 | Arg | Arg | His | Ser | Ser<br>1180 | Ala | Glu |  |
| GTT | TGT | TAT | GCT | GGG | TCC | CTT | TCA | CCC | CAT | CAC | TCA | CCT | GTT | CCT | TCA | 1098 |
| Val | Cys | Tyr | Ala<br>1185 | Gly | Ser | Leu | Ser | Pro<br>1190 | His | His | Ser | Pro | Val<br>1195 | Pro | Ser |  |
| CCT | GGT | CAC | TCC | CCC | AGG | GGA | AGT | GTG | ACA | GAA | GAT | ACG | TGG | CTC | AAT | 1146 |
| Pro | Gly<br>1200 | His | Ser | Pro | Arg<br>1205 | Gly | Ser | Val | Thr | Glu<br>1210 | Asp | Thr | Trp | Leu | Asn<br>1215 |  |
| GCT | TCT | GTC | CAT | GGT | GGG | TCA | GGC | TTG | GCC | CCT | GCA | GTT | TTT | CCA | TTT | 1194 |
| Ala | Ser | Val | His | Gly<br>1220 | Gly | Ser | Gly | Leu | Gly<br>1225 | Pro | Ala | Val | Phe | Pro<br>1230 | Phe |  |
| CAG | TAC | TGT | GTA | GAG | ACT | GAC | ATC | CCT | CTC | AAA | ACA | AGG | AAA | ACT | TCT | 1242 |
| Gln | Tyr | Cys | Val | Glu<br>1235 | Thr | Asp | Ile | Pro | Leu<br>1240 | Lys | Thr | Arg | Lys | Thr<br>1245 | Ser |  |
| GAA | GAT | CAA | GCT | GCC | ATA | CTA | CCA | GGA | AAA | TTA | GAG | CTG | TGT | TCA | GAT | 1290 |
| Glu | Asp | Gln | Ala | Ala<br>1250 | Ile | Leu | Pro | Gly | Lys<br>1255 | Leu | Glu | Leu | Cys | Ser<br>1260 | Asp |  |
| GAC | CAA | GGG | AGT | TTA | TCA | CCA | GCC | CGG | GAG | ACT | TCA | ATA | GAT | GAT | GGC | 1338 |
| Asp | Gln | Gly | Ser<br>1265 | Leu | Ser | Pro | Ala | Arg<br>1270 | Glu | Thr | Ser | Ile | Asp<br>1275 | Asp | Gly |  |
| CTT | GGA | TCT | CAG | TAT | CCT | TTA | AAG | AAA | GAT | TCA | TGT | GGT | GAT | CAG | TTT | 1386 |
| Leu<br>1280 | Gly | Ser | Gln | Tyr | Pro<br>1285 | Leu | Lys | Lys | Asp | Ser<br>1290 | Cys | Gly | Asp | Gln | Phe<br>1295 |  |
| CTT | TCA | GTT | CCT | TCA | CCC | TTT | ACC | TGG | AGC | AAA | CCA | AAG | CCT | GGC | CAC | 1434 |
| Leu | Ser | Val | Pro | Ser<br>1300 | Pro | Phe | Thr | Trp | Ser<br>1305 | Lys | Pro | Lys | Pro | Gly<br>1310 | His |  |
| ACC | CCT | ATA | TTT | CGC | ACA | TCT | TCA | TTA | CCT | CCA | CTA | GAC | TGG | CCT | TTA | 1482 |
| Thr | Pro | Ile | Phe | Arg<br>1315 | Thr | Ser | Ser | Leu | Pro<br>1320 | Pro | Leu | Asp | Trp | Pro<br>1325 | Leu |  |
| CCA | GCT | CAT | TTT | GGA | CAA | TGT | GAA | CTG | AAA | ATA | GAA | GTG | CAA | CCT | AAA | 1530 |
| Pro | Ala | His | Phe<br>1330 | Gly | Gln | Cys | Glu | Leu<br>1335 | Lys | Ile | Glu | Val | Gln<br>1340 | Pro | Lys |  |
| ACT | CAT | CAT | CGA | GCC | CAT | TAT | GAA | ACT | GAA | GGT | AGC | CGA | GGG | GCA | GTA | 1578 |
| Thr | His | His | Arg | Ala<br>1345 | His | Tyr | Glu | Thr | Glu<br>1350 | Gly | Ser | Arg | Gly | Ala<br>1355 | Val |  |
| AAA | GCA | TCT | ACT | GGG | GGA | CAT | CCT | GTT | GTG | AAG | CTC | CTG | GGC | TAT | AAC | 1626 |
| Lys | Ala | Ser | Thr<br>1360 | Gly | Gly | His | Pro<br>1365 | Val | Val | Lys | Leu<br>1370 | Leu | Gly | Tyr | Asn<br>1375 |  |
| GAA | AAG | CCA | ATA | AAT | CTA | CAA | ATG | TTT | ATT | GGG | ACA | GCA | GAT | GAT | CGA | 1674 |

```
Glu Lys Pro Ile Asn Leu Gln Met Phe Ile Gly Thr Ala Asp Asp Arg
            1380                1385                1390

TAT TTA CGA CCT CAT GCA TTT TAC CAG GTG CAT CGA ATC ACT GGG AAG          1722
Tyr Leu Arg Pro His Ala Phe Tyr Gln Val His Arg Ile Thr Gly Lys
            1395                1400                1405

ACA GTC GCT ACT GCA AGC CAA GAG ATA ATA ATT GCC AGT ACA AAA GTT          1770
Thr Val Ala Thr Ala Ser Gln Glu Ile Ile Ile Ala Ser Thr Lys Val
        1410                1415                1420

CTG GAA ATT CCA CTT CTT CCT GAA AAT AAT ATG TCA GCC AGT ATT GAT          1818
Leu Glu Ile Pro Leu Leu Pro Glu Asn Asn Met Ser Ala Ser Ile Asp
    1425                1430                1435

TGT GCA GGT ATT TTG AAA CTC CGC AAT TCA GAT ATA GAA CTT CGA AAA          1866
Cys Ala Gly Ile Leu Lys Leu Arg Asn Ser Asp Ile Glu Leu Arg Lys
1440                1445                1450                1455

GGA GAA ACT GAT ATT GGC AGA AAG AAT ACT AGA GTA CGA CTT GTG TTT          1914
Gly Glu Thr Asp Ile Gly Arg Lys Asn Thr Arg Val Arg Leu Val Phe
                1460                1465                1470

CGT GTA CAC ATC CCA CAG CCC AGT GGA AAA GTC CTT TCT CTG CAG ATA          1962
Arg Val His Ile Pro Gln Pro Ser Gly Lys Val Leu Ser Leu Gln Ile
            1475                1480                1485

GCC TCT ATA CCC GTT GAG TGC TCC CAG CGG TCT GCT CAA GAA CTT CCT          2010
Ala Ser Ile Pro Val Glu Cys Ser Gln Arg Ser Ala Gln Glu Leu Pro
        1490                1495                1500

CAT ATT GAG AAG TAC AGT ATC AAC AGT TGT TCT GTA AAT GGA GGT CAT          2058
His Ile Glu Lys Tyr Ser Ile Asn Ser Cys Ser Val Asn Gly Gly His
    1505                1510                1515

GAA ATG GTT GTG ACT GGA TCT AAT TTT CTT CCA GAA TCC AAA ATC ATT          2106
Glu Met Val Val Thr Gly Ser Asn Phe Leu Pro Glu Ser Lys Ile Ile
1520                1525                1530                1535

TTT CTT GAA AAA GGA CAA GAT GGA CGA CCT CAG TGG GAG GTA GAA GGG          2154
Phe Leu Glu Lys Gly Gln Asp Gly Arg Pro Gln Trp Glu Val Glu Gly
                1540                1545                1550

AAG ATA ATC AGG GAA AAA TGT CAA GGG GCT CAC ATT GTC CTT GAA GTT          2202
Lys Ile Ile Arg Glu Lys Cys Gln Gly Ala His Ile Val Leu Glu Val
            1555                1560                1565

CCT CCA TAT CAT AAC CCA GCA GTT ACA GCT GCA GTG CAG GTG CAC TTT          2250
Pro Pro Tyr His Asn Pro Ala Val Thr Ala Ala Val Gln Val His Phe
        1570                1575                1580

TAT CTT TGC AAT GGC AAG AGG AAA AAA AGC CAG TCT CAA CGT TTT ACT          2298
Tyr Leu Cys Asn Gly Lys Arg Lys Lys Ser Gln Ser Gln Arg Phe Thr
    1585                1590                1595

TAT ACA CCA GGT ACG AGG AGT CAT GAT GGT TTA CTA TAG AGCTTTCTTT           2347
Tyr Thr Pro Gly Thr Arg Ser His Asp Gly Leu Leu *
1600                1605                1610

CCTAATGAAT AAAAAGTTAT TTAACGAACA AAAAAAAAAA AAAAAAAAAA AAAAAAAA          2406
```

( 2 ) INFORMATION FOR SEQ ID NO:8:

( i ) SEQUENCE CHARACTERISTICS:
        ( A ) LENGTH: 708 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Thr Thr Ala Asn Cys Gly Ala His Asp Glu Leu Asp Phe Lys Leu
 1               5                  10                  15

Val Phe Gly Glu Asp Gly Ala Pro Ala Pro Pro Pro Gly Ser Arg
            20                  25                  30

Pro Ala Asp Leu Glu Pro Asp Asp Cys Ala Ser Ile Tyr Ile Phe Asn
```

|  | 35 |  |  |  |  | 40 |  |  |  |  | 45 |  |  |  |
|---|---|---|---|---|---|---|---|---|---|---|---|---|---|---|

Val Asp Pro Pro Pro Ser Thr Leu Thr Thr Pro Leu Cys Leu Pro His
    50                  55                  60

His Gly Leu Pro Ser His Ser Ser Val Leu Ser Pro Ser Phe Gln Leu
65              70                  75                      80

Gln Ser His Lys Asn Tyr Glu Gly Thr Cys Glu Ile Pro Glu Ser Lys
                85                  90                  95

Tyr Ser Pro Leu Gly Gly Pro Lys Pro Phe Glu Cys Pro Ser Ile Gln
            100             105             110

Ile Thr Ser Ile Ser Pro Asn Cys His Gln Glu Leu Asp Ala His Glu
        115             120             125

Asp Asp Leu Gln Ile Asn Asp Pro Glu Arg Glu Phe Leu Glu Arg Pro
    130             135             140

Ser Arg Asp His Leu Tyr Leu Pro Leu Glu Pro Ser Tyr Arg Glu Ser
145             150             155                     160

Ser Leu Ser Pro Ser Pro Ala Ser Ser Ile Ser Ser Arg Ser Trp Phe
            165             170             175

Ser Asp Ala Ser Ser Cys Glu Ser Leu Ser His Ile Tyr Asp Asp Val
            180             185             190

Asp Ser Glu Leu Asn Glu Ala Ala Arg Phe Thr Leu Gly Ser Pro
    195             200             205

Leu Thr Ser Pro Gly Gly Ser Pro Gly Gly Cys Pro Gly Glu Glu Thr
    210             215             220

Trp His Gln Gln Tyr Gly Leu Gly His Ser Leu Ser Pro Arg Gln Ser
225             230             235                     240

Pro Cys His Ser Pro Arg Ser Ser Val Thr Asp Glu Asn Trp Leu Ser
            245             250             255

Pro Arg Pro Ala Ser Gly Pro Ser Ser Arg Pro Thr Ser Pro Cys Gly
            260             265             270

Lys Arg Arg His Ser Ser Ala Glu Val Cys Tyr Ala Gly Ser Leu Ser
            275             280             285

Pro His His Ser Pro Val Pro Ser Pro Gly His Ser Pro Arg Gly Ser
    290             295             300

Val Thr Glu Asp Thr Trp Leu Asn Ala Ser Val His Gly Gly Ser Gly
305             310             315                     320

Leu Gly Pro Ala Val Phe Pro Phe Gln Tyr Cys Val Glu Thr Asp Ile
            325             330             335

Pro Leu Lys Thr Arg Lys Thr Ser Glu Asp Gln Ala Ala Ile Leu Pro
            340             345             350

Gly Lys Leu Glu Leu Cys Ser Asp Asp Gln Gly Ser Leu Ser Pro Ala
        355             360             365

Arg Glu Thr Ser Ile Asp Asp Gly Leu Gly Ser Gln Tyr Pro Leu Lys
    370             375             380

Lys Asp Ser Cys Gly Asp Gln Phe Leu Ser Val Pro Ser Pro Phe Thr
385             390             395                     400

Trp Ser Lys Pro Lys Pro Gly His Thr Pro Ile Phe Arg Thr Ser Ser
            405             410             415

Leu Pro Pro Leu Asp Trp Pro Leu Pro Ala His Phe Gly Gln Cys Glu
            420             425             430

Leu Lys Ile Glu Val Gln Pro Lys Thr His His Arg Ala His Tyr Glu
        435             440             445

Thr Glu Gly Ser Arg Gly Ala Val Lys Ala Ser Thr Gly Gly His Pro
    450             455             460

| | | | | | | | | | | | | | | |
|---|---|---|---|---|---|---|---|---|---|---|---|---|---|---|
| Val | Val | Lys | Leu | Leu | Gly | Tyr | Asn | Glu | Lys | Pro | Ile | Asn | Leu | Gln | Met |
| 465 | | | | | 470 | | | | 475 | | | | | 480 |
| Phe | Ile | Gly | Thr | Ala | Asp | Asp | Arg | Tyr | Leu | Arg | Pro | His | Ala | Phe | Tyr |
| | | | | 485 | | | | 490 | | | | | 495 | |
| Gln | Val | His | Arg | Ile | Thr | Gly | Lys | Thr | Val | Ala | Thr | Ala | Ser | Gln | Glu |
| | | | 500 | | | | 505 | | | | | 510 | | |
| Ile | Ile | Ile | Ala | Ser | Thr | Lys | Val | Leu | Glu | Ile | Pro | Leu | Leu | Pro | Glu |
| | | 515 | | | | 520 | | | | | 525 | | | | |
| Asn | Asn | Met | Ser | Ala | Ser | Ile | Asp | Cys | Ala | Gly | Ile | Leu | Lys | Leu | Arg |
| | 530 | | | | 535 | | | | | 540 | | | | | |
| Asn | Ser | Asp | Ile | Glu | Leu | Arg | Lys | Gly | Glu | Thr | Asp | Ile | Gly | Arg | Lys |
| 545 | | | | | 550 | | | | | 555 | | | | | 560 |
| Asn | Thr | Arg | Val | Arg | Leu | Val | Phe | Arg | Val | His | Ile | Pro | Gln | Pro | Ser |
| | | | | 565 | | | | | 570 | | | | | 575 | |
| Gly | Lys | Val | Leu | Ser | Leu | Gln | Ile | Ala | Ser | Ile | Pro | Val | Glu | Cys | Ser |
| | | | 580 | | | | | 585 | | | | | 590 | | |
| Gln | Arg | Ser | Ala | Gln | Glu | Leu | Pro | His | Ile | Glu | Lys | Tyr | Ser | Ile | Asn |
| | | 595 | | | | | 600 | | | | | 605 | | | |
| Ser | Cys | Ser | Val | Asn | Gly | Gly | His | Glu | Met | Val | Val | Thr | Gly | Ser | Asn |
| | 610 | | | | | 615 | | | | | 620 | | | | |
| Phe | Leu | Pro | Glu | Ser | Lys | Ile | Ile | Phe | Leu | Glu | Lys | Gly | Gln | Asp | Gly |
| 625 | | | | | 630 | | | | | 635 | | | | | 640 |
| Arg | Pro | Gln | Trp | Glu | Val | Glu | Gly | Lys | Ile | Ile | Arg | Glu | Lys | Cys | Gln |
| | | | | 645 | | | | | 650 | | | | | 655 | |
| Gly | Ala | His | Ile | Val | Leu | Glu | Val | Pro | Pro | Tyr | His | Asn | Pro | Ala | Val |
| | | | 660 | | | | | 665 | | | | | 670 | | |
| Thr | Ala | Ala | Val | Gln | Val | His | Phe | Tyr | Leu | Cys | Asn | Gly | Lys | Arg | Lys |
| | | 675 | | | | | 680 | | | | | 685 | | | |
| Lys | Ser | Gln | Ser | Gln | Arg | Phe | Thr | Tyr | Thr | Pro | Gly | Thr | Arg | Ser | His |
| | 690 | | | | | 695 | | | | | 700 | | | | |
| Asp | Gly | Leu | Leu | | | | | | | | | | | | |
| 705 | | | | | | | | | | | | | | | |

( 2 ) INFORMATION FOR SEQ ID NO:09:

( i ) SEQUENCE CHARACTERISTICS:
        ( A ) LENGTH: 2647 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 211..2427

( x i ) SEQUENCE DESCRIPTION: SEQ ID NO:09:

```
CGGCTGCGGT  TCCTGGTGCT  GCTCGGCGCG  CGGCCAGCTT  TCGGAACGGA  ACGCTCGGCG      60

TCGCGGGCCC  CGCCCGGAAA  GTTTGCCGTG  GAGTCGCGAC  CTCTTGGCCC  GCGCGGCCCG     120

GCATGAAGCG  GCGTTGAGGA  GCTGCTGCCG  CCGCTTGCCG  CTGCCGCCGC  CGCCGCCTGA     180

GGAGGAGCTG  CAGCACCCTG  GGCCACGCCG  ATG ACT ACT GCA AAC TGT GGC GCC        234
                                   Met Thr Thr Ala Asn Cys Gly Ala
                                    1               5

CAC GAC GAG CTC GAC TTC AAA CTC GTC TTT GGC GAG GAC GGG GCG CCG            282
His Asp Glu Leu Asp Phe Lys Leu Val Phe Gly Glu Asp Gly Ala Pro
         10                  15                  20

GCG CCG CCG CCC CCG GGC TCG CGG CCT GCA GAT CTT GAG CCA GAT GAT            330
```

-continued

| | | | | | | | | | | | | | | | | |
|---|---|---|---|---|---|---|---|---|---|---|---|---|---|---|---|---|
| Ala | Pro | Pro | Pro | Pro | Gly | Ser | Arg | Pro | Ala | Asp | Leu | Glu | Pro | Asp | Asp | |
| 25 | | | | 30 | | | | 35 | | | | | | 40 | | |
| TGT | GCA | TCC | ATT | TAC | ATC | TTT | AAT | GTA | GAT | CCA | CCT | CCA | TCT | ACT | TTA | 378 |
| Cys | Ala | Ser | Ile | Tyr | Ile | Phe | Asn | Val | Asp | Pro | Pro | Pro | Ser | Thr | Leu | |
| | | | 45 | | | | | 50 | | | | | 55 | | | |
| ACC | ACA | CCA | CTT | TGC | TTA | CCA | CAT | CAT | GGA | TTA | CCG | TCT | CAC | TCT | TCT | 426 |
| Thr | Thr | Pro | Leu | Cys | Leu | Pro | His | His | Gly | Leu | Pro | Ser | His | Ser | Ser | |
| | | 60 | | | | | 65 | | | | | 70 | | | | |
| GTT | TTG | TCA | CCA | TCG | TTT | CAG | CTC | CAA | AGT | CAC | AAA | AAC | TAT | GAA | GGA | 474 |
| Val | Leu | Ser | Pro | Ser | Phe | Gln | Leu | Gln | Ser | His | Lys | Asn | Tyr | Glu | Gly | |
| | | 75 | | | | | 80 | | | | | 85 | | | | |
| ACT | TGT | GAG | ATT | CCT | GAA | TCT | AAA | TAT | AGC | CCA | TTA | GGT | GGT | CCC | AAA | 522 |
| Thr | Cys | Glu | Ile | Pro | Glu | Ser | Lys | Tyr | Ser | Pro | Leu | Gly | Gly | Pro | Lys | |
| | | 90 | | | | 95 | | | | | 100 | | | | | |
| CCC | TTT | GAG | TGC | CCA | AGT | ATT | CAA | ATT | ACA | TCT | ATC | TCT | CCT | AAC | TGT | 570 |
| Pro | Phe | Glu | Cys | Pro | Ser | Ile | Gln | Ile | Thr | Ser | Ile | Ser | Pro | Asn | Cys | |
| 105 | | | | | 110 | | | | | 115 | | | | | 120 | |
| CAT | CAA | GAA | TTA | GAT | GCA | CAT | GAA | GAT | GAC | CTA | CAG | ATA | AAT | GAC | CCA | 618 |
| His | Gln | Glu | Leu | Asp | Ala | His | Glu | Asp | Asp | Leu | Gln | Ile | Asn | Asp | Pro | |
| | | | | 125 | | | | | 130 | | | | | 135 | | |
| GAA | CGG | GAA | TTT | TTG | GAA | AGG | CCT | TCT | AGA | GAT | CAT | CTC | TAT | CTT | CCT | 666 |
| Glu | Arg | Glu | Phe | Leu | Glu | Arg | Pro | Ser | Arg | Asp | His | Leu | Tyr | Leu | Pro | |
| | | | 140 | | | | | 145 | | | | | 150 | | | |
| CTT | GAG | CCA | TCC | TAC | CGG | GAG | TCT | TCT | CTT | AGT | CCT | AGT | CCT | GCC | AGC | 714 |
| Leu | Glu | Pro | Ser | Tyr | Arg | Glu | Ser | Ser | Leu | Ser | Pro | Ser | Pro | Ala | Ser | |
| | | 155 | | | | | 160 | | | | | 165 | | | | |
| AGC | ATC | TCT | TCT | AGG | AGT | TGG | TTC | TCT | GAT | GCA | TCT | TCT | TGT | GAA | TCG | 762 |
| Ser | Ile | Ser | Ser | Arg | Ser | Trp | Phe | Ser | Asp | Ala | Ser | Ser | Cys | Glu | Ser | |
| | 170 | | | | | 175 | | | | | 180 | | | | | |
| CTT | TCA | CAT | ATT | TAT | GAT | GAT | GTG | GAC | TCA | GAG | TTG | AAT | GAA | GCT | GCA | 810 |
| Leu | Ser | His | Ile | Tyr | Asp | Asp | Val | Asp | Ser | Glu | Leu | Asn | Glu | Ala | Ala | |
| 185 | | | | | 190 | | | | | 195 | | | | | 200 | |
| GCC | CGA | TTT | ACC | CTT | GGA | TCC | CCT | CTG | ACT | TCT | CCT | GGT | GGC | TCT | CCA | 858 |
| Ala | Arg | Phe | Thr | Leu | Gly | Ser | Pro | Leu | Thr | Ser | Pro | Gly | Gly | Ser | Pro | |
| | | | | 205 | | | | | 210 | | | | | 215 | | |
| GGG | GGC | TGC | CCT | GGA | GAA | GAA | ACT | TGG | CAT | CAA | CAG | TAT | GGA | CTT | GGA | 906 |
| Gly | Gly | Cys | Pro | Gly | Glu | Glu | Thr | Trp | His | Gln | Gln | Tyr | Gly | Leu | Gly | |
| | | | 220 | | | | | 225 | | | | | 230 | | | |
| CAC | TCA | TTA | TCA | CCC | AGG | CAA | TCT | CCT | TGC | CAC | TCT | CCT | AGA | TCC | AGT | 954 |
| His | Ser | Leu | Ser | Pro | Arg | Gln | Ser | Pro | Cys | His | Ser | Pro | Arg | Ser | Ser | |
| | | 235 | | | | | 240 | | | | | 245 | | | | |
| GTC | ACT | GAT | GAG | AAT | TGG | CTG | AGC | CCC | AGG | CCA | GCC | TCA | GGA | CCC | TCA | 1002 |
| Val | Thr | Asp | Glu | Asn | Trp | Leu | Ser | Pro | Arg | Pro | Ala | Ser | Gly | Pro | Ser | |
| | 250 | | | | | 255 | | | | | 260 | | | | | |
| TCA | AGG | CCC | ACA | TCC | CCC | TGT | GGG | AAA | CGG | AGG | CAC | TCC | AGT | GCT | GAA | 1050 |
| Ser | Arg | Pro | Thr | Ser | Pro | Cys | Gly | Lys | Arg | Arg | His | Ser | Ser | Ala | Glu | |
| 265 | | | | | 270 | | | | | 275 | | | | | 280 | |
| GTT | TGT | TAT | GCT | GGG | TCC | CTT | TCA | CCC | CAT | CAC | TCA | CCT | GTT | CCT | TCA | 1098 |
| Val | Cys | Tyr | Ala | Gly | Ser | Leu | Ser | Pro | His | His | Ser | Pro | Val | Pro | Ser | |
| | | | | 285 | | | | | 290 | | | | | 295 | | |
| CCT | GGT | CAC | TCC | CCC | AGG | GGA | AGT | GTG | ACA | GAA | GAT | ACG | TGG | CTC | AAT | 1146 |
| Pro | Gly | His | Ser | Pro | Arg | Gly | Ser | Val | Thr | Glu | Asp | Thr | Trp | Leu | Asn | |
| | | | 300 | | | | | 305 | | | | | 310 | | | |
| GCT | TCT | GTC | CAT | GGT | GGG | TCA | GGC | CTT | GGC | CCT | GCA | GTT | TTT | CCA | TTT | 1194 |
| Ala | Ser | Val | His | Gly | Gly | Ser | Gly | Leu | Gly | Pro | Ala | Val | Phe | Pro | Phe | |
| | | 315 | | | | | 320 | | | | | 325 | | | | |
| CAG | TAC | TGT | GTA | GAG | ACT | GAC | ATC | CCT | CTC | AAA | ACA | AGG | AAA | ACT | TCT | 1242 |
| Gln | Tyr | Cys | Val | Glu | Thr | Asp | Ile | Pro | Leu | Lys | Thr | Arg | Lys | Thr | Ser | |
| | 330 | | | | | 335 | | | | | 340 | | | | | |
| GAA | GAT | CAA | GCT | GCC | ATA | CTA | CCA | GGA | AAA | TTA | GAG | CTG | TGT | TCA | GAT | 1290 |

```
     Glu  Asp  Gln  Ala  Ala  Ile  Leu  Pro  Gly  Lys  Leu  Glu  Leu  Cys  Ser  Asp
     345                      350                     355                         360

GAC  CAA  GGG  AGT  TTA  TCA  CCA  GCC  CGG  GAG  ACT  TCA  ATA  GAT  GAT  GGC     1338
     Asp  Gln  Gly  Ser  Leu  Ser  Pro  Ala  Arg  Glu  Thr  Ser  Ile  Asp  Asp  Gly
                         365                      370                         375

CTT  GGA  TCT  CAG  TAT  CCT  TTA  AAG  AAA  GAT  TCA  TGT  GGT  GAT  CAG  TTT     1386
     Leu  Gly  Ser  Gln  Tyr  Pro  Leu  Lys  Lys  Asp  Ser  Cys  Gly  Asp  Gln  Phe
                    380                      385                     390

CTT  TCA  GTT  CCT  TCA  CCC  TTT  ACC  TGG  AGC  AAA  CCA  AAG  CCT  GGC  CAC     1434
     Leu  Ser  Val  Pro  Ser  Pro  Phe  Thr  Trp  Ser  Lys  Pro  Lys  Pro  Gly  His
               395                      400                     405

ACC  CCT  ATA  TTT  CGC  ACA  TCT  TCA  TTA  CCT  CCA  CTA  GAC  TGG  CCT  TTA     1482
     Thr  Pro  Ile  Phe  Arg  Thr  Ser  Ser  Leu  Pro  Pro  Leu  Asp  Trp  Pro  Leu
          410                      415                     420

CCA  GCT  CAT  TTT  GGA  CAA  TGT  GAA  CTG  AAA  ATA  GAA  GTG  CAA  CCT  AAA     1530
     Pro  Ala  His  Phe  Gly  Gln  Cys  Glu  Leu  Lys  Ile  Glu  Val  Gln  Pro  Lys
     425                      430                     435                         440

ACT  CAT  CAT  CGA  GCC  CAT  TAT  GAA  ACT  GAA  GGT  AGC  CGA  GGG  GCA  GTA     1578
     Thr  His  His  Arg  Ala  His  Tyr  Glu  Thr  Glu  Gly  Ser  Arg  Gly  Ala  Val
                         445                     450                         455

AAA  GCA  TCT  ACT  GGG  GGA  CAT  CCT  GTT  GTG  AAG  CTC  CTG  GGC  TAT  AAC     1626
     Lys  Ala  Ser  Thr  Gly  Gly  His  Pro  Val  Val  Lys  Leu  Leu  Gly  Tyr  Asn
                    460                      465                     470

GAA  AAG  CCA  ATA  AAT  CTA  CAA  ATG  TTT  ATT  GGG  ACA  GCA  GAT  GAT  CGA     1674
     Glu  Lys  Pro  Ile  Asn  Leu  Gln  Met  Phe  Ile  Gly  Thr  Ala  Asp  Asp  Arg
               475                      480                     485

TAT  TTA  CGA  CCT  CAT  GCA  TTT  TAC  CAG  GTG  CAT  CGA  ATC  ACT  GGG  AAG     1722
     Tyr  Leu  Arg  Pro  His  Ala  Phe  Tyr  Gln  Val  His  Arg  Ile  Thr  Gly  Lys
          490                      495                     500

ACA  GTC  GCT  ACT  GCA  AGC  CAA  GAG  ATA  ATA  ATT  GCC  AGT  ACA  AAA  GTT     1770
     Thr  Val  Ala  Thr  Ala  Ser  Gln  Glu  Ile  Ile  Ile  Ala  Ser  Thr  Lys  Val
     505                      510                     515                         520

CTG  GAA  ATT  CCA  CTT  CTT  CCT  GAA  AAT  AAT  ATG  TCA  GCC  AGT  ATT  GAT     1818
     Leu  Glu  Ile  Pro  Leu  Leu  Pro  Glu  Asn  Asn  Met  Ser  Ala  Ser  Ile  Asp
                         525                     530                         535

TGT  GCA  GGT  ATT  TTG  AAA  CTC  CGC  AAT  TCA  GAT  ATA  GAA  CTT  CGA  AAA     1866
     Cys  Ala  Gly  Ile  Leu  Lys  Leu  Arg  Asn  Ser  Asp  Ile  Glu  Leu  Arg  Lys
                    540                      545                     550

GGA  GAA  ACT  GAT  ATT  GGC  AGA  AAG  AAT  ACT  AGA  GTA  CGA  CTT  GTG  TTT     1914
     Gly  Glu  Thr  Asp  Ile  Gly  Arg  Lys  Asn  Thr  Arg  Val  Arg  Leu  Val  Phe
               555                      560                     565

CGT  GTA  CAC  ATC  CCA  CAG  CCC  AGT  GGA  AAA  GTC  CTT  TCT  CTG  CAG  ATA     1962
     Arg  Val  His  Ile  Pro  Gln  Pro  Ser  Gly  Lys  Val  Leu  Ser  Leu  Gln  Ile
          570                      575                     580

GCC  TCT  ATA  CCC  GTT  GAG  TGC  TCC  CAG  CGG  TCT  GCT  CAA  GAA  CTT  CCT     2010
     Ala  Ser  Ile  Pro  Val  Glu  Cys  Ser  Gln  Arg  Ser  Ala  Gln  Glu  Leu  Pro
     585                      590                     595                         600

CAT  ATT  GAG  AAG  TAC  AGT  ATC  AAC  AGT  TGT  TCT  GTA  AAT  GGA  GGT  CAT     2058
     His  Ile  Glu  Lys  Tyr  Ser  Ile  Asn  Ser  Cys  Ser  Val  Asn  Gly  Gly  His
                         605                     610                         615

GAA  ATG  GTT  GTG  ACT  GGA  TCT  AAT  TTT  CTT  CCA  GAA  TCC  AAA  ATC  ATT     2106
     Glu  Met  Val  Val  Thr  Gly  Ser  Asn  Phe  Leu  Pro  Glu  Ser  Lys  Ile  Ile
                    620                      625                     630

TTT  CTT  GAA  AAA  GGA  CAA  GAT  GGA  CGA  CCT  CAG  TGG  GAG  GTA  GAA  GGG     2154
     Phe  Leu  Glu  Lys  Gly  Gln  Asp  Gly  Arg  Pro  Gln  Trp  Glu  Val  Glu  Gly
               635                      640                     645

AAG  ATA  ATC  AGG  GAA  AAA  TGT  CAA  GGG  GCT  CAC  ATT  GTC  CTT  GAA  GTT     2202
     Lys  Ile  Ile  Arg  Glu  Lys  Cys  Gln  Gly  Ala  His  Ile  Val  Leu  Glu  Val
          650                      655                     660

CCT  CCA  TAT  CAT  AAC  CCA  GCA  GTT  ACA  GCT  GCA  GTG  CAG  GTG  CAC  TTT     2250
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Pro<br>665 | Pro | Tyr | His | Asn | Pro<br>670 | Ala | Val | Thr | Ala | Ala<br>675 | Val | Gln | Val | His | Phe<br>680 |      |
| TAT<br>Tyr | CTT<br>Leu | TGC<br>Cys | AAT<br>Asn | GGC<br>Gly<br>685 | AAG<br>Lys | AGG<br>Arg | AAA<br>Lys | AAA<br>Lys | AGC<br>Ser<br>690 | CAG<br>Gln | TCT<br>Ser | CAA<br>Gln | CGT<br>Arg | TTT<br>Phe<br>695 | ACT<br>Thr | 2298 |
| TAT<br>Tyr | ACA<br>Thr | CCA<br>Pro | GTT<br>Val<br>700 | TTG<br>Leu | ATG<br>Met | AAG<br>Lys | CAA<br>Gln | GAA<br>Glu<br>705 | CAC<br>His | AGA<br>Arg | GAA<br>Glu | GAG<br>Glu | ATT<br>Ile<br>710 | GAT<br>Asp | TTG<br>Leu | 2346 |
| TCT<br>Ser | TCA<br>Ser | GTT<br>Val<br>715 | CCA<br>Pro | ACT<br>Thr | TTG<br>Leu | CCA<br>Pro | CAG<br>Gln<br>720 | ACC<br>Thr | TCT<br>Ser | CGG<br>Arg | CAA<br>Gln | ACT<br>Thr<br>725 | CTG<br>Leu | CTC<br>Leu | GGG<br>Gly | 2394 |
| TCT<br>Ser | CAG<br>Gln<br>730 | CCT<br>Pro | CCT<br>Pro | TCA<br>Ser | GCT<br>Ala | TCT<br>Ser<br>735 | CCT<br>Pro | CCA<br>Pro | ACA<br>Thr | GTT<br>Val | TGATCTCCTC | | | TTCATATTTA | | 2447 |

```
TCTTCTTTGG  TGGAATACTT  GTCCGCCTGG  GCCTCCAGGG  ATTTCAAGTT  GTTGGTAACA    2507

ATTTTCAGCT  CCTCCTCTAG  GTCCCCACAT  TTACTCTCGG  CCACCTCAGC  CCTCTCCTCC    2567

GAGCGCTCCA  GCTCTCCTTC  CAGGATCACC  AGCTTCCTGG  CCACCTCTTC  ATATTTGCGG    2627

TCTGAATCCT  CAGCGATGTG                                                    2647
```

( 2 ) INFORMATION FOR SEQ ID NO:10:

( i ) SEQUENCE CHARACTERISTICS:
        ( A ) LENGTH: 739 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| | | | | | | | | | | | | | | | |
|---|---|---|---|---|---|---|---|---|---|---|---|---|---|---|---|
| Met<br>1 | Thr | Thr | Ala | Asn<br>5 | Cys | Gly | Ala | His | Asp<br>10 | Glu | Leu | Asp | Phe | Lys<br>15 | Leu |
| Val | Phe | Gly | Glu<br>20 | Asp | Gly | Ala | Pro | Ala<br>25 | Pro | Pro | Pro | Pro | Gly<br>30 | Ser | Arg |
| Pro | Ala | Asp<br>35 | Leu | Glu | Pro | Asp | Asp<br>40 | Cys | Ala | Ser | Ile | Tyr<br>45 | Ile | Phe | Asn |
| Val | Asp<br>50 | Pro | Pro | Pro | Ser<br>55 | Thr | Leu | Thr | Thr | Pro<br>60 | Leu | Cys | Leu | Pro | His |
| His<br>65 | Gly | Leu | Pro | Ser<br>70 | His | Ser | Ser | Val | Leu<br>75 | Ser | Pro | Ser | Phe | Gln<br>80 | Leu |
| Gln | Ser | His | Lys | Asn<br>85 | Tyr | Glu | Gly | Thr | Cys<br>90 | Glu | Ile | Pro | Glu | Ser<br>95 | Lys |
| Tyr | Ser | Pro | Leu<br>100 | Gly | Gly | Pro | Lys | Pro<br>105 | Phe | Glu | Cys | Pro | Ser<br>110 | Ile | Gln |
| Ile | Thr | Ser<br>115 | Ile | Ser | Pro | Asn | Cys<br>120 | His | Gln | Glu | Leu | Asp<br>125 | Ala | His | Glu |
| Asp | Asp<br>130 | Leu | Gln | Ile | Asn | Asp<br>135 | Pro | Glu | Arg | Glu | Phe<br>140 | Leu | Glu | Arg | Pro |
| Ser<br>145 | Arg | Asp | His | Leu | Tyr<br>150 | Leu | Pro | Leu | Glu | Pro<br>155 | Ser | Tyr | Arg | Glu | Ser<br>160 |
| Ser | Leu | Ser | Pro | Ser<br>165 | Pro | Ala | Ser | Ser | Ile<br>170 | Ser | Ser | Arg | Ser | Trp<br>175 | Phe |
| Ser | Asp | Ala | Ser<br>180 | Ser | Cys | Glu | Ser | Leu<br>185 | Ser | His | Ile | Tyr | Asp<br>190 | Asp | Val |
| Asp | Ser | Glu<br>195 | Leu | Asn | Glu | Ala | Ala<br>200 | Ala | Arg | Phe | Thr | Leu<br>205 | Gly | Ser | Pro |
| Leu | Thr | Ser<br>210 | Pro | Gly | Gly | Ser<br>215 | Pro | Gly | Gly | Cys | Pro<br>220 | Gly | Glu | Glu | Thr |

| | | | | | | | | | | | | | | |
|---|---|---|---|---|---|---|---|---|---|---|---|---|---|---|
| Trp | His | Gln | Gln | Tyr | Gly | Leu | Gly | His | Ser | Leu | Ser | Pro | Arg | Gln | Ser |
| 225 | | | | 230 | | | | 235 | | | | | | 240 |
| Pro | Cys | His | Ser | Pro | Arg | Ser | Ser | Val | Thr | Asp | Glu | Asn | Trp | Leu | Ser |
| | | | 245 | | | | | 250 | | | | | 255 | | |
| Pro | Arg | Pro | Ala | Ser | Gly | Pro | Ser | Ser | Arg | Pro | Thr | Ser | Pro | Cys | Gly |
| | | | 260 | | | | | 265 | | | | 270 | | | |
| Lys | Arg | Arg | His | Ser | Ser | Ala | Glu | Val | Cys | Tyr | Ala | Gly | Ser | Leu | Ser |
| | | 275 | | | | | 280 | | | | | 285 | | | |
| Pro | His | His | Ser | Pro | Val | Pro | Ser | Pro | Gly | His | Ser | Pro | Arg | Gly | Ser |
| | 290 | | | | | 295 | | | | 300 | | | | | |
| Val | Thr | Glu | Asp | Thr | Trp | Leu | Asn | Ala | Ser | Val | His | Gly | Gly | Ser | Gly |
| 305 | | | | | 310 | | | | 315 | | | | | | 320 |
| Leu | Gly | Pro | Ala | Val | Phe | Pro | Phe | Gln | Tyr | Cys | Val | Glu | Thr | Asp | Ile |
| | | | | 325 | | | | 330 | | | | | | 335 | |
| Pro | Leu | Lys | Thr | Arg | Lys | Thr | Ser | Glu | Asp | Gln | Ala | Ala | Ile | Leu | Pro |
| | | | 340 | | | | | 345 | | | | | 350 | | |
| Gly | Lys | Leu | Glu | Leu | Cys | Ser | Asp | Asp | Gln | Gly | Ser | Leu | Ser | Pro | Ala |
| | | 355 | | | | | 360 | | | | | 365 | | | |
| Arg | Glu | Thr | Ser | Ile | Asp | Asp | Gly | Leu | Gly | Ser | Gln | Tyr | Pro | Leu | Lys |
| | 370 | | | | | 375 | | | | | 380 | | | | |
| Lys | Asp | Ser | Cys | Gly | Asp | Gln | Phe | Leu | Ser | Val | Pro | Ser | Pro | Phe | Thr |
| 385 | | | | | 390 | | | | | 395 | | | | | 400 |
| Trp | Ser | Lys | Pro | Lys | Pro | Gly | His | Thr | Pro | Ile | Phe | Arg | Thr | Ser | Ser |
| | | | | 405 | | | | | 410 | | | | | 415 | |
| Leu | Pro | Pro | Leu | Asp | Trp | Pro | Leu | Pro | Ala | His | Phe | Gly | Gln | Cys | Glu |
| | | | 420 | | | | | 425 | | | | | 430 | | |
| Leu | Lys | Ile | Glu | Val | Gln | Pro | Lys | Thr | His | His | Arg | Ala | His | Tyr | Glu |
| | | 435 | | | | | 440 | | | | | 445 | | | |
| Thr | Glu | Gly | Ser | Arg | Gly | Ala | Val | Lys | Ala | Ser | Thr | Gly | Gly | His | Pro |
| | 450 | | | | | 455 | | | | | 460 | | | | |
| Val | Val | Lys | Leu | Leu | Gly | Tyr | Asn | Glu | Lys | Pro | Ile | Asn | Leu | Gln | Met |
| 465 | | | | | 470 | | | | 475 | | | | | | 480 |
| Phe | Ile | Gly | Thr | Ala | Asp | Asp | Arg | Tyr | Leu | Arg | Pro | His | Ala | Phe | Tyr |
| | | | | 485 | | | | | 490 | | | | | 495 | |
| Gln | Val | His | Arg | Ile | Thr | Gly | Lys | Thr | Val | Ala | Thr | Ala | Ser | Gln | Glu |
| | | | 500 | | | | | 505 | | | | | 510 | | |
| Ile | Ile | Ile | Ala | Ser | Thr | Lys | Val | Leu | Glu | Ile | Pro | Leu | Leu | Pro | Glu |
| | | 515 | | | | | 520 | | | | | 525 | | | |
| Asn | Asn | Met | Ser | Ala | Ser | Ile | Asp | Cys | Ala | Gly | Ile | Leu | Lys | Leu | Arg |
| | 530 | | | | | 535 | | | | | 540 | | | | |
| Asn | Ser | Asp | Ile | Glu | Leu | Arg | Lys | Gly | Glu | Thr | Asp | Ile | Gly | Arg | Lys |
| 545 | | | | | 550 | | | | | 555 | | | | | 560 |
| Asn | Thr | Arg | Val | Arg | Leu | Val | Phe | Arg | Val | His | Ile | Pro | Gln | Pro | Ser |
| | | | | 565 | | | | | 570 | | | | | 575 | |
| Gly | Lys | Val | Leu | Ser | Leu | Gln | Ile | Ala | Ser | Ile | Pro | Val | Glu | Cys | Ser |
| | | | 580 | | | | | 585 | | | | | 590 | | |
| Gln | Arg | Ser | Ala | Gln | Glu | Leu | Pro | His | Ile | Glu | Lys | Tyr | Ser | Ile | Asn |
| | | 595 | | | | | 600 | | | | | 605 | | | |
| Ser | Cys | Ser | Val | Asn | Gly | Gly | His | Glu | Met | Val | Val | Thr | Gly | Ser | Asn |
| | 610 | | | | | 615 | | | | | 620 | | | | |
| Phe | Leu | Pro | Glu | Ser | Lys | Ile | Ile | Phe | Leu | Glu | Lys | Gly | Gln | Asp | Gly |
| 625 | | | | | 630 | | | | | 635 | | | | | 640 |
| Arg | Pro | Gln | Trp | Glu | Val | Glu | Gly | Lys | Ile | Ile | Arg | Glu | Lys | Cys | Gln |

```
                            645                               650                               655
      Gly  Ala  His  Ile  Val  Leu  Glu  Val  Pro  Pro  Tyr  His  Asn  Pro  Ala  Val
                     660                          665                      670

Thr  Ala  Ala  Val  Gln  Val  His  Phe  Tyr  Leu  Cys  Asn  Gly  Lys  Arg  Lys
                675                            680                     685

Lys  Ser  Gln  Ser  Gln  Arg  Phe  Thr  Tyr  Thr  Pro  Val  Leu  Met  Lys  Gln
           690                      695                      700

Glu  His  Arg  Glu  Glu  Ile  Asp  Leu  Ser  Ser  Val  Pro  Thr  Leu  Pro  Gln
      705                      710                      715                           720

Thr  Ser  Arg  Gln  Thr  Leu  Leu  Gly  Ser  Gln  Pro  Pro  Ser  Ala  Ser  Pro
                     725                      730                      735

Pro  Thr  Val
```

( 2 ) INFORMATION FOR SEQ ID NO:11:

( i ) SEQUENCE CHARACTERISTICS:
        ( A ) LENGTH: 3969 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 211..3414

( x i ) SEQUENCE DESCRIPTION: SEQ ID NO:11:

```
CGGCTGCGGT  TCCTGGTGCT  GCTCGGCGCG  CGGCCAGCTT  TCGGAACGGA  ACGCTCGGCG      60

TCGCGGGCCC  CGCCCGGAAA  GTTTGCCGTG  GAGTCGCGAC  CTCTTGGCCC  GCGCGGCCCG     120

GCATGAAGCG  GCGTTGAGGA  GCTGCTGCCG  CCGCTTGCCG  CTGCCGCCGC  CGCCGCCTGA     180

GGAGGAGCTG  CAGCACCCTG  GGCCACGCCG  ATG  ACT  ACT  GCA  AAC  TGT  GGC  GCC    234
                                    Met  Thr  Thr  Ala  Asn  Cys  Gly  Ala
                                    740                      745

CAC  GAC  GAG  CTC  GAC  TTC  AAA  CTC  GTC  TTT  GGC  GAG  GAC  GGG  GCG  CCG    282
His  Asp  Glu  Leu  Asp  Phe  Lys  Leu  Val  Phe  Gly  Glu  Asp  Gly  Ala  Pro
          750                      755                      760

GCG  CCG  CCG  CCC  CCG  GGC  TCG  CGG  CCT  GCA  GAT  CTT  GAG  CCA  GAT  GAT    330
Ala  Pro  Pro  Pro  Pro  Gly  Ser  Arg  Pro  Ala  Asp  Leu  Glu  Pro  Asp  Asp
     765                      770                      775

TGT  GCA  TCC  ATT  TAC  ATC  TTT  AAT  GTA  GAT  CCA  CCT  CCA  TCT  ACT  TTA    378
Cys  Ala  Ser  Ile  Tyr  Ile  Phe  Asn  Val  Asp  Pro  Pro  Pro  Ser  Thr  Leu
780                      785                      790                      795

ACC  ACA  CCA  CTT  TGC  TTA  CCA  CAT  CAT  GGA  TTA  CCG  TCT  CAC  TCT  TCT    426
Thr  Thr  Pro  Leu  Cys  Leu  Pro  His  His  Gly  Leu  Pro  Ser  His  Ser  Ser
                    800                      805                      810

GTT  TTG  TCA  CCA  TCG  TTT  CAG  CTC  CAA  AGT  CAC  AAA  AAC  TAT  GAA  GGA    474
Val  Leu  Ser  Pro  Ser  Phe  Gln  Leu  Gln  Ser  His  Lys  Asn  Tyr  Glu  Gly
               815                      820                      825

ACT  TGT  GAG  ATT  CCT  GAA  TCT  AAA  TAT  AGC  CCA  TTA  GGT  GGT  CCC  AAA    522
Thr  Cys  Glu  Ile  Pro  Glu  Ser  Lys  Tyr  Ser  Pro  Leu  Gly  Gly  Pro  Lys
          830                      835                      840

CCC  TTT  GAG  TGC  CCA  AGT  ATT  CAA  ATT  ACA  TCT  ATC  TCT  CCT  AAC  TGT    570
Pro  Phe  Glu  Cys  Pro  Ser  Ile  Gln  Ile  Thr  Ser  Ile  Ser  Pro  Asn  Cys
     845                      850                      855

CAT  CAA  GAA  TTA  GAT  GCA  CAT  GAA  GAT  GAC  CTA  CAG  ATA  AAT  GAC  CCA    618
His  Gln  Glu  Leu  Asp  Ala  His  Glu  Asp  Asp  Leu  Gln  Ile  Asn  Asp  Pro
860                      865                      870                      875

GAA  CGG  GAA  TTT  TTG  GAA  AGG  CCT  TCT  AGA  GAT  CAT  CTC  TAT  CTT  CCT    666
Glu  Arg  Glu  Phe  Leu  Glu  Arg  Pro  Ser  Arg  Asp  His  Leu  Tyr  Leu  Pro
```

|  |  |  |  |  |  |  |  |  |  |  |  |  |  |  |  |  |
|---|---|---|---|---|---|---|---|---|---|---|---|---|---|---|---|---|
|  |  |  | 880 |  |  |  |  | 885 |  |  |  |  |  | 890 |  |  |
| CTT | GAG | CCA | TCC | TAC | CGG | GAG | TCT | TCT | CTT | AGT | CCT | AGT | CCT | GCC | AGC | 714 |
| Leu | Glu | Pro | Ser | Tyr | Arg | Glu | Ser | Ser | Leu | Ser | Pro | Ser | Pro | Ala | Ser |  |
|  |  |  | 895 |  |  |  |  | 900 |  |  |  |  | 905 |  |  |  |
| AGC | ATC | TCT | TCT | AGG | AGT | TGG | TTC | TCT | GAT | GCA | TCT | TCT | TGT | GAA | TCG | 762 |
| Ser | Ile | Ser | Ser | Arg | Ser | Trp | Phe | Ser | Asp | Ala | Ser | Ser | Cys | Glu | Ser |  |
|  |  | 910 |  |  |  |  | 915 |  |  |  |  | 920 |  |  |  |  |
| CTT | TCA | CAT | ATT | TAT | GAT | GAT | GTG | GAC | TCA | GAG | TTG | AAT | GAA | GCT | GCA | 810 |
| Leu | Ser | His | Ile | Tyr | Asp | Asp | Val | Asp | Ser | Glu | Leu | Asn | Glu | Ala | Ala |  |
|  | 925 |  |  |  |  | 930 |  |  |  |  | 935 |  |  |  |  |  |
| GCC | CGA | TTT | ACC | CTT | GGA | TCC | CCT | CTG | ACT | TCT | CCT | GGT | GGC | TCT | CCA | 858 |
| Ala | Arg | Phe | Thr | Leu | Gly | Ser | Pro | Leu | Thr | Ser | Pro | Gly | Gly | Ser | Pro |  |
| 940 |  |  |  |  | 945 |  |  |  |  | 950 |  |  |  |  | 955 |  |
| GGG | GGC | TGC | CCT | GGA | GAA | GAA | ACT | TGG | CAT | CAA | CAG | TAT | GGA | CTT | GGA | 906 |
| Gly | Gly | Cys | Pro | Gly | Glu | Glu | Thr | Trp | His | Gln | Gln | Tyr | Gly | Leu | Gly |  |
|  |  |  |  | 960 |  |  |  |  | 965 |  |  |  |  | 970 |  |  |
| CAC | TCA | TTA | TCA | CCC | AGG | CAA | TCT | CCT | TGC | CAC | TCT | CCT | AGA | TCC | AGT | 954 |
| His | Ser | Leu | Ser | Pro | Arg | Gln | Ser | Pro | Cys | His | Ser | Pro | Arg | Ser | Ser |  |
|  |  |  | 975 |  |  |  |  | 980 |  |  |  |  | 985 |  |  |  |
| GTC | ACT | GAT | GAG | AAT | TGG | CTG | AGC | CCC | AGG | CCA | GCC | TCA | GGA | CCC | TCA | 1002 |
| Val | Thr | Asp | Glu | Asn | Trp | Leu | Ser | Pro | Arg | Pro | Ala | Ser | Gly | Pro | Ser |  |
|  |  | 990 |  |  |  |  | 995 |  |  |  |  | 1000 |  |  |  |  |
| TCA | AGG | CCC | ACA | TCC | CCC | TGT | GGG | AAA | CGG | AGG | CAC | TCC | AGT | GCT | GAA | 1050 |
| Ser | Arg | Pro | Thr | Ser | Pro | Cys | Gly | Lys | Arg | Arg | His | Ser | Ser | Ala | Glu |  |
|  | 1005 |  |  |  |  | 1010 |  |  |  |  | 1015 |  |  |  |  |  |
| GTT | TGT | TAT | GCT | GGG | TCC | CTT | TCA | CCC | CAT | CAC | TCA | CCT | GTT | CCT | TCA | 1098 |
| Val | Cys | Tyr | Ala | Gly | Ser | Leu | Ser | Pro | His | His | Ser | Pro | Val | Pro | Ser |  |
| 1020 |  |  |  |  | 1025 |  |  |  |  | 1030 |  |  |  |  | 1035 |  |
| CCT | GGT | CAC | TCC | CCC | AGG | GGA | AGT | GTG | ACA | GAA | GAT | ACG | TGG | CTC | AAT | 1146 |
| Pro | Gly | His | Ser | Pro | Arg | Gly | Ser | Val | Thr | Glu | Asp | Thr | Trp | Leu | Asn |  |
|  |  |  |  | 1040 |  |  |  |  | 1045 |  |  |  |  | 1050 |  |  |
| GCT | TCT | GTC | CAT | GGT | GGG | TCA | GGC | CTT | GGC | CCT | GCA | GTT | TTT | CCA | TTT | 1194 |
| Ala | Ser | Val | His | Gly | Gly | Ser | Gly | Leu | Gly | Pro | Ala | Val | Phe | Pro | Phe |  |
|  |  |  | 1055 |  |  |  |  | 1060 |  |  |  |  | 1065 |  |  |  |
| CAG | TAC | TGT | GTA | GAG | ACT | GAC | ATC | CCT | CTC | AAA | ACA | AGG | AAA | ACT | TCT | 1242 |
| Gln | Tyr | Cys | Val | Glu | Thr | Asp | Ile | Pro | Leu | Lys | Thr | Arg | Lys | Thr | Ser |  |
|  |  | 1070 |  |  |  |  | 1075 |  |  |  |  | 1080 |  |  |  |  |
| GAA | GAT | CAA | GCT | GCC | ATA | CTA | CCA | GGA | AAA | TTA | GAG | CTG | TGT | TCA | GAT | 1290 |
| Glu | Asp | Gln | Ala | Ala | Ile | Leu | Pro | Gly | Lys | Leu | Glu | Leu | Cys | Ser | Asp |  |
|  | 1085 |  |  |  |  | 1090 |  |  |  |  | 1095 |  |  |  |  |  |
| GAC | CAA | GGG | AGT | TTA | TCA | CCA | GCC | CGG | GAG | ACT | TCA | ATA | GAT | GAT | GGC | 1338 |
| Asp | Gln | Gly | Ser | Leu | Ser | Pro | Ala | Arg | Glu | Thr | Ser | Ile | Asp | Asp | Gly |  |
| 1100 |  |  |  |  | 1105 |  |  |  |  | 1110 |  |  |  |  | 1115 |  |
| CTT | GGA | TCT | CAG | TAT | CCT | TTA | AAG | AAA | GAT | TCA | TGT | GGT | GAT | CAG | TTT | 1386 |
| Leu | Gly | Ser | Gln | Tyr | Pro | Leu | Lys | Lys | Asp | Ser | Cys | Gly | Asp | Gln | Phe |  |
|  |  |  |  | 1120 |  |  |  |  | 1125 |  |  |  |  | 1130 |  |  |
| CTT | TCA | GTT | CCT | TCA | CCC | TTT | ACC | TGG | AGC | AAA | CCA | AAG | CCT | GGC | CAC | 1434 |
| Leu | Ser | Val | Pro | Ser | Pro | Phe | Thr | Trp | Ser | Lys | Pro | Lys | Pro | Gly | His |  |
|  |  |  | 1135 |  |  |  |  | 1140 |  |  |  |  | 1145 |  |  |  |
| ACC | CCT | ATA | TTT | CGC | ACA | TCT | TCA | TTA | CCT | CCA | CTA | GAC | TGG | CCT | TTA | 1482 |
| Thr | Pro | Ile | Phe | Arg | Thr | Ser | Ser | Leu | Pro | Pro | Leu | Asp | Trp | Pro | Leu |  |
|  |  | 1150 |  |  |  |  | 1155 |  |  |  |  | 1160 |  |  |  |  |
| CCA | GCT | CAT | TTT | GGA | CAA | TGT | GAA | CTG | AAA | ATA | GAA | GTG | CAA | CCT | AAA | 1530 |
| Pro | Ala | His | Phe | Gly | Gln | Cys | Glu | Leu | Lys | Ile | Glu | Val | Gln | Pro | Lys |  |
| 1165 |  |  |  |  | 1170 |  |  |  |  | 1175 |  |  |  |  |  |  |
| ACT | CAT | CAT | CGA | GCC | CAT | TAT | GAA | ACT | GAA | GGT | AGC | CGA | GGG | GCA | GTA | 1578 |
| Thr | His | His | Arg | Ala | His | Tyr | Glu | Thr | Glu | Gly | Ser | Arg | Gly | Ala | Val |  |
| 1180 |  |  |  |  | 1185 |  |  |  |  | 1190 |  |  |  |  | 1195 |  |
| AAA | GCA | TCT | ACT | GGG | GGA | CAT | CCT | GTT | GTG | AAG | CTC | CTG | GGC | TAT | AAC | 1626 |
| Lys | Ala | Ser | Thr | Gly | Gly | His | Pro | Val | Val | Lys | Leu | Leu | Gly | Tyr | Asn |  |

|  |  |  |  |  |  |  |  |  |  |  |  |  |  |  |  |
|---|---|---|---|---|---|---|---|---|---|---|---|---|---|---|---|
| | | 1200 | | | | | 1205 | | | | | 1210 | | | |
| GAA | AAG | CCA | ATA | AAT | CTA | CAA | ATG | TTT | ATT | GGG | ACA | GCA | GAT | GAT | CGA | 1674 |
| Glu | Lys | Pro | Ile | Asn | Leu | Gln | Met | Phe | Ile | Gly | Thr | Ala | Asp | Asp | Arg | |
| | | | 1215 | | | | 1220 | | | | | 1225 | | | | |
| TAT | TTA | CGA | CCT | CAT | GCA | TTT | TAC | CAG | GTG | CAT | CGA | ATC | ACT | GGG | AAG | 1722 |
| Tyr | Leu | Arg | Pro | His | Ala | Phe | Tyr | Gln | Val | His | Arg | Ile | Thr | Gly | Lys | |
| | | 1230 | | | | | 1235 | | | | | 1240 | | | | |
| ACA | GTC | GCT | ACT | GCA | AGC | CAA | GAG | ATA | ATA | ATT | GCC | AGT | ACA | AAA | GTT | 1770 |
| Thr | Val | Ala | Thr | Ala | Ser | Gln | Glu | Ile | Ile | Ile | Ala | Ser | Thr | Lys | Val | |
| | | | 1245 | | | | 1250 | | | | | 1255 | | | | |
| CTG | GAA | ATT | CCA | CTT | CTT | CCT | GAA | AAT | AAT | ATG | TCA | GCC | AGT | ATT | GAT | 1818 |
| Leu | Glu | Ile | Pro | Leu | Leu | Pro | Glu | Asn | Asn | Met | Ser | Ala | Ser | Ile | Asp | |
| 1260 | | | | | 1265 | | | | | 1270 | | | | | 1275 | |
| TGT | GCA | GGT | ATT | TTG | AAA | CTC | CGC | AAT | TCA | GAT | ATA | GAA | CTT | CGA | AAA | 1866 |
| Cys | Ala | Gly | Ile | Leu | Lys | Leu | Arg | Asn | Ser | Asp | Ile | Glu | Leu | Arg | Lys | |
| | | | | 1280 | | | | | 1285 | | | | | 1290 | | |
| GGA | GAA | ACT | GAT | ATT | GGC | AGA | AAG | AAT | ACT | AGA | GTA | CGA | CTT | GTG | TTT | 1914 |
| Gly | Glu | Thr | Asp | Ile | Gly | Arg | Lys | Asn | Thr | Arg | Val | Arg | Leu | Val | Phe | |
| | | | 1295 | | | | 1300 | | | | | 1305 | | | | |
| CGT | GTA | CAC | ATC | CCA | CAG | CCC | AGT | GGA | AAA | GTC | CTT | TCT | CTG | CAG | ATA | 1962 |
| Arg | Val | His | Ile | Pro | Gln | Pro | Ser | Gly | Lys | Val | Leu | Ser | Leu | Gln | Ile | |
| | | 1310 | | | | | 1315 | | | | | 1320 | | | | |
| GCC | TCT | ATA | CCC | GTT | GAG | TGC | TCC | CAG | CGG | TCT | GCT | CAA | GAA | CTT | CCT | 2010 |
| Ala | Ser | Ile | Pro | Val | Glu | Cys | Ser | Gln | Arg | Ser | Ala | Gln | Glu | Leu | Pro | |
| | | 1325 | | | | | 1330 | | | | | 1335 | | | | |
| CAT | ATT | GAG | AAG | TAC | AGT | ATC | AAC | AGT | TGT | TCT | GTA | AAT | GGA | GGT | CAT | 2058 |
| His | Ile | Glu | Lys | Tyr | Ser | Ile | Asn | Ser | Cys | Ser | Val | Asn | Gly | Gly | His | |
| 1340 | | | | | 1345 | | | | | 1350 | | | | | 1355 | |
| GAA | ATG | GTT | GTG | ACT | GGA | TCT | AAT | TTT | CTT | CCA | GAA | TCC | AAA | ATC | ATT | 2106 |
| Glu | Met | Val | Val | Thr | Gly | Ser | Asn | Phe | Leu | Pro | Glu | Ser | Lys | Ile | Ile | |
| | | | | 1360 | | | | | 1365 | | | | | 1370 | | |
| TTT | CTT | GAA | AAA | GGA | CAA | GAT | GGA | CGA | CCT | CAG | TGG | GAG | GTA | GAA | GGG | 2154 |
| Phe | Leu | Glu | Lys | Gly | Gln | Asp | Gly | Arg | Pro | Gln | Trp | Glu | Val | Glu | Gly | |
| | | | 1375 | | | | 1380 | | | | | 1385 | | | | |
| AAG | ATA | ATC | AGG | GAA | AAA | TGT | CAA | GGG | GCT | CAC | ATT | GTC | CTT | GAA | GTT | 2202 |
| Lys | Ile | Ile | Arg | Glu | Lys | Cys | Gln | Gly | Ala | His | Ile | Val | Leu | Glu | Val | |
| | | | 1390 | | | | 1395 | | | | | 1400 | | | | |
| CCT | CCA | TAT | CAT | AAC | CCA | GCA | GTT | ACA | GCT | GCA | GTG | CAG | GTG | CAC | TTT | 2250 |
| Pro | Pro | Tyr | His | Asn | Pro | Ala | Val | Thr | Ala | Ala | Val | Gln | Val | His | Phe | |
| | | 1405 | | | | | 1410 | | | | | 1415 | | | | |
| TAT | CTT | TGC | AAT | GGC | AAG | AGG | AAA | AAA | AGC | CAG | TCT | CAA | CGT | TTT | ACT | 2298 |
| Tyr | Leu | Cys | Asn | Gly | Lys | Arg | Lys | Lys | Ser | Gln | Ser | Gln | Arg | Phe | Thr | |
| 1420 | | | | | 1425 | | | | | 1430 | | | | | 1435 | |
| TAT | ACA | CCA | GTT | TTG | ATG | AAG | CAA | GAA | CAC | AGA | GAA | GAG | ATT | GAT | TTG | 2346 |
| Tyr | Thr | Pro | Val | Leu | Met | Lys | Gln | Glu | His | Arg | Glu | Glu | Ile | Asp | Leu | |
| | | | | 1440 | | | | | 1445 | | | | | 1450 | | |
| TCT | TCA | GTT | CCA | TCT | TTG | CCT | GTG | CCT | CAT | CCT | GCT | CAG | ACC | CAG | AGG | 2394 |
| Ser | Ser | Val | Pro | Ser | Leu | Pro | Val | Pro | His | Pro | Ala | Gln | Thr | Gln | Arg | |
| | | | 1455 | | | | 1460 | | | | | 1465 | | | | |
| CCT | TCC | TCT | GAT | TCA | GGG | TGT | TCA | CAT | GAC | AGT | GTA | CTG | TCA | GGA | CAG | 2442 |
| Pro | Ser | Ser | Asp | Ser | Gly | Cys | Ser | His | Asp | Ser | Val | Leu | Ser | Gly | Gln | |
| | | 1470 | | | | | 1475 | | | | | 1480 | | | | |
| AGA | AGT | TTG | ATT | TGC | TCC | ATC | CCA | CAA | ACA | TAT | GCA | TCC | ATG | GTG | ACC | 2490 |
| Arg | Ser | Leu | Ile | Cys | Ser | Ile | Pro | Gln | Thr | Tyr | Ala | Ser | Met | Val | Thr | |
| 1485 | | | | | 1490 | | | | | 1495 | | | | | | |
| TCA | TCC | CAT | CTG | CCA | CAG | TTG | CAG | TGT | AGA | GAT | GAG | AGT | GTT | AGT | AAA | 2538 |
| Ser | Ser | His | Leu | Pro | Gln | Leu | Gln | Cys | Arg | Asp | Glu | Ser | Val | Ser | Lys | |
| 1500 | | | | | 1505 | | | | | 1510 | | | | | 1515 | |
| GAA | CAG | CAT | ATG | ATT | CCT | TCT | CCA | ATT | GTA | CAC | CAG | CCT | TTT | CAA | GTC | 2586 |
| Glu | Gln | His | Met | Ile | Pro | Ser | Pro | Ile | Val | His | Gln | Pro | Phe | Gln | Val | |

|  |  |  |  |  |  |  |  |  |  |  |  |  |  |  |  |
|---|---|---|---|---|---|---|---|---|---|---|---|---|---|---|---|
|  |  |  |  | 1520 |  |  |  | 1525 |  |  |  |  | 1530 |  |  |
| ACA | CCA | ACA | CCT | CCT | GTG | GGG | TCT | TCC | TAT | CAG | CCT | ATG | CAA | ACT | AAT |
| Thr | Pro | Thr | Pro | Pro | Val | Gly | Ser | Ser | Tyr | Gln | Pro | Met | Gln | Thr | Asn |
|  |  | 1535 |  |  |  |  | 1540 |  |  |  |  | 1545 |  |  |  |

2634

| GTT | GTG | TAC | AAT | GGA | CCA | ACT | TGT | CTT | CCT | ATT | AAT | GCT | GCC | TCT | AGT |
|---|---|---|---|---|---|---|---|---|---|---|---|---|---|---|---|
| Val | Val | Tyr | Asn | Gly | Pro | Thr | Cys | Leu | Pro | Ile | Asn | Ala | Ala | Ser | Ser |
|  | 1550 |  |  |  |  | 1555 |  |  |  |  | 1560 |  |  |  |  |

2682

| CAA | GAA | TTT | GAT | TCA | GTT | TTG | TTT | CAG | CAG | GAT | GCA | ACT | CTT | TCT | GGT |
|---|---|---|---|---|---|---|---|---|---|---|---|---|---|---|---|
| Gln | Glu | Phe | Asp | Ser | Val | Leu | Phe | Gln | Gln | Asp | Ala | Thr | Leu | Ser | Gly |
|  | 1565 |  |  |  |  | 1570 |  |  |  |  | 1575 |  |  |  |  |

2730

| TTA | GTG | AAT | CTT | GGC | TGT | CAA | CCA | CTG | TCA | TCC | ATA | CCA | TTT | CAT | TCT |
|---|---|---|---|---|---|---|---|---|---|---|---|---|---|---|---|
| Leu | Val | Asn | Leu | Gly | Cys | Gln | Pro | Leu | Ser | Ser | Ile | Pro | Phe | His | Ser |
| 1580 |  |  |  |  | 1585 |  |  |  |  | 1590 |  |  |  |  | 1595 |

2778

| TCA | AAT | TCA | GGC | TCA | ACA | GGA | CAT | CTC | TTA | GCC | CAT | ACA | CCT | CAT | TCT |
|---|---|---|---|---|---|---|---|---|---|---|---|---|---|---|---|
| Ser | Asn | Ser | Gly | Ser | Thr | Gly | His | Leu | Leu | Ala | His | Thr | Pro | His | Ser |
|  |  |  |  | 1600 |  |  |  |  | 1605 |  |  |  |  | 1610 |  |

2826

| GTG | CAT | ACC | CTG | CCT | CAT | CTG | CAA | TCA | ATG | GGA | TAT | CAT | TGT | TCA | AAT |
|---|---|---|---|---|---|---|---|---|---|---|---|---|---|---|---|
| Val | His | Thr | Leu | Pro | His | Leu | Gln | Ser | Met | Gly | Tyr | His | Cys | Ser | Asn |
|  |  |  | 1615 |  |  |  |  | 1620 |  |  |  |  | 1625 |  |  |

2874

| ACA | GGA | CAA | AGA | TCT | CTT | TCT | TCT | CCA | GTG | GCT | GAC | CAG | ATT | ACA | GGT |
|---|---|---|---|---|---|---|---|---|---|---|---|---|---|---|---|
| Thr | Gly | Gln | Arg | Ser | Leu | Ser | Ser | Pro | Val | Ala | Asp | Gln | Ile | Thr | Gly |
|  |  | 1630 |  |  |  |  | 1635 |  |  |  |  | 1640 |  |  |  |

2922

| CAG | CCT | TCG | TCT | CAG | TTA | CAA | CCT | ATT | ACA | TAT | GGT | CCT | TCA | CAT | TCA |
|---|---|---|---|---|---|---|---|---|---|---|---|---|---|---|---|
| Gln | Pro | Ser | Ser | Gln | Leu | Gln | Pro | Ile | Thr | Tyr | Gly | Pro | Ser | His | Ser |
| 1645 |  |  |  |  | 1650 |  |  |  |  | 1655 |  |  |  |  |  |

2970

| GGG | TCT | GCT | ACA | ACA | GCT | TCC | CCA | GCA | GCT | TCT | CAT | CCC | TTG | GCT | AGT |
|---|---|---|---|---|---|---|---|---|---|---|---|---|---|---|---|
| Gly | Ser | Ala | Thr | Thr | Ala | Ser | Pro | Ala | Ala | Ser | His | Pro | Leu | Ala | Ser |
| 1660 |  |  |  |  | 1665 |  |  |  |  | 1670 |  |  |  |  | 1675 |

3018

| TCA | CCG | CTT | TCT | GGG | CCA | CCA | TCT | CCT | CAG | CTT | CAG | CCT | ATG | CCT | TAC |
|---|---|---|---|---|---|---|---|---|---|---|---|---|---|---|---|
| Ser | Pro | Leu | Ser | Gly | Pro | Pro | Ser | Pro | Gln | Leu | Gln | Pro | Met | Pro | Tyr |
|  |  |  |  | 1680 |  |  |  |  | 1685 |  |  |  |  | 1690 |  |

3066

| CAA | TCT | CCT | AGC | TCA | GGA | ACT | GCC | TCA | TCA | CCG | TCT | CCA | GCC | ACC | AGA |
|---|---|---|---|---|---|---|---|---|---|---|---|---|---|---|---|
| Gln | Ser | Pro | Ser | Ser | Gly | Thr | Ala | Ser | Ser | Pro | Ser | Pro | Ala | Thr | Arg |
|  |  |  | 1695 |  |  |  |  | 1700 |  |  |  |  | 1705 |  |  |

3114

| ATG | CAT | TCT | GGA | CAG | CAC | TCA | ACT | CAA | GCA | CAA | AGT | ACG | GGC | CAG | GGG |
|---|---|---|---|---|---|---|---|---|---|---|---|---|---|---|---|
| Met | His | Ser | Gly | Gln | His | Ser | Thr | Gln | Ala | Gln | Ser | Thr | Gly | Gln | Gly |
|  |  | 1710 |  |  |  |  | 1715 |  |  |  |  | 1720 |  |  |  |

3162

| GGT | CTT | TCT | GCA | CCT | TCA | TCC | TTA | ATA | TGT | CAC | AGT | TTG | TGT | GAT | CCA |
|---|---|---|---|---|---|---|---|---|---|---|---|---|---|---|---|
| Gly | Leu | Ser | Ala | Pro | Ser | Ser | Leu | Ile | Cys | His | Ser | Leu | Cys | Asp | Pro |
| 1725 |  |  |  |  | 1730 |  |  |  |  | 1735 |  |  |  |  |  |

3210

| GCG | TCA | TTT | CCA | CCT | GAT | GGG | GCA | ACT | GTG | AGC | ATT | AAA | CCT | GAA | CCA |
|---|---|---|---|---|---|---|---|---|---|---|---|---|---|---|---|
| Ala | Ser | Phe | Pro | Pro | Asp | Gly | Ala | Thr | Val | Ser | Ile | Lys | Pro | Glu | Pro |
| 1740 |  |  |  |  | 1745 |  |  |  |  | 1750 |  |  |  |  | 1755 |

3258

| GAA | GAT | CGA | GAG | CCT | AAC | TTT | GCA | ACC | ATT | GGT | CTG | CAG | GAC | ATC | ACT |
|---|---|---|---|---|---|---|---|---|---|---|---|---|---|---|---|
| Glu | Asp | Arg | Glu | Pro | Asn | Phe | Ala | Thr | Ile | Gly | Leu | Gln | Asp | Ile | Thr |
|  |  |  |  | 1760 |  |  |  |  | 1765 |  |  |  |  | 1770 |  |

3306

| TTA | GAT | GAT | GAC | CAA | TTT | ATA | TCT | GAC | TTG | GAA | CAC | CAG | CCA | TCA | GGT |
|---|---|---|---|---|---|---|---|---|---|---|---|---|---|---|---|
| Leu | Asp | Asp | Asp | Gln | Phe | Ile | Ser | Asp | Leu | Glu | His | Gln | Pro | Ser | Gly |
|  |  |  | 1775 |  |  |  |  | 1780 |  |  |  |  | 1785 |  |  |

3354

| TCA | GCA | GAG | AAA | TGG | CCT | AAC | CAC | AGT | GTG | CTC | TCA | TGT | CCA | GCT | CCT |
|---|---|---|---|---|---|---|---|---|---|---|---|---|---|---|---|
| Ser | Ala | Glu | Lys | Trp | Pro | Asn | His | Ser | Val | Leu | Ser | Cys | Pro | Ala | Pro |
|  |  | 1790 |  |  |  |  | 1795 |  |  |  |  | 1800 |  |  |  |

3402

| TTC | TGG | AGA | ATC | TAGAGGTGAA | CGAGATAATT | GGGAGAGACA | TGTCCCAGAT |
|---|---|---|---|---|---|---|---|
| Phe | Trp | Arg | Ile |  |  |  |  |
|  |  |  | 1805 |  |  |  |  |

3454

| TTCTGTTTCC | CAAGGAGCAG | GGGTGAGCAG | GCAGGCTCCC | CTCCCGAGTC | CTGAGTCCCT | 3514 |
|---|---|---|---|---|---|---|
| GGATTTAGGA | AGATCTGATG | GGCTCTAACA | GTGCTTACTG | CAGCCTTGTG | TCCACCACCA | 3574 |
| ACTTCTCAGC | ATGTTTCTCT | CCTTGGACCT | TGGGTTTCCA | ACTCTGCAGC | CTTCAGGTCT | 3634 |

| | | | | |
|---|---|---|---|---|
| GGGGCCAGGA | GTGGGACCCA | CCATTTGTGG | GGAAAGTAGC | ATTCCTCCAC CTCAGGCCTT | 3694 |
| GGGTAGATTT | GGCAAAAGAA | CAGGAGCAGC | ATAGGCTGTT | TGAGCTTTGG GGAAATGAAC | 3754 |
| TTTGCTTTTT | ATATTTAACT | AGGATACTTT | TATATGATGG | GTGCTTTGAG TGTGAATGCA | 3814 |
| GCAGGCTCTC | TTGTTTCCGA | GGTGCTGCTT | TTGCAGGTGA | CCTGGTTACT TAGCTAGGAT | 3874 |
| TGGTGATTTG | TACTGCTTTA | TGGTCATTTG | AAGGGCCCTT | TAGTTTTTAT GATAATTTTT | 3934 |
| AAAATAGGAA | CTTTGATAA | GACCTTCTAG | AAGCC | | 3969 |

( 2 ) INFORMATION FOR SEQ ID NO:12:

( i ) SEQUENCE CHARACTERISTICS:
        ( A ) LENGTH: 1068 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Met Thr Thr Ala Asn Cys Gly Ala His Asp Glu Leu Asp Phe Lys Leu
 1               5                  10                  15

Val Phe Gly Glu Asp Gly Ala Pro Ala Pro Pro Pro Gly Ser Arg
                20                  25                  30

Pro Ala Asp Leu Glu Pro Asp Asp Cys Ala Ser Ile Tyr Ile Phe Asn
                35                  40                  45

Val Asp Pro Pro Pro Ser Thr Leu Thr Thr Pro Leu Cys Leu Pro His
        50                  55                  60

His Gly Leu Pro Ser His Ser Ser Val Leu Ser Pro Ser Phe Gln Leu
65                  70                  75                  80

Gln Ser His Lys Asn Tyr Glu Gly Thr Cys Glu Ile Pro Glu Ser Lys
                85                  90                  95

Tyr Ser Pro Leu Gly Gly Pro Lys Pro Phe Glu Cys Pro Ser Ile Gln
               100                 105                 110

Ile Thr Ser Ile Ser Pro Asn Cys His Gln Glu Leu Asp Ala His Glu
           115                 120                 125

Asp Asp Leu Gln Ile Asn Asp Pro Glu Arg Glu Phe Leu Glu Arg Pro
       130                 135                 140

Ser Arg Asp His Leu Tyr Leu Pro Leu Glu Pro Ser Tyr Arg Glu Ser
145                 150                 155                 160

Ser Leu Ser Pro Ser Pro Ala Ser Ser Ile Ser Ser Arg Ser Trp Phe
               165                 170                 175

Ser Asp Ala Ser Ser Cys Glu Ser Leu Ser His Ile Tyr Asp Asp Val
           180                 185                 190

Asp Ser Glu Leu Asn Glu Ala Ala Ala Arg Phe Thr Leu Gly Ser Pro
       195                 200                 205

Leu Thr Ser Pro Gly Gly Ser Pro Gly Gly Cys Pro Gly Glu Glu Thr
210                 215                 220

Trp His Gln Gln Tyr Gly Leu Gly His Ser Leu Ser Pro Arg Gln Ser
225                 230                 235                 240

Pro Cys His Ser Pro Arg Ser Ser Val Thr Asp Glu Asn Trp Leu Ser
               245                 250                 255

Pro Arg Pro Ala Ser Gly Pro Ser Ser Arg Pro Thr Ser Pro Cys Gly
           260                 265                 270

Lys Arg Arg His Ser Ser Ala Glu Val Cys Tyr Ala Gly Ser Leu Ser
       275                 280                 285

Pro His His Ser Pro Val Pro Ser Pro Gly His Ser Pro Arg Gly Ser
290                 295                 300
```

```
Val  Thr  Glu  Asp  Thr  Trp  Leu  Asn  Ala  Ser  Val  His  Gly  Gly  Ser  Gly
305                      310                      315                      320

Leu  Gly  Pro  Ala  Val  Phe  Pro  Phe  Gln  Tyr  Cys  Val  Glu  Thr  Asp  Ile
                    325                      330                      335

Pro  Leu  Lys  Thr  Arg  Lys  Thr  Ser  Glu  Asp  Gln  Ala  Ala  Ile  Leu  Pro
               340                      345                      350

Gly  Lys  Leu  Glu  Leu  Cys  Ser  Asp  Asp  Gln  Gly  Ser  Leu  Ser  Pro  Ala
          355                      360                      365

Arg  Glu  Thr  Ser  Ile  Asp  Asp  Gly  Leu  Gly  Ser  Gln  Tyr  Pro  Leu  Lys
     370                      375                      380

Lys  Asp  Ser  Cys  Gly  Asp  Gln  Phe  Leu  Ser  Val  Pro  Ser  Pro  Phe  Thr
385                      390                      395                      400

Trp  Ser  Lys  Pro  Lys  Pro  Gly  His  Thr  Pro  Ile  Phe  Arg  Thr  Ser  Ser
               405                      410                      415

Leu  Pro  Pro  Leu  Asp  Trp  Pro  Leu  Pro  Ala  His  Phe  Gly  Gln  Cys  Glu
               420                      425                      430

Leu  Lys  Ile  Glu  Val  Gln  Pro  Lys  Thr  His  His  Arg  Ala  His  Tyr  Glu
          435                      440                      445

Thr  Glu  Gly  Ser  Arg  Gly  Ala  Val  Lys  Ala  Ser  Thr  Gly  Gly  His  Pro
     450                      455                      460

Val  Val  Lys  Leu  Leu  Gly  Tyr  Asn  Glu  Lys  Pro  Ile  Asn  Leu  Gln  Met
465                      470                      475                      480

Phe  Ile  Gly  Thr  Ala  Asp  Asp  Arg  Tyr  Leu  Arg  Pro  His  Ala  Phe  Tyr
                    485                      490                      495

Gln  Val  His  Arg  Ile  Thr  Gly  Lys  Thr  Val  Ala  Thr  Ala  Ser  Gln  Glu
               500                      505                      510

Ile  Ile  Ile  Ala  Ser  Thr  Lys  Val  Leu  Glu  Ile  Pro  Leu  Leu  Pro  Glu
          515                      520                      525

Asn  Asn  Met  Ser  Ala  Ser  Ile  Asp  Cys  Ala  Gly  Ile  Leu  Lys  Leu  Arg
530                      535                      540

Asn  Ser  Asp  Ile  Glu  Leu  Arg  Lys  Gly  Glu  Thr  Asp  Ile  Gly  Arg  Lys
545                      550                      555                      560

Asn  Thr  Arg  Val  Arg  Leu  Val  Phe  Arg  Val  His  Ile  Pro  Gln  Pro  Ser
                    565                      570                      575

Gly  Lys  Val  Leu  Ser  Leu  Gln  Ile  Ala  Ser  Ile  Pro  Val  Glu  Cys  Ser
               580                      585                      590

Gln  Arg  Ser  Ala  Gln  Glu  Leu  Pro  His  Ile  Glu  Lys  Tyr  Ser  Ile  Asn
          595                      600                      605

Ser  Cys  Ser  Val  Asn  Gly  Gly  His  Glu  Met  Val  Val  Thr  Gly  Ser  Asn
     610                      615                      620

Phe  Leu  Pro  Glu  Ser  Lys  Ile  Ile  Phe  Leu  Glu  Lys  Gly  Gln  Asp  Gly
625                      630                      635                      640

Arg  Pro  Gln  Trp  Glu  Val  Glu  Gly  Lys  Ile  Ile  Arg  Glu  Lys  Cys  Gln
               645                      650                      655

Gly  Ala  His  Ile  Val  Leu  Glu  Val  Pro  Pro  Tyr  His  Asn  Pro  Ala  Val
               660                      665                      670

Thr  Ala  Ala  Val  Gln  Val  His  Phe  Tyr  Leu  Cys  Asn  Gly  Lys  Arg  Lys
          675                      680                      685

Lys  Ser  Gln  Ser  Gln  Arg  Phe  Thr  Tyr  Thr  Pro  Val  Leu  Met  Lys  Gln
     690                      695                      700

Glu  His  Arg  Glu  Glu  Ile  Asp  Leu  Ser  Ser  Val  Pro  Ser  Leu  Pro  Val
705                      710                      715                      720

Pro  His  Pro  Ala  Gln  Thr  Gln  Arg  Pro  Ser  Ser  Asp  Ser  Gly  Cys  Ser
```

```
                              725                         730                         735
His  Asp  Ser  Val  Leu  Ser  Gly  Gln  Arg  Ser  Leu  Ile  Cys  Ser  Ile  Pro
               740                      745                      750
Gln  Thr  Tyr  Ala  Ser  Met  Val  Thr  Ser  Ser  His  Leu  Pro  Gln  Leu  Gln
               755                      760                      765
Cys  Arg  Asp  Glu  Ser  Val  Ser  Lys  Glu  Gln  His  Met  Ile  Pro  Ser  Pro
     770                           775                      780
Ile  Val  His  Gln  Pro  Phe  Gln  Val  Thr  Pro  Thr  Pro  Pro  Val  Gly  Ser
785                      790                      795                           800
Ser  Tyr  Gln  Pro  Met  Gln  Thr  Asn  Val  Val  Tyr  Asn  Gly  Pro  Thr  Cys
                    805                      810                      815
Leu  Pro  Ile  Asn  Ala  Ala  Ser  Ser  Gln  Glu  Phe  Asp  Ser  Val  Leu  Phe
               820                      825                      830
Gln  Gln  Asp  Ala  Thr  Leu  Ser  Gly  Leu  Val  Asn  Leu  Gly  Cys  Gln  Pro
          835                      840                      845
Leu  Ser  Ser  Ile  Pro  Phe  His  Ser  Ser  Asn  Ser  Gly  Ser  Thr  Gly  His
     850                           855                      860
Leu  Leu  Ala  His  Thr  Pro  His  Ser  Val  His  Thr  Leu  Pro  His  Leu  Gln
865                           870                      875                      880
Ser  Met  Gly  Tyr  His  Cys  Ser  Asn  Thr  Gly  Gln  Arg  Ser  Leu  Ser  Ser
                    885                      890                           895
Pro  Val  Ala  Asp  Gln  Ile  Thr  Gly  Gln  Pro  Ser  Ser  Gln  Leu  Gln  Pro
               900                      905                           910
Ile  Thr  Tyr  Gly  Pro  Ser  His  Ser  Gly  Ser  Ala  Thr  Thr  Ala  Ser  Pro
          915                      920                      925
Ala  Ala  Ser  His  Pro  Leu  Ala  Ser  Ser  Pro  Leu  Ser  Gly  Pro  Pro  Ser
     930                      935                           940
Pro  Gln  Leu  Gln  Pro  Met  Pro  Tyr  Gln  Ser  Pro  Ser  Ser  Gly  Thr  Ala
945                      950                      955                           960
Ser  Ser  Pro  Ser  Pro  Ala  Thr  Arg  Met  His  Ser  Gly  Gln  His  Ser  Thr
               965                      970                      975
Gln  Ala  Gln  Ser  Thr  Gly  Gln  Gly  Gly  Leu  Ser  Ala  Pro  Ser  Ser  Leu
          980                      985                      990
Ile  Cys  His  Ser  Leu  Cys  Asp  Pro  Ala  Ser  Phe  Pro  Pro  Asp  Gly  Ala
          995                      1000                     1005
Thr  Val  Ser  Ile  Lys  Pro  Glu  Pro  Glu  Asp  Arg  Glu  Pro  Asn  Phe  Ala
     1010                          1015                     1020
Thr  Ile  Gly  Leu  Gln  Asp  Ile  Thr  Leu  Asp  Asp  Asp  Gln  Phe  Ile  Ser
1025                     1030                     1035                          1040
Asp  Leu  Glu  His  Gln  Pro  Ser  Gly  Ser  Ala  Glu  Lys  Trp  Pro  Asn  His
                    1045                     1050                     1055
Ser  Val  Leu  Ser  Cys  Pro  Ala  Pro  Phe  Trp  Arg  Ile
               1060                     1065
```

( 2 ) INFORMATION FOR SEQ ID NO:13:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

```
Asp  Ile  Glu  Leu  Arg  Lys  Gly  Glu  Thr  Asp  Ile  Gly  Arg  Lys  Asn  Thr
1                   5                        10                            15
```

```
        Arg  Val  Arg  Leu  Val  Phe  Arg  Val  His  Xaa  Pro
                       20                       25
```

( 2 ) INFORMATION FOR SEQ ID NO:14:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
        Pro  Xaa  Glu  Cys  Ser  Gln  Arg  Ser  Ala  Xaa  Glu  Leu  Pro
        1               5                        10
```

( 2 ) INFORMATION FOR SEQ ID NO:15:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

GGAAAATTTT          10

( 2 ) INFORMATION FOR SEQ ID NO:16:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

GGAAAAACTG          10

( 2 ) INFORMATION FOR SEQ ID NO:17:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

TACATTGGAA AATTTTATTA CAC          23

( 2 ) INFORMATION FOR SEQ ID NO:18:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

GGAGGAAAAA CTGTTTCATA CAGAAGGCGT          30

NUCLEAR FACTORS AND BINDING ASSAY

CROSS-REFERENCE TO RELATED APPLICATIONS

This application is a continuation-in-part of application Ser. No. 08/270,653, filed Jul. 5, 1994 now abandoned, the disclosure of which is hereby incorporated by reference.

INTRODUCTION

FIELD OF THE INVENTION

The field of this invention is human transcription factors of activated T-cells.

BACKGROUND

Identifying and developing new pharmaceuticals is a multibillion dollar industry in the U.S. alone. Gene specific transcription factors provide a promising class of targets for novel therapeutics directed to these and other human diseases. Urgently needed are efficient methods of identifying pharmacological agents or drugs which are active at the level of gene transcription. If amenable to automated, cost-effective, high throughput drug screening, such methods would have immediate application in a broad range of domestic and international pharmaceutical and biotechnology drug development programs.

Immunosuppression is therapeutically desirable in a wide variety of circumstances including transplantation, allergy and other forms of hypersensitivity, autoimmunity, etc. Cyclosporin, a widely used drug for effecting immunosuppression, is believed to act by inhibiting a calcineurin, a phosphatase which activates certain nuclear factors of activated T-cells (NFATs). However, because of side effects and toxicity, clinical indications of cyclosporin (and the more recently developed FK506) are limited.

Accordingly, it is desired to identify agents which more specifically interfere with the function of hNFATs. Unfortunately, the reagents necessary for the development of high-throughput screening assays for such therapeutics are unavailable.

RELEVANT LITERATURE

Nolan (June 17, 1994) Cell 77, 1–20 provides a recent review and commentary on molecular interactions of hNFAT proteins. Northrop et al. (Jun. 9, 1994) Nature 369, 497–502 report the cloning of a cDNA encoding human NFATc. McCaffrey et al. (Oct. 29, 1993) Science 262, 750–754 report the cloning of a fragment of a gene encoding a murine NFATp$_1$.

SUMMARY OF THE INVENTION

The invention provides methods and compositions for identifying lead compounds and pharmacological agents useful in the diagnosis or treatment of disease associated with the expression of one or more genes modulated by a transcription complex containing a human nuclear factor of activated T-cells (hNFAT). Several forms of hNFAT are provided including hNFATs designated hNFATp$_1$, hNFATp$_2$, hNFATc, hNFAT3, hNFAT4a, hNFAT4b and hNFAT4c. The invention also provides isolated nucleic acid encoding the subject hNFATs, vectors and cells comprising such nucleic acids, and methods of recombinantly producing polypeptides comprising hNFAT. The invention also provides hNFAT-specific binding reagents such as hNFAT-specific antibodies.

Methods using the disclosed hNFATs in drug development programs involve combining a selected hNFAT with a natural intracellular hNFAT binding target and a candidate pharmacological agent. Natural intracellular binding targets include transcription factors, such as AP1 proteins and nucleic acids encoding a hNFAT binding sequence. The resultant mixture is incubated under conditions whereby, but for the presence of the candidate pharmacological agent, the hNFAT selectively binds the target. Then the presence or absence of selective binding between the hNFAT and target is detected. A wide variety of alternative embodiments of the general methods using hNFATs are disclosed. The methods are particularly suited to high-throughput screening where one or more steps are performed by a computer controlled electromechanical robot comprising an axial rotatable arm and the solid substrate is a portion of a well of a microtiter plate.

hNFAT SEQ ID NOS:

hNFATp$_1$ cDNA SEQ ID NO: 1
hNFATp$_1$ protein SEQ ID NO:2
hNFATp$_2$ cDNA SEQ ID NO: 1, bases 1–356 and 868–3478
hNFATp$_2$ protein SEQ ID NO:2, residues 220–921
hNFATc cDNA SEQ ID NO:3
hNFATc protein SEQ ID NO:4
hNFAT3 cDNA SEQ ID NO:5
hNFAT3 protein SEQ ID NO:6
hNFAT4a cDNA SEQ ID NO:7
hNFAT4a protein SEQ ID NO:8
hNFAT4b cDNA SEQ ID NO:7, bases 1–2307 and SEQ ID NO:9
hNFAT4b protein SEQ ID NO:8, residues 1–699 and SEQ ID NO: 10
hNFAT4c cDNA SEQ ID NO:7, bases 1–2307 and SEQ ID NO: 11
hNFAT4c protein SEQ ID NO: 8, residues 1–699 and SEQ ID NO: 12

DETAILED DESCRIPTION OF THE INVENTION

The invention provides methods and compositions relating to human NFATs. The subject hNFATs include regulators of cytokine gene expression that modulate immune system function. As such, hNFATs and HNFAT-encoding nucleic acids provide important targets for therapeutic intervention.

hNFATs derive from human cells, comprise invariant hNFAT rel domain peptides (see, Table 1) and share at least 50% pair-wise rel sequence identity with each of the disclosed hNFAT sequences. Invariant hNFAT rel domain peptides include from the N-terminal end of the rel domain, HHRAHYETEGSRGAVKA (SEQ ID NO:2, residues 419–435), PHAFYQVHRITGK (SEQ ID NO:2, residues 470–482), IDCAGILKLRN (SEQ ID NO:2, residues 513–523), DIELRKGETDIGRKNTRVRLVFRVHX$_1$P (SEQ ID NO:13), and PX2ECSQRSAX3ELP (SEQ ID NO: 14), where each X$_1$ and X$_2$ is hydrophobic residue such as valine or isoleucine, and X$_3$ is any residue, but preferably glutamine or histidine.

TABLE 1 hNFAT rel domains

| | | |
|---|---|---|
| NFATp | (SEQ ID NO: 2, residues 388–678) | |
| NFATc | (SEQ ID NO: 4, residues 406–697) | |
| NFAT3 | (SEQ ID NO: 6, residues 397–686) | |
| NFAT4b/c | (SEQ ID NO: 10, residues 411–700) | |
| NFATp | IPVTASLPPLEWPLSSQSCSYELRIEVQPKPHHRAHYETEGSRGAVKAPT | 50 |
| NFATc | SYMSPTLPALDWQLPSHSGPYELRIEVQPKSHHRAHYETEGSRGAVKASA | 50 |
| NFAT3 | IFRTSALPPLDWPLPSQYEQLELRIEVQPRAHHRAHYETEGSRGAVKAAP | 50 |
| NFAT4b/c | IFRTSSLPPLDWPLPAHFGQCELKIEVQPKTHHRAHYETEGSRGAVKAST | 50 |
| NFATp | GGHPVVQLHGYMENKPLGLQIFIGTADERILKPHAFYQVHRITGKTVTTT | 100 |
| NFATc | GGHPIVQLHGYLENEPLMLQLFIGTADDRLLRPHAFYQVHRITGKTVSTT | 100 |
| NFAT3 | GGHPVVKLLGYS-EKPLTLQMFIGTADERNLRPHAFYQVHRITGKMVATA | 99 |
| NFAT4b/c | GGHPVVKLLGYN-EKPINLQMFIGTADDRYLRPHAFYQVHRITGKTVATA | 99 |
| NFATp | SYEKIVGNTKVLEIPLEPKNNMRATIDCAGILKLRNADIELRKGETDIGR | 150 |
| NFATc | SHEAILSNTKVLEIPLLPENSMRAVIDCAGILKLRNSDIELRKGETDIGR | 150 |
| NFAT3 | SYEAVVSGTKVLEMTLLPENNMAANIDCAGILKLRNSDIELRKGETDIGR | 149 |
| NFAT4b/c | SQEIIIASTKVLEIPLLPENNMSASIDCAGILKLRNSDIELRKGETDIGR | 149 |
| NFATp | KNTRVRLVFRVHIPESSGRIVSLQTASNPIECSQRSAHELPMVERQDTDS | 200 |
| NFATc | KNTRVRLVFRVHVPQPSGRTLSLQVASNPIECSQRSAQELPLVEKQSTDS | 200 |
| NFAT3 | KNTRVRLVFRVHVPQGGGKVVSVQAASVPIECSQRSAQELPQVEAYSPSA | 199 |
| NFAT4b/c | KNTRVRLVFRVHIPQPSGKVLSLQIASIPVECSQRSAQELPHIEKYSINS | 199 |
| NFATp | CLVYGGQQMILTGQNFTSESKVVFTEKTTDGQQIWEMEATVDKDKSQPNM | 250 |
| NFATc | YPVVGGKKMVLSGHNFLQDSKVIFVEKAPDGHHVWEMEAKTDRDLCKPNS | 250 |
| NFAT3 | CSVRGGEELVLTGSNFLPDSKVVFIERGPDGKLQWEEEATVNRLQSNEVT | 249 |
| NFAT4b/c | CSVNGGHEMVVTGSNFLPESKIIFLEKGQDGRPQWEVEGKIIREKCQGAH | 249 |
| NFATp | LFVEIPEYRNKHIRTPVKVNFYVINGKRKRSQPQHFTYHPV | 291 |
| NFATc | LVVEIPPFRNQRITSPVHVSFYVCNGKRKRSQYQRFTYLPA | 291 |
| NFAT3 | LTLTVPEYSNKRVSRPVQVYFYVSNGRRKRSPTQSFRFLPV | 290 |
| NFAT4b/c | IVLEVPPYHNPAVTAAVQVHFYLCNGKRKKSQSQRFTYTPV | 290 |

In addition to the shared rel domains, some hNFATs have smaller regions of sequence similarity on the terminal side of the tel domains. For example, the amino terminal regions of hNFAT 4a, 4b and 4c and hNFATc have several regions of similarity (Table 2). The two largest regions (designated regions A and B in Table 2) contain 23 of 41 and 24 of 45 identical amino acids between the two proteins. hNFATp and hNFAT3 also have similarity to other hNFAT proteins in this region (Table 2). The homology between hNFAT3 and hNFAT 4a, 4b and 4c extends about 25 amino acids upstream of the rel region (designated region C in Table 2).

sequences and the 50% pair-wise tel domain identity, cDNAs of hNFAT transcripts typically share substantially overall sequence identity with one or more of the disclosed hNFAT sequences.

The subject hNFAT fragments have one or more hNFAT-specific binding affinities, including the ability to specifically bind at least one natural human intracellular hNFAT-specific binding target or a hNFAT-specific binding agent such as a hNFAT-specific antibody or a hNFAT-specific binding agent identified in assays such as described below. Accordingly, the specificity of hNFAT fragment specific

TABLE 2 hNFAT regions 5' to the rel domain

| | | | |
|---|---|---|---|
| A | NFATc | PSTATLSLPSLEAYRDPS-CLSPASSLSSRSCNSEASSYES | 195 |
| | NFAT4a | PSRDHLYLPLEPSYRESSLSPSPASSISSRSWFSDASSCES | 189 |
| | NFATc (SEQ ID NO: 4, residues 152–191) | | |
| | NFAT4a (SEQ ID NO: 8, residues 144–184) | | |
| B | NFATc | SPQHSPSTSPRASVTEESWLGAR-----SSRPASPCNKRKYSLNG | 272 |
| | NFAT4a | SPRQSPCHSPRSSVTDENWLSPRPASGPSSRPTSPCGKRRSSAEV | 281 |
| | NFATc (SEQ ID NO: 4, residues 233–272) | | |
| | NFAT4a (SEQ ID NO: 8, residues 236–281) | | |
| | NFATc | SSRPASPCNKRKYSLNG | 272 |
| | NFAT3 | SPRPASPCGKRRYSSSG | 275 |
| | NFATc (SEQ ID NO: 4, residues 256–272) | | |
| | NFAT3 (SEQ ID NO: 6, residues 259–275) | | |
| | NFATc | SPQHSPSTSPRASVTEESWLGARSSRP | 272 |
| | NFATp | SPRTSPIMSPRTSLAEDSCLGRHSPVP | 239 |
| | NFATc (SEQ ID NO: 4, residues 233–259) | | |
| | NFATp (SEQ ID NO: 2, residues 213–239) | | |
| C | NFAT3 | RKEVAGMDYLAVPSPLAWSKARIGGHSP | 396 |
| | NFAT4a | KKDSCGDQFLSVPSPFTWSKPKPG-HTP | 410 |
| | NFAT3 (SEQ ID NO: 6, residues 369–396) | | |
| | NFAT4a (SEQ ID NO: 8, residues 384–410) | | |

Nucleic acids encoding hNFATs may be isolated from human cells by screening cDNA libraries for human immune cells with probes or PCR primers derived from the disclosed hNFAT genes. In addition to the invariant hNFAT rel binding agents is confirmed by ensuring non-cross-reactivity with other NFATs. Furthermore, preferred hNFAT fragments are capable of eliciting an antibody capable of specifically binding an hNFAT. Methods for making immunogenic peptides through the use of conjugates, adjuvants, etc. and methods for eliciting antibodies, e.g. immunizing rabbits, are well known.

Exemplary natural intracellular binding targets include nucleic acids which comprise one or more hNFAT DNA binding sites. Functional hNFAT binding sites have been found in the promoters or enhancers of several different cytokine genes including IL-2, IL-4, IL-3, GM-CSF, and TNF-a and are often located next to AP-1 binding sites, which are recognized by members of the fos and jun families of transcription factors. Typically, the AP-1 binding sites adjacent to hNFAT sites are low affinity sites, and AP. 1 proteins cannot bind them independently. However, many NF-AT and AP-1 protein combinations are capable of cooperatively binding to DNA. Furthermore, cell-type specificity of cytokine gene transcription is often controlled, at least in part, by the combinations of hNFAT and AP-1 proteins present in those cells. For example, there are different classes of T cells that secrete different sets of cytokines: e.g. TH1 cells produce IL-2 and IFN-9, while TH2 cells produce IL-4, IL-5, and IL-6. hNFAT binding sites are involved in the regulation of both TH 1 and TH2 cytokines. Further, differential expression of the cytokine gene in T cell subsets is controlled the combinatorial interactions of hNFAT and AP-1 proteins.

In addition to DNA binding sites and other transcription factors such as AP1, other natural intracellular binding targets include cytoplasmic proteins such as ankyrin repeat containing hNFAT inhibitors, protein serine/threonine kinases, etc., and fragments of such targets which are capable of hNFAT-specific binding. Other natural hNFAT binding targets are readily identified by screening cells, membranes and cellular extracts and fractions with the disclosed materials and methods and by other methods known in the art. For example, two-hybrid screening using hNFAT fragments are used to identify intracellular targets which specifically bind such fragments. Preferred hNFAT fragments retain the ability to specifically bind at least one of an hNFAT DNA binding site and can preferably cooperatively bind with AP1. Convenient ways to verify the ability of a given hNFAT fragment to specifically bind such targets include in vitro labelled binding assays such as described below, and EMSAs.

A wide variety of molecular and biochemical methods are available for generating and expressing hNFAT fragments, see e.g. Molecular Cloning, A Laboratory Manual (2nd Ed., Sambrook, Fritsch and Maniatis, Cold Spring Harbor), Current Protocols in Molecular Biology (Eds. Aufubel, Brent, Kingston, More, Feidman, Smith and Stuhl, Greene Publ. Assoc., Wiley-Interscience, NY, N.Y., 1992) or that are otherwise known in the art. For example, hNFAT or fragments thereof may be obtained by chemical synthesis, expression in bacteria such as E. coli and eukaryotes such as yeast or vaccinia or baculovirus-based expression systems, etc., depending on the size, nature and quantity of the hNFAT or fragment. The subject hNFAT fragments are of length sufficient to provide a novel peptide. As used herein, such peptides are at least 5, usually at least about 6, more usually at least about 8, most usually at least about 10 amino acids. hNFAT fragments may be present in a free state or bound to other components such as blocking groups to chemically insulate reactive groups (e.g. amines, carboxyls, etc.) of the peptide, fusion peptides or polypeptides (i.e. the peptide may be present as a portion of a larger polypeptide), etc.

The subject hNFAT fragments maintain binding affinity of not less than six, preferably not less than four, more preferably not less than two orders of magnitude less than the binding equilibrium constant of a full-length native hNFAT to the binding target under similar conditions. Particular hNFAT fragments or deletion routants are shown to function in a dominant-negative fashion. Such fragments provide therapeutic agents, e.g. when delivered by intracellular immunization—transfection of susceptible cells with nucleic acids encoding such routants.

The claimed hNFAT and hNFAT fragments are isolated, partially pure or pure and are typically recombinantly produced. As used herein, an "isolated" peptide is unaccompanied by at least some of the material with which it is associated in its natural state and constitutes at least about 0.5%, preferably at least about 2%, and more preferably at least about 5% by weight of the total protein (including peptide) in a given sample; a partially pure peptide constitutes at least about 10%, preferably at least about 30%, and more preferably at least about 60%. by weight of the total protein in a given sample; and a pure peptide constitutes at least about 70%, preferably at least about 90%, and more preferably at least about 95% by weight of the total protein in a given sample.

Preferred hNFAT fragments comprise at least a functional portion of the rel domain. There are several different biochemical functions that are mediated by the tel and hNFAT rel-similarity domains: DNA binding, dimerization, interaction with B-zip proteins, interaction with inhibitor proteins, and nuclear localization. Other rel family proteins have been shown to physically interact with AP-1 (fos and jun) proteins (Stein et al., EMBO J. 12, 1993). The tel homology domain is necessary for this interaction and the B-zip region of the AP-1 proteins is involved in this protein-protein interaction. The specificity in the ability of hNFAT and AP-1 family members to interact is related to the tissue specific and cell type specific regulation of gene expression governed by these proteins. The tel and telsimilarity domains also interact with members of the I-kB family of inhibitor proteins including I-kB-like ankyrin repeat proteins (reviewed in Beg and Baldwin, Genes and Dev., 1993). The C-terminal half or the tel domain is involved the interaction with I-kB. There are 5 related I-kB-like proteins which are characterized by having multiple copies of a 33 amino acid sequence motif called the ankyrin repeat.

The invention provides hNFAT-specific binding agents, methods of identifying and making such agents, and their use in diagnosis, therapy and pharmaceutical development. For example, hNFAT-specific agents are useful in a variety of diagnostic applications, especially where disease or disease prognosis is associated with immune disfunction resulting from improper expression of hNFAT. Novel hNFAT-specific binding agents include hNFAT-specific antibodies and other natural intracellular binding agents identified with assays such as one- and two-hybrid screens; non-natural intracellular binding agents identified in screens of chemical libraries, etc.

Generally, hNFAT-specificity Of the binding target is shown by binding equilibrium constants. Such targets are capable of selectively binding a hNFAT, i.e. with an equilibrium constant at least about $10^4 M^{-1}$, preferably at least about $10^6 M^{-1}$, more preferably at least about $10^8 M^{-1}$. A wide variety of cell-based and cell-free assays may be used to demonstrate hNFAT-specific binding. Cell based assays include one and two-hybrid screens, mediating or competitively inhibiting hNFAT-mediated transcription, etc. Preferred are rapid in vitro, cell-free assays such as mediating or inhibiting hNFAT-protein (e.g. hNFAT-AP1 binding), hNFAT-nucleic acid binding, immunoassays, etc. Other useful screening assays for hNFAT/hNFAT fragment-target binding include fluorescence resonance energy transfer (FRET), electrophoretic mobility shift analysis (EMSA), etc.

The invention also provides nucleic acids encoding the subject hNFAT and hNFAT fragments, which nucleic acids may be part of hNFAT-expression vectors and may be incorporated into recombinant cells for expression and screening, transgenic animals for functional studies (e.g. the efficacy of candidate drugs for disease associated with expression of a hNFAT), etc. In addition, the invention provides nucleic acids sharing substantial sequence similarity with that of one or more wild-type hNFAT nucleic acids. Substantially identical or homologous nucleic acid sequences hybridize to their respective complements under high stringency conditions, for example, at 55° C. and hybridization buffer comprising 50% formamide in 0.9 M saline/0.09 M sodium citrate (SSC) buffer and remain bound when subject to washing at 55° C. with the SSC/formamide buffer. Where the sequences diverge, the differences are preferably silent, i.e. or a nucleotide change providing a redundant codon, or conservative, i.e. a nucleotide change providing a conservative amino acid substitution.

The subject nucleic acids find a wide variety of applications including use as hybridization probes, PCR primers, therapeutic nucleic acids, etc. for use in detecting the presence of hNFAT genes and gene transcripts, for detecting or amplifying nucleic acids with substantial sequence similarity such as hNFAT homologs and structural analogs, and for gene therapy applications. Given the subject probes, materials and methods for probing cDNA and genetic libraries and recovering homologs are known in the art. Preferred libraries are derived from human immune cells, especially cDNA libraries from differentiated and activated human lymphold cells. In one application, the subject nucleic acids find use as hybridization probes for identifying hNFAT cDNA homologs with substantial sequence similarity. These homologs in turn provide additional hNFATs and hNFAT fragments for use in binding assays and therapy as described herein. hNFAT encoding nucleic acids also find applications in gene therapy. For example, nucleic acids encoding dominant-negative hNFAT routants are cloned into a virus and the virus used to transfect and confer disease resistance to the transletted cells.

Therapeutic hNFAT nucleic acids are used to modulate, usually reduce, cellular expression or intracellular concentration or availability of active hNFAT. These nucleic acids are typically antisense: single-stranded sequences comprising complements of the disclosed hNFAT nucleic acids. Antisense modulation of hNFAT expression may employ hNFAT antisense nucleic acids operably linked to gene regulatory sequences. Cell are transfected with a vector comprising an hNFAT sequence with a promoter sequence oriented such that transcription of the gene yields an antisense transcript capable of binding to endogenous hNFAT encoding mRNA. Transcription of the antisense nucleic acid may be constitutive or inducible and the vector may provide for stable extrachromosomal maintenance or integration. Alternatively, single-stranded antisense nucleic acids that bind to genomic DNA or mRNA encoding a hNFAT or hNFAT fragment may be administered to the target cell, in or temporarily isolated from a host, at a concentration that results in a substantial reduction in hNFAT expression. For gene therapy involving the transfusion of hNFAT transfected cells, administration will depend on a number of variables that are ascertained empirically. For example, the number of cells will vary depending on the stability of the transfused cells. Transfusion media is typically a buffered saline solution or other pharmacologically acceptable solution. Similarly the amount of other administered compositions, e.g. transfected nucleic acid, protein, etc., will depend on the manner of administration, purpose of the therapy, and the like.

The subject nucleic acids are often recombinant, meaning they comprise a sequence joined to a nucleotide other than that which it is joined to on a natural chromosome. An isolated nucleic acid constitutes at least about 0.5%, preferably at least about 2%, and more preferably at least about 5% by weight of total nucleic acid present in a given fraction. A partially pure nucleic acid constitutes at least about 10%, preferably at least about 30%, and more preferably at least about 60% by weight of total nucleic acid present in a given fraction. A pure nucleic acid constitutes at least about 80%, preferably at least about 90%, and more preferably at least about 95% by weight of total nucleic acid present in a given fraction.

The invention provides efficient methods of identifying pharmacological agents or drugs which are active at the level of hNFAT modulatable cellular function, particularly hNFAT mediated interleukin signal transduction. Generally, these screening methods involve assaying for compounds which interfere with hNFAT activity such as hNFAT-AP1 binding, hNFAT-DNA binding, etc. The methods are amenable to automated, cost-effective high throughput drug screening and have immediate application in a broad range of domestic and international pharmaceutical and biotechnology drug development programs.

Target therapeutic indications are limited only in that the target cellular function (e.g. gene expression) be subject to modulation, usually inhibition, by disruption of the formation of a complex (e.g. transcription complex) comprising a hNFAT or hNFAT fragment and one or more natural hNFAT intracellular binding targets. Since a wide variety of genes are subject to hNFAT regulated gene transcription, target indications may include infection, metabolic disease, genetic disease, cell growth and regulatory disfunction, such as neoplasia, inflammation, hypersensitivity, etc. Frequently, the target indication is related to either immune dysfunction or selective immune suppression.

A wide variety of assays for binding agents are provided including labelled in vitro protein-protein and protein-DNA binding assay, electrophoretic mobility shift assays, immunoassays for protein binding or transcription complex formation, cell based assays such as one, two and three hybrid screens, expression assays such as transcription assays, etc. For example, three-hybrid screens are used to rapidly examine the effect of transfected nucleic acids, which may, for example, encode combinatorial peptide libraries or antisense molecules, on the intracellular binding of hNFAT or hNFAT fragments to intracellular hNFAT targets. Convenient reagents for such assays (e.g. GAL4 fusion partners) are known in the art.

hNFAT or hNFAT fragments used in the methods are usually added in an isolated, partially pure or pure form and are typically recombinantly produced. The hNFAT or fragment may be part of a fusion product with another peptide or polypeptide, e.g. a polypeptide that is capable of providing or enhancing protein-protein binding, sequence-specific nucleic acid binding or stability under assay conditions (e.g. a tag for detection or anchoring).

The assay mixtures comprise at least a portion of a natural intracellular hNFAT binding target such as AP1 or a nucleic acid comprising a sequence which shares sufficient sequence similarity with a gene or gene regulatory region to which the native hNFAT naturally binds to provide sequence-specific binding of the hNFAT or hNFAT fragment. Such a nucleic acid may further comprise one or more sequences which facilitate the binding of a second transcription factor or fragment thereof which cooperatively binds the nucleic acid with the hNFAT (i.e. at least one increases the affinity or specificity of the DNA binding of the other). While native binding targets may be used, it is frequently preferred to use portions (e.g. peptides, nucleic acid fragments) or analogs (i.e. agents which mimic the hNFAT binding properties of the natural binding target for the purposes of the assay) thereof so long as the portion provides binding affinity and avidity to the hNFAT conveniently measurable in the assay. Binding sequences for other transcription factors may be found in sources such as the Transcription Factor Database of the National Center for Biotechnology Information at the National Library for Medicine, in Faisst and Meyer (1991) Nucleic Acids Research 20, 3–26, and others known to those skilled in this art.

Where used, the nucleic acid portion bound by the peptide(s) may be continuous or segmented and is usually linear and double-stranded DNA, though circular plasmids or other nucleic acids or structural analogs may be substituted so long as hNFAT sequence-specific binding is retained. In some applications, supercoiled DNA provides optimal sequence-specific binding and is preferred. The nucleic acid may be of any length amenable to the assay conditions and requirements. Typically the nucleic acid is between 8 bp and 5 kb, preferably between about 12 bp and 1 kb, more preferably between about 18 bp and 250 bp, most preferably between about 27 and 50 bp. Additional nucleotides may be used to provide structure which enhances or decreased binding or stability, etc. For example, combinatorial DNA binding can be effected by including two or more DNA binding sites for different or the same transcription factor on the oligonucleotide. This allows for the study of cooperative or synergistic DNA binding of two or more factors. In addition, the nucleic acid can comprise a cassette into which transcription factor binding sites are conveniently spliced for use in the subject assays.

The assay mixture also comprises a candidate pharmacological agent. Generally a plurality of assay mixtures are run in parallel with different agent concentrations to obtain a differential response to the various concentrations. Typically, one of these concentrations serves as a negative control, i.e. at zero concentration or below the limits of assay detection. Candidate agents encompass numerous chemical classes, though typically they are organic compounds; preferably small organic compounds. Small organic compounds have a molecular weight of more than 50 yet less than about 2,500, preferably less than about 1000, more preferably, less than about 500. Candidate agents comprise functional chemical groups necessary for structural interactions with proteins and/or DNA, and typically include at least an amine, carbonyl, hydroxyl or carboxyl group, preferably at least two of the functional chemical groups, more preferably at least three. The candidate agents often comprise cyclical carbon or heterocyclic structures and/or aromatic or polyaromatic structures substituted with one or more of the forementioned functional groups. Candidate agents are also found among biomolecules including peptides, saccharities, fatty acids, steroids, purines, pyrimidines, derivatives, structural analogs or combinations thereof, and the like. Where the agent is or is encoded by a transfected nucleic acid, said nucleic acid is typically DNA or RNA.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural and synthetically produced libraries and compounds are readily modified through conventional chemical, physical, and biochemical means. In addition, known pharmacological agents may be subject to directed or random chemical modifications, such as acylation, alkylation, esterification, amidification, etc., to produce structural analogs.

A variety of other reagents may also be included in the mixture. These include reagents like salts, buffers, neutral proteins, e.g. albumin, detergents, etc. which may be used to facilitate optimal protein-protein and/or protein-nucleic acid binding and/or reduce non-specific or background interactions, etc. Also, reagents that otherwise improve the efficiency of the assay, such as protease inhibitors, nuclease inhibitors, antimicrobial agents, etc. may be used.

The resultant mixture is incubated under conditions whereby, but for the presence of the candidate pharmacological agent, the hNFAT specifically binds the cellular binding target, portion or analog. The mixture components can be added in any order that provides for the requisite bindings. Incubations may be performed at any temperature which facilitates optimal binding, typically between 4 and 40° C., more commonly between 15° and 40° C. Incubation periods are likewise selected for optimal binding but also minimized to facilitate rapid, high throughput screening, and are typically between 1 and 10 hours, preferably less than 5 hours, more preferably less than 2 hours.

After incubation, the presence or absence of specific binding between the hNFAT and one or more binding targets is detected by any convenient way. For cell-free binding type assays, a separation step is often used to separate bound from unbound components. The separation step may be accomplished in a variety of ways. Conveniently, at least one of the components is immobilized on a solid substrate which may be any solid from which the unbound components may be conveniently separated. The solid substrate may be made of a wide variety of materials and in a wide variety of shapes, e.g. microtiter plate, microbead, dipstick, resin particle, etc. The substrate is chosen to maximize signal to noise ratios, primarily to minimize background binding, for ease of washing and cost.

Separation may be effected for example, by removing a bead or dipstick from a reservoir, emptying or diluting reservoir such as a microtiter plate well, rinsing a bead (e.g. beads with iron cores may be readily isolated and washed using magnets), particle, chromatographic column or filter with a wash solution or solvent. Typically, the separation step will include an extended rinse or wash or a plurality of rinses or washes. For example, where the solid substrate is a microtiter plate, the wells may be washed several times with a washing solution, which typically includes those components of the incubation mixture that do not participate in specific binding such as salts, buffer, detergent, nonspecific protein, etc. may exploit a polypeptide specific binding reagent such as an antibody or receptor specific to a ligand of the polypeptide.

Detection may be effected in any convenient way. For cell based assays such as one, two, and three hybrid screens, the transcript resulting from hNFAT-target binding usually encodes a directly or indirectly detectable product (e.g.

galactosidase activity, luciferase activity, etc.). For cell-free binding assays, one of the components usually comprises or is coupled to a label. A wide variety of labels may be employed—essentially any label that provides for detection of bound protein. The label may provide for direct detection as radioactivity, luminescence, optical or electron density, etc. or indirect detection such as an epitope tag, an enzyme, etc. The label may be appended to the protein e.g. a phosphate group comprising a radioactive isotope of phosphorous, or incorporated into the protein structure, e.g. a methionine residue comprising a radioactive isotope of sulfur.

A variety of methods may be used to detect the label depending on the nature of the label and other assay components. For example, the label may be detected bound to the solid substrate or a portion of the bound complex containing the label may be separated from the solid substrate, and thereafter the label detected. Labels may be directly detected through optical or electron density, radiative emissions, nonradiative energy transfers, etc. or indirectly detected with antibody conjugates, etc. For example, in the case of radioactive labels, emissions may be detected directly, e.g. with particle counters or indirectly, e.g. with scintillation cocktails and counters. The methods are particularly suited to automated high throughput drug screening. Candidate agents shown to inhibit hNFAT—target binding or transcription complex formation provide valuable reagents to the pharmaceutical industries for animal and human trials.

As previously described, the methods are particularly suited to automated high throughput drug screening. In a particular embodiment, the arm retrieves and transfers a microtiter plate to a liquid dispensing station where measured aliquots of each an incubation buffer and a solution comprising one or more candidate agents are deposited into each designated well. The arm then retrieves and transfers to and deposits in designated wells a measured aliquot of a solution comprising a labeled transcription factor protein. After a first incubation period, the liquid dispensing station deposits in each designated well a measured aliquot of a biotinylated nucleic acid solution. The first and/or following second incubation may optionally occur after the arm transfers the plate to a shaker station. After a second incubation period, the arm transfers the microliter plate to a wash station where the unbound contents of each well is aspirated and then the well repeatedly filled with a wash buffer and aspirated. Where the bound label is radioactive phosphorous, the arm retrieves and transfers the plate to the liquid dispensing station where a measured aliquot of a scintillation cocktail is deposited in each designated well. Thereafter, the amount of label retained in each designated well is quantified.

In more preferred embodiments, the liquid dispensing station and arm are capable of depositing aliquots in at least eight wells simultaneously and the wash station is capable of filling and aspirating ninety-six wells simultaneously. Preferred robots are capable of processing at least 640 and preferably at least about 1,280 candidate agents every 24 hours, e.g. in microtiter plates. Of course, useful agents are identified with a range of other assays (e.g. gel shifts, etc.) employing the subject hNFAT and hNFAT fragments.

The subject hNFAT and hNFAT fragments and nucleic acids provide a wide variety of uses in addition to the in vitro binding assays described above. For example, cell-based assays are provided which involve transfecting a T-cell antigen receptor expressing cell with an hNFAT inducible reporter such as luciferase. Agents which modulate hNFAT mediated cell function are then detected through a change in the reporter.

The following examples are offered by way of illustration and not by way of limitation.

EXPERIMENTAL

Investigation of the antigen inducible expression of the IL-2 gene led to the discovery of the regulatory transcription factor NFAT (Nuclear Factor of Activated T cells) (Durand et al. 1988; Shaw et al. 1988). Like several other transcription factors involved in mediating signal transduction, the activity of NFAT is regulated by subcellular localization. In resting T cells NFAT activity is restricted to cytoplasm; stimulation of the T cell receptor leads to translocation of NFAT to the nucleus. Movement of NFAT to the nuecleus is dependent on the activation of the calcium-regulated phosphatase calcineurin (Clipstone and Crabtree 1992). The immunosuppressive drugs cyclosporin and FK506 inhibit the activity of calcineurin, and thereby prevent the nuclear localization of NFAT and subsequent activation of cytokine gene expression (reviewed in (Schreiber and Crabtree 1992).

Activation of the T cell antigen receptor induces two signalling pathways required for IL-2 induction, one is the cyclosporin-sensitive, calcium-dependent pathway and the other relies on the activation of protein kinase C (PKC). Antigenic stimulation of these pathways can be mimicked by treating cells with a calcium ionophore and a phorbol ester. The PKC-inducible activity was found to be mediated by fos and jun proteins (Jain et al. 1992; Northrop et al. 1993). The NFAT binding site in the IL-2 promoter is adjacent to a weak binding site for AP-1 proteins, and NFAT and AP-1 proteins bind cooperatively to this composite element (Jain et al. 1993; Northrop et al. 1993). The transcriptional activation mediated by AP-1 proteins through this site appears to be critical for IL-2 expression in activated T cells. There are several different combinations of fos and jun family members that can interact with NFAT to bind DNA (Boise et al. 1993; Northrop et al. 1993; Jain et al. 1994; Yaseen et al. 1994). Therefore, the composition of the AP-1 complex that interacts with NFAT may vary in different cell types and different stages of T cell activation. NFAT was originally reported to be a T cell specific transcription factor critical for the restricted expression of IL-2 (Shaw et al. 1988). More recently, NFAT activity was detected in B cells (Brabletz et al. 1991; Yaseen et al. 1993; Choi et al. 1994; Venkataraman et al. 1994). This is consistent with the finding that, in transgenic mice, the major sites of expression of a reporter gene regulated by the IL-2 NFAT/AP-1 site are activated T and B cells (Verweij et al. 1990).

In addition to IL-2, NFAT sites have been discovered in the promoters of several other cytokine genes, including IL-4 (Chuvpilo et al. 1993; Szabo et al. 1993; Rooney et al. 1994), IL-3 (Cockerill et al. 1993), GM-CSF (Masuda et al. 1993), and TNF-a (Goldreid et al. 1993). Thus, it appears that NFAT proteins are involved in the coordinate regulation of many different cytokines in activated lymphocytes. As with IL-2, most of the NFAT sites in other cytokine promoters are composite elements that also contain AP-1 binding sites (Rao, 1994).

Distinct genes encoding NFAT proteins have now been isolated (Jain et al. 1993; McCaffrey et al. 1993; Northrop et al. 1994; Hoey et al., in press). Two of these genes, designated NFATp and NFATc, encode related proteins that are highly similar to each other within a 290 amino acid domain. This NFAT homology region shares weak sequence similarity with the DNA binding and dimerization domain of the tel family of transcription factors (reviewed in (Nolan 1994). There is evidence that both NFATp and NFATc may be involved in mediating transcriptional regulation in activated T cells. For example, NFATp forms a specific complex on DNA with fos and jun that activates transcription in vitro (McCaffrey et al. 1993). NFATc has been shown to activate IL-2 expression by a cotransfection assay in T cells (Northrop et al. 1994). Furthermore, both proteins appears to be modified by calcineurin (Jain et al. 1993; Northrop et al. 1994). In addition to NFATp and NFATc, we have isolated two new members of the human NFAT gene family. We have used these clones to examine the tissue distribution of the different NFAT genes. We have also expressed and purified the DNA binding domains of the NFAT family proteins and investigated their biochemical activities.

Results

1. Cloning of human NFAT genes cDNA libraries were prepared from Jurkat T cells and human peripheral blood lymphocytes, and screened using a probe derived from the rel similarity region of the murine NFATp gene (McCaffrey et al. 1993). Cross-hybridizing clones were isolated, sequenced, and determined to be derived from 4 distinct genes.

One of the genes isolated in this study is related to the murine NFATp gene (McCaffrey et al. 1993), and another is identical to the NFATc gene (Northrop et al. 1994). We have isolated two classes of NFATp cDNAs which are the result of alternative splicing upstream of the rel domain. One form is similar to the cDNA reported by McCaffrey et al., while the other is alternatively spliced downstream of the rel similarity region; in particular, this form is missing an exon encoding the region near the N-terminus of the protein (SEQ ID NO: 1, base pairs 357–867) and has a different initiating methionine (SEQ ID NO:1, base pairs 880–882).

In addition to these previously identified genes, we cloned two novel members of the NFAT gene family, hereby designated as NFAT3 and NFAT4. The NFAT3 sequence was obtained from three overlapping cDNAs spanning 2880 bp, and deduced to encode a protein of 902 amino acids. We obtained three classes of NFAT4 cDNAs that resulted from alternative splicing downstream of the rel homology domain. These three types of cDNAs encode proteins that vary in sequence and length at their C-terminal ends. The three forms are designated NFAT4a, NFAT4b, and NFAT4c. The positions of splice junctions in the coding regions are after proline 699 in NFAT4a and after valine 700 and proline 716 in NFAT4b and NFAT4c.

All of the NFAT genes are at least 65% identical to each other within a 290 amino acid domain. This domain is related to the DNA binding and dimerization domain of the rel family of transcription factors (Nolan 1994; Northrop et al. 1994). Among the different NFAT genes, the N-terminal and central portions of the rel similarity domain are more highly conserved than the C-terminus.

Aside from the strikingly similar rel domains shared by all four NFAT genes, the NFAT family members have smaller regions of sequence similarity on the amino terminal side of the rel domains. The amino terminal regions of NFAT4 and NFATc have several regions of significant similarity. The two largest regions contain 23 of 41 and 24 of 45 identical amino acids between the two proteins. Both of these regions are rich in serine and proline residues. NFATp and NFAT3 also have some similarity to the other NFAT proteins in this region, although it is less extensive than that shared between NFAT4 and NFATc. The homology between NFAT3 and NFAT4 extends about 25 amino acids upstream of the rel similarity region.

2. Expression patterns of the NFAT genes

On the basis of previous reports, expression of NFAT genes was expected to be restricted to lymphocytes (Shaw et al. 1988; Verweij et al. 1990; McCaffrey et al. 1993; Northrop et al. 1994). The expression of each NFAT gene was tested by Northern blot using RNA from sixteen different human tissues. For NFATp, expression of an mRNA approximately 7.5 kb was detected in almost all human tissues. The expression was slightly higher in PBLs and placenta. NFATc expression was also detected at a low level in several different tissues. The NFATc probe hybridized to two bands of approximately 2.7 and 4.5 kb. Surprisingly, the 4.5 kb NFATc transcript was strongly expressed in skeletal muscle. The 2.7 kb mRNA appears to correspond to the previously described NFATc clone (Northrop et al. 1994).

NFAT3 exhibited a very complicated expression pattern with at least 3 major RNA bands between 3 and 5 kb. The major sites of NFAT3 expression were observed outside the immune system. NFAT3 was highly expressed in placenta, lung, kidney, testis and ovary. In contrast, NFAT3 expression was very weak in spleen and thymus and undetectable in PBLs.

NFAT4 was expressed predominately as a 6.5 kb message. Like NFATc it was strongly expressed in skeletal muscle. NFAT4 also displayed relatively high expression in thymus. The probe for the NFAT4 northerns contained the 3' half of the NFAT homology region as well as downstream regions from the NFAT4c class of cDNA. This probe should hybridize to all three classes of NFAT4 transcripts. Only one form is detected in the Northern blots, suggesting that the 4c class is the most abundant transcript.

These results indicate that each of the NFAT genes is expressed in a distinct tissue-specific pattern. Furthermore, none of the NFAT genes are restricted to lymphocytes.

3. DNA binding activity of the NFAT proteins

The rel similarity regions along with a small amount of flanking sequences of each of the four classes of NFAT proteins were expressed in *E. coli*. Each of the 4 proteins was well expressed and soluble. The proteins were purified to near homogeneity by DNA affinity chromatography (Kadonaga and Tjian 1986). The binding site used for purification was a high affinity NFAT site derived from the IL-4 promoter with the core binding sequence GGAAAATTT (SEQ ID NO: 15) (Rooney et al. 1994).

The binding specificities of the NFAT proteins were tested on two known functional binding sites, the IL-4 promoter NFAT site and the NFAT binding site in the distal antigen response element from the IL-2 promoter (Durand et al.. 1988; Shaw et al. 1988). All the proteins were able to bind the IL-4 promoter site. NFATp, NFATc, and NFAT3 recognized this sequence with very similar affinity, while NFAT4 bound this sequence with lower affinity (>10-fold) than the other three proteins in this assay. NFAT4 protein may have a different optimum binding sequence than the other NFAT proteins.

The same amounts of the four NFAT proteins were tested on the NFAT binding site from the IL-2 promoter. This NFAT site (GGAAAAACTG) (SEQ ID NO: 16) has three differences relative to the IL-4 site which make it a weaker site for all four NFAT proteins. The NFAT proteins differ in their ability to recognize this site independently. NFATp had the highest relative affinity for the IL-2 binding site, while NFATc and NFAT3 bound weakly to this site and NFAT4 binding was not detectable in this assay.

The IL-2 NFAT site is part of a composite element that is adjacent to a weak AP-1 site (TGTTTCA) (Jain et al. 1992; Northrop et al. 1993). To determine if there were any differences in the ability of NFAT proteins to interact with AP-1, the four NFAT proteins were tested with AP-1 for binding to the IL-2 site. When tested alone all the NFAT proteins, as well as the AP-1 proteins, bound relatively weakly to the IL-2 composite element. The combination of c-jun and fra1 with each of the four NFAT proteins resulted in highly cooperative DNA binding. In the presence of the AP-1 protein the four NFAT proteins bound to the IL-2 site with very similar affinity. In all cases, jun homodimers were not as effective as jun-fra1 heterodimers in promoting cooperative binding in the gel shift assay. These results indicate that the DNA binding and protein interaction specificity of the NFAT proteins are very similar. Indeed, the interactions of the four NFAT proteins with these AP-1 proteins appear to be identical. NFAT4 did not bind independently to this site, but recognized this site with the same affinity as the other NFAT proteins in the presence of AP-1.

4. Transcriptional activation by the NFAT proteins

Having established that the DNA binding properties of the four NFAT proteins are quite similar, we investigated their transcriptional activation potentials. We used a transient transfection assay into Jurkat T cells to measure the ability of the NFAT proteins to activate the IL-2 promoter. The IL-2 promoter was chosen because it is a critical regulatory target for NFAT and has at least two functional NFAT binding sites (Randak et al. 1990). Activation of this promoter by antigenic stimulation can be mimicked by treatment with phorbol esters, such as phorbol 12-myristate 13 acetate (PMA), together with ionomycin, a calcium ionophore.

Each of the four NFAT genes was transfected into Jurkat cells, and their ability to activate the IL-2 promoter was tested with various combinations of PMA and ionomycin. Treatment of the cells with PMA plus ionomycin induced strong activation by the endogenous NFAT proteins in Jurkat cells. Transfection of each of the four of the NFAT genes resulted in an additional stimulation the IL-2 promoter between 4- and 8-fold. Activation of the IL-2 promoter by each of the NFAT proteins was dependent on both PMA and ionomycin.

We also tested the ability of NFAT to activate transcription in COS and HepG2 cells using a synthetic reporter gene consisting three copies of an NFAT/AP-1 composite element. Transfection of each of the four NFAT into HepG2 cells resulted in activation of the reporter gene of at least 20-fold in the presence of PMA and ionomycin. In contrast to Jurkat cells, NFAT3 was more potent than the others in the HepG2 transfections, resulting in 140-fold activation. Another difference between the results of HepG2 and Jurkat cells is that the NFAT proteins appeared to activate transcription in the absence of PMA or calcium ionophore.

In COS cells NFAT3 produced a striking 50-fold activation that was observed independently of PMA and ionomycin treatment. NFAT3 was found to stimulate transcription in COS cells much more strongly than the other proteins.

5. NFAT proteins are active as monomers

There are many similar features of the NFAT and rel families of transcription factors. Rel proteins form homo- and heterodimers in solution, and dimerization is required for DNA binding (reviewed in Baeuerle and Henkel 1994). The C-terminal half of the tel homology domain is thought to be involved in mediating dimerization. Since the similarity between NFAT and the rel families extends throughout the 300 amino acid tel domain, and the rel domain of the NFkB proteins is sufficient for dimer formation, we expected that the NFAT proteins might also be function as directs. To test this idea we determined the native masses of the NFAT proteins by gel filtration chromatography and glycerol gradient centrifugation. For these experiments we used the rel similarity regions of NFATp and NFATc that were expressed in $E.\ coli$ and purified by DNA affinity chromatography. The molecular weights of these proteins are 40.4 and 35.6 kD, respectively. As a control we used purified NF-I<B p50 protein that is known to exist as a stable dimer in solution (Baeuerle and Baltimore 1989). The p50 protein is 45.8 kD calculated from its aminoacid sequence.

On both the gel filtration column and the glycerol gradient, the NFATp and NFATc rel domains migrated at a position close to their actual molecular weight. Under the same conditions, p50 behaved as species that was larger than its monomer molecular weight. The data from the gel filtration column was used to calculate the Stokes radius of each protein, and the S values were determined by glycerol gradient sedimentation. These two properties were used to calculate the apparent molecular size of the proteins (Siegel and Monty 1966; Thompson et al. 1991). The apparent molecular sizes of the NFATp and NFATc rel domains were determined to be 42 kD and 32 kD respectively. These values are close to the monomer molecular weight for both NFAT proteins. As expected, p50 exhibited an apparent molecular size close to that of a dimer.

After determining that NFAT rel domains were monomers in solution, we then considered the possibility that NFAT proteins might form dimers when bound to DNA. To address this question we carried out gel mobility shift assays with two different sized versions of NFATc translated in vitro (Hope and Struhl 1987). The shorter version contains the rel similarity region and a small amount of flanking residues and is referred to as NFATc-309. This construct is equivalent to the one that was expressed in $E.\ coli$. The larger version, NFATc-589, contains additional N-terminal sequences. When expressed individually in a rabbit reticulocyte lysate both versions of NFATc were active and produced protein-DNA complexes with different mobilities. When the two different NFATc proteins were mixed by co-translation the same protein-DNA complexes were apparent and no intermediate species was detectable, as would be expected if the proteins were forming dimers on the DNA. These results suggest that NFAT proteins are capable of sequence-specific DNA binding as monomers.

Methods

1. Isolation of human NFAT clones

Peripheral blood lymphocytes (PBLs) were isolated from 2 units of blood (obtained from Irwin Memorial Blood Bank, San Francisco) by fractionation on sodium metrizoate/polysaccharide (Lymphoprep, Nycomed) gradients. Jurkat T cells were grown in RPMI+10% fetal bovine serum. Total RNA was isolated from Jurkat cells or peripheral blood lymphocytes according to the Guanidinium-HCl method (Chomczynski and Sacchi 1987). Poly-A+ RNA was purified using oligo-dT magnetic beads (Promega). Random primed and oligo-dT primed libraries were prepared from both Jurkat and PBL RNA samples. The cDNA libraries were constructed in the vector Lambda ZAPII (Stratagene) according to the protocol supplied by the manufacturer. The cDNA was size selected for greater than 1 kb by electrophoresis a on 5% polyacrylamide gel prior to ligation. Each library contained approximately $2\times10^6$ recombinant clones. Each of the four libraries was screened independently under the same conditions.

The probe for the initial library screen was a 372 bp fragment derived by PCR from the C-terminal half of the rel homology domain of the mouse NFATp gene. This region corresponds to amino acids 370 through 496 in the published mNFATp sequence (McCaffrey et al. 1993). The fragment was labeled by random priming and hybridized in 1M NaCl, 50 mM Tris pH 7.4, 2 mM EDTA, 10X Denhardt's, 0.05% SDS, and 50 mg/ml salmon sperm DNA at 60° C. The filters were washed first in 2X SSC, 0.1% SDS, and then in 1X SSC, 0.1% SDS at 60° C. Hybridizing clones were purified and converted into Bluescript plasmid DNA clones. The DNA sequence was determined using thermal cycle sequencing and the Applied Biosystems 373A sequencer. Approximately 50 clones were isolated from the first set of screens. Sequence analysis and cross-hybridization experiments indicated that these clones were derived from 4 distinct genes. For NFAT4, additional cDNA clones were obtained from a skeletal muscle cDNA library (Stratagene). The 5' ends of the cDNA clones were obtained from a Jurkat cDNA library prepared as described above with gene specific primers for each of the NFAT genes.

2. Northerns

The northern blots with mRNA isolated from human tissues were purchased from Clontech. DNA probes were labeled by random priming and hybridized in 5X SSPE, 10X Denhardt's, 50% formamide, 2% SDS, 100 mg/ml salmon sperm DNA at 42° C. The filters were washed in 2X SSC/0.05% SDS at room temperature, and subsequently in 0.1X SSC/0.1% SDS at 60° C. For NFATp the probe was 1.2 kb cDNA fragment containing the entire rel similarity region of NFATp. For NFATc, the probe was a 291 nucleotide PCR fragment corresponding to the 3' end of rel similarity region (amino acids 597 to 693 (Northrop et al. 1994). For NFATc, a different set of blots was hybridized with a 0.8 kb cDNA fragment located upstream of the rel domain. The two different NFATc probes produced identical results. For NFAT3, the probe was a 0.6 kb fragment located downstream of the rel similarity region corresponding to the region encoding amino acid 720 through the 3' end of the clone. For NFAT4, the probe was a 1.3 kb cDNA fragment corresponding to residue 549 to 963 from the 4c class of cDNAs.

3. Protein Expression and Purification

*E. coli* expression vectors for each NFAT protein were constructed in the T7 polymerase expression vector pT7-HMK, which has an eight amino acid heart muscle kinase (hmk) site at the N-terminus. NdeI sites were introduced by PCR using mutagenic oligonucleotides in the coding regions upstream of the NFAT rel domains, and these restriction sites were subsequently used for cloning into pT7-HMK. The sizes of the different proteins (without the hmk sequences) are as follows: NFATp, 353 amino acids (the residues homologous to 185 through 537 according to McCaffrey et al. 1993); NFATc, 309 amino acids (amino acids 408 through 716 according to Northrop et al. 1994); NFAT3, 345 amino acids (residues 400 through 744); NFAT4, 316 amino acids (residues 393 through 708).

Proteins were expressed using the T7 polymerase expression system in the strain BL21(DE3) (Studier and Mofht 1986). Expression was induced by addition of 0.4 mM IPTG, and the cultures were shaken for 4 hours at room temperature. The cells were harvested, washed in PBS, resuspended in 0.4 M KC1-HEG (25 mM HEPES pH 7.9; 0.1 mM EDTA; 10% glycerol; 0.2% NP-40; 2 mM DTT, 0.2 mM PMSF, 0.2 mM sodium metabisulfite) and lysed by two cycles of freezethawing followed by sonication. The lysate was spun in an SS34 rotor at 10K for 10 min to remove insoluble material. NFAT proteins were purified from the soluble fractions of the extracts by DNA affinity chromatography (Kadonaga and Tjian 1986). The binding site sequence for the affinity resin was from the IL-4 promoter, TACATTGGAAAATTTTATTACAC (SEQ ID NO:17). The DNA was biotinylated on one strand and coupled to avidin agarose beads (Sigma) at a concentration of approximately 1 mg DNA/ml. Approximately 10 mg of *E. coli* extracts containing the recombinant NFAT proteins were loaded on 1.5 ml DNA columns equilibrated with 0.1 M KC1-HEG. The columns were washed successively with 0.1, 0.2, and 0.4 M HEG. The specifically bound NFAT proteins were eluted with 1.0 M KC1-HEG.

Fra-1 was expressed in *E. coli* from the vector pET11 (Novagen). The protein was purified from the soluble fraction to approximately 80% homogeneity by fractionation on heparin-sepharose. c-Jun protein was expressed in *E. coli* and purified from the insoluble portion of the extract as previously described (Bohmann and Tjian, 1989). The concentrations of the purified proteins were determined by comparing the intensity of coomassie staining with the staining intensity of BSA standards.

4. DNA Binding Experiments

Electrophoretic mobility shift assays were performed with the indicated amounts of proteins in 50 mM KCl, 25 mM HEPES, 0.05 mM EDTA, 5% glycerol, 1 mM DTT with 1 mg of poly(dI-dC)and 100 ng of BSA. The binding reactions and electrophoresis were carried out at room temperature. The samples were run on a 5% polyacrylamide, 0.5X TBE gel at 200 V.

5. Transfections

The full-length coding regions for each of the NFAT genes were subcloned into the RSV expression vector pREP4 (Invitrogen). The reporter plasmid was pXIL2-Luc (constructed by Jim Fraser). It contains the IL-2 promoter (−326 to +47, as in Durand et al 1988) upstream of the luciferase gene. Approximately $1 \times 10^6$ Jurkat cells were transiently transfected by lipofection (Lipofectin, Gibco/BRL). Twenty hours after transfection the cells were treated with 25 ng/ml PMA and 2 mM ionomycin, and the cells were harvested 8 hours after induction. Transfection efficiencies were standardized by co-transfection of pRSV-bgal and subsequent determination of bgal activity. Each transfection contained 2 mg of expression vector, 5 mg of luciferase reporter, and 1 mg of bgal plasmid and 10 ml of lipofectin. COS-7 and HepG2 cells were transfected by a modification of the calcium phosphate method (Chen and Okayarea 1987). The reporter gene contained three copies of the antigen response element (−286 to −257) upstream of the herpes virus tk minimal promoter (−50 to +28) in the luciferase vector pGL2 (Promega).

6. Gel Filtration Columns and glycerol gradients

Protein samples were run on a 2.4 ml Superalex-200 column using the Pharmacia Smart system. The column was equilibrated with 0.5M KCl-HEG at a flow rate of 80 ml/min. The elution volumes of purified NFATc, NFATp, and p50 were determined relative to those of molecular weight standards. Purified p50 was provided by Zhaodan Cao. The following molecular weight standards (10 mg) were chromatographed on separate runs: thyroglobulin (669 kD), b-amylase (200 kD), BSA (66 kD), carbonic anhydrase (29 kD), and cytochrome c (12 kD). The elution volume ($V_e$) was converted to $K_{av}$ by the equation, $K_{av}=(V_e-V_o)/V_i$, where $V_o$ is the void volume and $V_i$ is the included volume. The Stokes radii were determined from a plot of $(-\log K_{av})^{1/2}$ vs. the Stokes radii of the standards (Ackers 1970).

The S values were determined by glycerol gradient centrifugation. Five ml 10%–30% glycerol gradients were prepared using a Beckman density gradient former. The samples were centrifuged in a SW50Ti rotor at 39,000 rpm for 40 hours. After centrifugation, 200-ml fractions were collected and analyzed by gel electrophoresis and coomassie staining. The S values were determined by their sedimentation positions relative to the standards. Native molecular sizes were determined from the Stokes radii (a), S values (s), and the partial specific volumes (V) by the method of Siegel and Monty using the equation M=6pNas/1-V (Siegel and Monty 1966, Thompson et al. 1991 ).

7. References cited in Experimental Section

Ackers (1970) Adv. Prot. Chem. 24:343–446; Baeuerle and Baltimore (1989) Genes & Dev. 3:1689–1698; Baeuerle and Henkel (1994) Annu. Rev. Immunol. 12:141–179; Boise et al. (1993) Mol. Cell. Biol. 13:1911–1919; Brabletz et al. (1991) Nucl. Acids Res. 19:61–67; Chen and Okayarea (1.987) Mol. Cell. Biol. 7:2745–2752; Choi et al. (1994) Immunity, 1:179–187; Chomczynski and Sacchi (1987) Anal. Biochem. 162:156–159; Chuvpilo et al. (1993) Nucl. Acids Res. 21:5694–5704; Clipstone and Crabtree (1992) Nature 357:695–697; Cockerill et al. (1993) Proc. Natl. Acad. Sci. USA 90:2466–2470; Durand et al. (1988) Mol. Cell. Biol. 8:1715–1724; Goldfeld et al. (1993) J. Erp. Med. 178:1365–1379; Grabstein et al. (1994) Science 264:965–968;.Hohlfeld and Engel (1994) Immunol. Today 15:269–274; Hoyos et al. (1989) Science 244:457–460; Hope and Struhl (1987) EMBO J. 6:2781–2784; Jain et al. (1992) Nature 356:801–803; Jain et al. (1993) Nature 365:352–355; Jain et al. (1993) J. Immunol. 151:837–848; Jain et al. (1994) Mol. Cell. Biol. 14:1566–1574; Kaclonaga and Tjian (1986) Proc. Natl. Acad. Sci. USA 83:5889–5893; Masuda (1993) Mol. Cell. Biol. 13:7399–7407; McCaffrey et al. (1993) Science 262:750–754; McCaffrey et al. (1993) J. Biol. Chem. 268:3747–3752; Mouzaki and Rungget (1994) Blood 84:2612–2621; Nolan (1994) Cell 77:795–798; Northrop (1994) Nature 369:497–502; Northrop (1993) J. Biol. Chem. 268:2917–2293; Randak (1990) EMBO J. 9:2529–2536; Rooney (1994) EMBO J. 13:625–633; Schreiber and Crabtree (1992) Immunol. Today 13:136–142; Shaw (1988) Science 241:202–205; Siegel and Monty (1966)Biochim. Biophys. Acta 112:346–362; Studier and Moffat (1986) J. Mol. Biol. 189:113–130; Szabo (1993) Mol. Cell. Biol. 13:4793–4805; Thompson et al.(1991) Science 253:762–768; Venkataraman et al. (1994) Immunity 1:189–196; Verweij et al. (1990) J. Biol. Chem 265: 15788–15795; Yaseen et al. (1994) Mol. Cell. Biol. 14:6886–6895; and Yaseen et al. (1993) J. Biol. Chem. 268:14285–14293.

The following examples are offered by way of illustration and not by way of limitation.

EXAMPLES

1. Protocol for hNFAT - hNFAT dependent transcription factor binding assay.
A. Reagents:
 hNFAT: 20/xg/ml in PBS.
 Blocking buffer: 5% BSA, 0.5% Tween 20 in PBS; 1 hr, RT.
 Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.
 $^{33}$p hNFAT 10x stock: $10^{-8}$–$10^{-6}$ M "cold" hNFAT homolog supplemented with 200,000–250,000 cpm of labeled hNFAT homolog (Beckman counter). Place in the 4° C. microfridge during screening.
 Protease inhibitor cocktail (1000X): 10 mg Trypsin Inhibitor (BMB #109894), 10 mg Aprotinin (BMB #236624), 25 mg Benzamidine (Sigma #B- 6506), 25 mg Leupeptin (BMB #1017128), 10 mg APMSF (BMB #917575), and 2 mM NaVo$_3$ (Sigma # S-6508) in 10 ml of PBS.

B. Preparation of assay plates:
 Coat with 120 µl of stock NF-AT per well overnight at 4° C.
 Wash 2X with 200 µl PBS.
 Block with 150 µl of blocking buffer.
 Wash 2X with 200 µl PBS.
C. Assay:
 Add 80 µl assay buffer/well.
 Add 10 µl compound or extract.
 Add 10 µl 33P-NFAT (20,000–25,000 cpm/0.3 pmoles/well=3×10$^{-9}$M final concentration).
 Shake at 25° C. for 15 min.
 Incubate additional 45 min. at 25° C.
 Stop the reaction by washing 4X with 200 µl PBS.
 Add 150 µl scintillation cocktail.
 Count in Topcount.
D. Controls for all assays (located on each plate):
 a. Non-specific binding (no hNFAT added)
 b. cold hNFAT at 80% inhibition.

2. Protocol for hNFAT - AP1 dependent transcription factor binding assay.
A. Reagents:
 fos-jun heterodimers (junB and fra1): 20 µg/ml in PBS.
 Blocking buffer: 5% BSA, 0.5% Tween 20 in PBS; 1 hr, RT.
 Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.
 $^{33}$p hNFAT 10x stock: $10^{-8}$–$10^{-6}$M "cold" hNFAT homolog supplemented with 200,000–250,000 cpm of labeled hNFAT homolog (Beckman counter). Place in the 4° C. microfridge during screening.
 Protease inhibitor cocktail (1000X): 10 mg Trypsin Inhibitor (BMB #109894), 10 mg Aprotinin (BMB #236624), 25 mg Benzamidine (Sigma #B- 6506), 25 mg Leupeptin (BMB #1017128), 10 mg APMSF (BMB #917575), and 2 mM NaVo$_3$ (Sigma #S-6508) in 10 ml of PBS.
B. Preparation of assay plates:
 Coat with 120 µl of stock fos-jun heterodimers per well overnight at 4° C.
 Wash 2X with 200 µl PBS.
 Block with 150 µl of blocking buffer.
 Wash 2X with 200 µl PBS.
C. Assay:
 Add 80 µl assay buffer/well.
 Add 10 µl compound or extract.
 Add 10 µl 33P-NFAT (20,000–25,000 cpm/0.3 pmoles/well=3×10$^{-9}$ M final concentration).
 Shake at 25° C. for 15 min.
 Incubate additional 45 min. at 25° C.
 Stop the reaction by washing 4X with 200 µl PBS.
 Add 150 µl scintillation cocktail.
 Count in Topcount.
D. Controls for all assays (located on each plate):
 a. Non-specific binding (no hNFAT added)
 b. cold hNFAT at 80% inhibition, 3. Protocol for hNFAT-fos-jun dependent transcription factor—DNA binding assay.
A. Reagents:
 Neutralite Avidin: 20 µg/ml in PBS.
 Blocking buffer: 5% BSA, 0.5% Tween 20 in PBS; 1 hr, RT.
 Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.
 $^{33}$p hNFAT 10x stock: $10^{-6}$–$10^{-8}$ M "cold" hNFAT homolog supplemented with 200,000–250,000 cpm of labeled hNFAT homolog (Beckman counter) and $10^{-6}$–$10^{-8}$ M fos-jun heterodimers. Place in the 4° C. microfridge during screening.

Protease inhibitor cocktail (1000X): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM $NaVo_3$ (Sigma #S-6508) in 10 ml of PBS.

Oligonucleotide stock: (specific biotinylated). Biotinylated oligo at 17 pmole/µl, AP1-NFAT site: (BIOTIN)-GG AGG AAA AAC TGT TTC ATA CAG AAG GCG T (SEQ ID NO: 18)

B. Preparation of assay plates:

Coat with 120 µl of stock N-Avidin per well overnight at 4° C.

Wash 2X with 200 µl PBS.

Block with 150 µl of blocking buffer.

Wash 2X with 200 µl PBS.

C. Assay:

Add 40 µl assay buffer/well.

Add 10 µl compound or extract.

Add 10 µl $^{33}$P-NFAT (20,000–25,000 cpm/0.1–10 pmoles/well=$10^{-9}$–$10^{-7}$ M final concentration).

Shake at 25° C. for 15 min.

Incubate additional 45 min. at 25° C.

Add 40 µl oligo mixture (1.0 pmoles/40 ul in assay buffer with 1 ng of ss-DNA)

Incubate 1 hr at RT.

Stop the reaction by washing 4X with 200 µl PBS.

Add 150 µl scintillation cocktail.

Count in Topcount.

D. Controls for all assays (located on each plate):
a. Non-specific binding (no oligo added)
b. Specific soluble oligo at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

---

What is claimed is:

1. An isolated human nuclear factor of activated T-cells, hNFAT, protein comprising hNFATp$_1$ (SEQ ID NO:2), hNFATp$_2$ (SEQ ID NO:2, residues 220–921), hNFAT3 (SEQ ID NO:6), hNFAT4b (SEQ ID NO: 10) or hNFAT4c (SEQ ID NO:12).

2. The isolated protein according to claim 1, wherein said protein comprises hNFATp$_1$ (SEQ ID NO:2).

3. The isolated protein according to claim 1, wherein said protein comprises hNFATp$_2$ (SEQ ID NO:2, residues 220–921).

4. The isolated protein according to claim 1, wherein said protein comprises hNFAT3 (SEQ ID NO:6).

5. The isolated protein according to claim 1, wherein said protein comprises hNFAT4b (SEQ ID NO:10).

6. The isolated protein according to claim 1, wherein said protein Comprises hNFAT4c (SEQ ID NO:12).

* * * * *